United States Patent
Greene

(10) Patent No.: US 9,453,214 B2
(45) Date of Patent: Sep. 27, 2016

(54) POLYPEPTIDE STRUCTURAL MOTIFS ASSOCIATED WITH CELL SIGNALING ACTIVITY

(71) Applicant: aTyr Pharma, Inc., San Diego, CA (US)

(72) Inventor: Leslie Ann Greene, San Diego, CA (US)

(73) Assignee: aTyr Pharma, Inc., San Diego, CA (US)

( * ) Notice: Subject to any disclaimer, the term of this patent is extended or adjusted under 35 U.S.C. 154(b) by 0 days.

(21) Appl. No.: 14/452,914

(22) Filed: Aug. 6, 2014

(65) Prior Publication Data

US 2015/0064188 A1    Mar. 5, 2015

Related U.S. Application Data

(63) Continuation of application No. 13/203,831, filed as application No. PCT/US2010/025642 on Feb. 26, 2010, now abandoned.

(60) Provisional application No. 61/156,370, filed on Feb. 27, 2009.

(51) Int. Cl.
| | |
|---|---|
| C12N 9/00 | (2006.01) |
| C12P 21/06 | (2006.01) |
| C12P 21/04 | (2006.01) |
| C12N 15/00 | (2006.01) |
| A61K 38/46 | (2006.01) |
| C07K 14/52 | (2006.01) |
| C12N 9/02 | (2006.01) |
| G01N 33/68 | (2006.01) |
| C07K 16/40 | (2006.01) |
| A61K 38/00 | (2006.01) |

(52) U.S. Cl.
CPC ............... *C12N 9/93* (2013.01); *C07K 14/521* (2013.01); *C07K 16/40* (2013.01); *C12N 9/0036* (2013.01); *G01N 33/68* (2013.01); *A61K 38/00* (2013.01); *C12Y 601/01012* (2013.01); *G01N 2333/52* (2013.01); *G01N 2333/9015* (2013.01); *G01N 2500/04* (2013.01); *G01N 2500/10* (2013.01); *G01N 2500/20* (2013.01); *Y10T 436/143333* (2015.01)

(58) Field of Classification Search
CPC ....................................................... C12N 9/93
See application file for complete search history.

(56) References Cited

U.S. PATENT DOCUMENTS

| | | |
|---|---|---|
| 5,370,995 A | 12/1994 | Hennecke et al. |
| 5,484,703 A | 1/1996 | Raben et al. |
| 5,663,066 A | 9/1997 | Raben et al. |
| 5,750,387 A | 5/1998 | Hodgson et al. |
| 5,753,480 A | 5/1998 | Lawlor |
| 5,756,327 A | 5/1998 | Sassanfar et al. |
| 5,759,833 A | 6/1998 | Shiba et al. |
| 5,776,749 A | 7/1998 | Hodgson et al. |
| 5,795,757 A | 8/1998 | Hodgson et al. |
| 5,798,240 A | 8/1998 | Martinis et al. |
| 5,801,013 A | 9/1998 | Tao et al. |
| 5,866,390 A | 2/1999 | Lawlor |
| 5,885,815 A | 3/1999 | Sassanfar et al. |
| 5,928,920 A | 7/1999 | Hodgson et al. |
| 5,939,298 A | 8/1999 | Brown et al. |
| 6,225,060 B1 | 5/2001 | Clark et al. |
| 6,255,090 B1 | 7/2001 | Famodu et al. |
| 6,265,188 B1 | 7/2001 | Brown et al. |
| 6,428,960 B1 | 8/2002 | Clark et al. |
| 6,548,060 B1 | 4/2003 | Kim |
| 6,696,619 B1 | 2/2004 | Famodu et al. |
| 6,852,512 B2 | 2/2005 | Choi et al. |
| 6,903,189 B2 | 6/2005 | Schimmel et al. |
| 7,067,126 B2 | 6/2006 | Schimmel et al. |
| 7,144,984 B2 | 12/2006 | Schimmel et al. |
| 7,196,068 B2 | 3/2007 | Kim et al. |
| 7,273,844 B2 | 9/2007 | Schimmel et al. |
| 7,413,885 B2 | 8/2008 | Schimmel et al. |
| 7,459,529 B2 | 12/2008 | Kim |
| 7,476,651 B2 | 1/2009 | Schimmel et al. |
| 7,521,215 B2 | 4/2009 | Schimmel et al. |
| 7,528,106 B2 | 5/2009 | Friedlander et al. |
| 7,745,391 B2 | 6/2010 | Mintz et al. |
| 7,842,467 B1 | 11/2010 | Heidbrink et al. |
| 7,901,917 B2 | 3/2011 | Schimmel et al. |
| 7,902,165 B2 | 3/2011 | Kim |

(Continued)

FOREIGN PATENT DOCUMENTS

| | | |
|---|---|---|
| CN | 1341725 | 3/2002 |
| CN | 1341727 | 3/2002 |

(Continued)

OTHER PUBLICATIONS

Protein Purification Handbook. GE Healthcare. 2001.*
International Preliminary Report on Patentability for International Application No. PCT/US2009/048915, dated Jan. 5, 2011.
International Search Report and Written Opinion for International Application No. PCT/US2009/048915, mailed Nov. 2, 2009.
Office Action for U.S. Appl. No. 12/482,151, mailed Oct. 11, 2011, 43 pages.
Office Action for U.S. Appl. No. 12/482,151, mailed Mar. 18, 2011, 11 pages.
International Preliminary Report on Patentability for International Application No. PCT/US2009/046910, dated Dec. 13, 2010.
International Search Report and Written Opinion for International Application No. PCT/US2009/046910, mailed Mar. 4, 2010.

(Continued)

*Primary Examiner* — Yong Pak
(74) *Attorney, Agent, or Firm* — Cooley LLP

(57) ABSTRACT

Isolated polypeptides comprising or consisting essentially of specific structural motifs (e.g., three β-sheets and two α-helices) are provided, wherein the polypeptides exhibit at least one cell signaling and/or other non-canonical activity of biological relevance. Also provided are polynucleotides encoding such polypeptides, binding agents that bind such polypeptides, analogs, variants and fragments of such polypeptides, etc., as well as compositions and methods of identifying and using any of the foregoing.

6 Claims, 10 Drawing Sheets

(56) References Cited

U.S. PATENT DOCUMENTS

| | | |
|---|---|---|
| 8,003,780 B2 | 8/2011 | Kim et al. |
| 8,017,593 B2 | 9/2011 | Schimmel et al. |
| 8,026,088 B2 | 9/2011 | Yang |
| 8,101,566 B2 | 1/2012 | Schimmel et al. |
| 8,148,125 B2 | 4/2012 | Schimmel et al. |
| 8,404,242 B2 | 3/2013 | Zhou et al. |
| 8,404,471 B2 | 3/2013 | Greene et al. |
| 8,481,296 B2 | 7/2013 | Yang |
| 8,946,157 B2 | 2/2015 | Greene et al. |
| 2002/0182666 A1 | 12/2002 | Schimmel et al. |
| 2003/0004309 A1 | 1/2003 | Kim et al. |
| 2003/0017564 A1 | 1/2003 | Schimmel et al. |
| 2003/0018985 A1 | 1/2003 | Falco et al. |
| 2003/0082575 A1 | 5/2003 | Schultz et al. |
| 2003/0134301 A1 | 7/2003 | Brooksbank et al. |
| 2003/0158400 A1 | 8/2003 | Tang et al. |
| 2003/0165921 A1 | 9/2003 | Tang et al. |
| 2003/0166241 A1 | 9/2003 | Famodu et al. |
| 2003/0215827 A1 | 11/2003 | Yue et al. |
| 2004/0009163 A1 | 1/2004 | Schimmel et al. |
| 2004/0018505 A1 | 1/2004 | Lee et al. |
| 2004/0048290 A1 | 3/2004 | Lee et al. |
| 2004/0101879 A1 | 5/2004 | Seidel-Dugan et al. |
| 2004/0152079 A1 | 8/2004 | Schimmel et al. |
| 2004/0203094 A1 | 10/2004 | Martinis et al. |
| 2004/0214216 A1 | 10/2004 | Famodu et al. |
| 2004/0224981 A1 | 11/2004 | Janjic et al. |
| 2005/0136513 A1 | 6/2005 | Zhang |
| 2005/0196754 A1 | 9/2005 | Drmanac et al. |
| 2005/0208536 A1 | 9/2005 | Schultz et al. |
| 2006/0024288 A1 | 2/2006 | Glidden |
| 2006/0035232 A1 | 2/2006 | McGregor et al. |
| 2006/0046250 A1 | 3/2006 | Kim |
| 2006/0078553 A1 | 4/2006 | Glidden |
| 2006/0160175 A1 | 7/2006 | Anderson et al. |
| 2006/0248617 A1 | 11/2006 | Imanaka et al. |
| 2007/0048322 A1 | 3/2007 | Schimmel et al. |
| 2007/0061916 A1 | 3/2007 | Kovalic et al. |
| 2007/0111238 A1 | 5/2007 | Jamieson et al. |
| 2007/0224201 A1 | 9/2007 | Wu et al. |
| 2008/0044854 A1 | 2/2008 | Wang et al. |
| 2008/0113914 A1 | 5/2008 | Hays et al. |
| 2008/0153745 A1 | 6/2008 | Tian |
| 2009/0123971 A1 | 5/2009 | Paulsel et al. |
| 2009/0226966 A1 | 9/2009 | Yokoyama et al. |
| 2009/0227002 A1 | 9/2009 | Schultz et al. |
| 2009/0227662 A1 | 9/2009 | Schimmel et al. |
| 2009/0285792 A1 | 11/2009 | Friedlander et al. |
| 2010/0003230 A1 | 1/2010 | Glidden |
| 2010/0028352 A1 | 2/2010 | Greene et al. |
| 2010/0048413 A1 | 2/2010 | Arcus et al. |
| 2010/0092434 A1 | 4/2010 | Belani et al. |
| 2010/0093082 A1 | 4/2010 | Tian et al. |
| 2010/0138941 A1 | 6/2010 | Kim et al. |
| 2010/0167997 A1 | 7/2010 | Kim |
| 2010/0297149 A1 | 11/2010 | Zhou et al. |
| 2010/0310576 A1 | 12/2010 | Adams et al. |
| 2011/0104139 A1 | 5/2011 | Faber |
| 2011/0110917 A1 | 5/2011 | Schimmel et al. |
| 2011/0117572 A1 | 5/2011 | Kim et al. |
| 2011/0124582 A1 | 5/2011 | Kim et al. |
| 2011/0136119 A1 | 6/2011 | Kim et al. |
| 2011/0150885 A1 | 6/2011 | Watkins et al. |
| 2011/0189195 A1 | 8/2011 | Kim et al. |
| 2011/0250701 A1 | 10/2011 | Kim et al. |
| 2011/0256119 A1 | 10/2011 | Kim et al. |
| 2012/0004185 A1 | 1/2012 | Greene |
| 2012/0010141 A1 | 1/2012 | Kim |
| 2012/0015383 A1 | 1/2012 | Park et al. |
| 2012/0058133 A1 | 3/2012 | Whitman et al. |
| 2012/0064082 A1 | 3/2012 | Watkins et al. |
| 2013/0052177 A1 | 2/2013 | Schimmel et al. |
| 2013/0108630 A1 | 5/2013 | Watkins et al. |
| 2013/0129703 A1 | 5/2013 | Chiang et al. |
| 2013/0129704 A1 | 5/2013 | Greene et al. |
| 2013/0129705 A1 | 5/2013 | Greene et al. |
| 2013/0142774 A1 | 6/2013 | Greene et al. |
| 2013/0195832 A1 | 8/2013 | Greene et al. |
| 2013/0202574 A1 | 8/2013 | Greene et al. |
| 2013/0202575 A1 | 8/2013 | Greene et al. |
| 2013/0202576 A1 | 8/2013 | Greene et al. |
| 2013/0209434 A1 | 8/2013 | Greene et al. |
| 2013/0209472 A1 | 8/2013 | Greene et al. |
| 2013/0224173 A1 | 8/2013 | Greene et al. |
| 2013/0224174 A1 | 8/2013 | Greene et al. |
| 2013/0230505 A1 | 9/2013 | Greene et al. |
| 2013/0230507 A1 | 9/2013 | Greene et al. |
| 2013/0230508 A1 | 9/2013 | Greene et al. |
| 2013/0236440 A1 | 9/2013 | Greene et al. |
| 2013/0236455 A1 | 9/2013 | Greene et al. |
| 2013/0243745 A1 | 9/2013 | Greene et al. |
| 2013/0243766 A1 | 9/2013 | Zhou et al. |
| 2013/0273045 A1 | 10/2013 | Watkins et al. |
| 2013/0280230 A1 | 10/2013 | Greene et al. |
| 2013/0287755 A1 | 10/2013 | Greene et al. |
| 2013/0315887 A1 | 11/2013 | Greene et al. |
| 2013/0330312 A1 | 12/2013 | Greene et al. |
| 2013/0344096 A1 | 12/2013 | Chiang et al. |
| 2014/0066321 A1 | 3/2014 | Xu et al. |
| 2014/0255375 A1 | 9/2014 | Belani et al. |
| 2014/0255378 A1 | 9/2014 | Watkins et al. |
| 2014/0302075 A1 | 10/2014 | Buechler et al. |
| 2014/0335087 A1 | 11/2014 | Buechler et al. |
| 2014/0349369 A1 | 11/2014 | Buechler et al. |
| 2014/0363415 A1 | 12/2014 | Greene et al. |
| 2014/0371294 A1 | 12/2014 | Zhou et al. |
| 2015/0093799 A1 | 4/2015 | Chiang et al. |
| 2015/0140072 A1 | 5/2015 | Watkins et al. |
| 2015/0159148 A1 | 6/2015 | Buechler et al. |
| 2015/0231214 A1 | 8/2015 | Greene et al. |
| 2015/0240227 A1 | 8/2015 | Greene et al. |
| 2015/0240228 A1 | 8/2015 | Greene et al. |
| 2015/0252347 A1 | 9/2015 | Greene et al. |
| 2015/0252348 A1 | 9/2015 | Greene et al. |
| 2015/0252349 A1 | 9/2015 | Greene et al. |
| 2015/0284704 A1 | 10/2015 | Greene et al. |
| 2015/0284705 A1 | 10/2015 | Greene et al. |
| 2015/0284706 A1 | 10/2015 | Greene et al. |
| 2015/0290305 A1 | 10/2015 | Greene et al. |
| 2015/0353914 A1 | 12/2015 | Greene et al. |
| 2015/0361412 A1 | 12/2015 | Greene et al. |
| 2015/0361413 A1 | 12/2015 | Greene et al. |

FOREIGN PATENT DOCUMENTS

| | | |
|---|---|---|
| CN | 1352242 | 6/2002 |
| CN | 1352252 | 6/2002 |
| EP | 0785265 | 7/1997 |
| EP | 0893494 | 1/1999 |
| EP | 0893496 | 1/1999 |
| EP | 0897004 | 2/1999 |
| EP | 1275720 | 1/2003 |
| EP | 1300468 | 4/2003 |
| EP | 1377305 | 1/2009 |
| EP | 1776138 | 10/2009 |
| EP | 1274834 | 7/2010 |
| WO | WO 97/26351 | 7/1997 |
| WO | WO 97/39017 | 10/1997 |
| WO | WO 99/45130 | 9/1999 |
| WO | WO 01/74841 | 10/2001 |
| WO | WO 01/75067 | 10/2001 |
| WO | WO 01/75078 | 10/2001 |
| WO | WO 01/90330 | 11/2001 |
| WO | WO 01/94568 | 12/2001 |
| WO | WO 02/055663 | 7/2002 |
| WO | WO 02/059323 | 8/2002 |
| WO | WO 02/067970 | 9/2002 |
| WO | WO 03/009813 | 2/2003 |
| WO | WO 03/080648 | 10/2003 |
| WO | WO 03/094862 | 11/2003 |
| WO | WO 2004/030615 | 4/2004 |
| WO | WO 2005/019258 | 3/2005 |
| WO | WO 2005/102395 | 11/2005 |
| WO | WO 2005/117954 | 12/2005 |

(56) References Cited

FOREIGN PATENT DOCUMENTS

| WO | WO 2006/016217 | 2/2006 |
|---|---|---|
| WO | WO 2006/057500 | 6/2006 |
| WO | WO 2007/064941 | 6/2007 |
| WO | WO 2007/139397 | 12/2007 |
| WO | WO 2008/007818 | 1/2008 |
| WO | WO 2008/016356 | 2/2008 |
| WO | WO 2008/021290 | 2/2008 |
| WO | WO 2008/133359 | 11/2008 |
| WO | WO 2009/114623 | 9/2009 |
| WO | WO 2009/152247 | 12/2009 |
| WO | WO 2009/158649 | 12/2009 |
| WO | WO 2010/021415 | 2/2010 |
| WO | WO 2010/041892 | 4/2010 |
| WO | WO 2010/041913 | 4/2010 |
| WO | WO 2010/090471 | 8/2010 |
| WO | WO 2010/096170 | 8/2010 |
| WO | WO 2010/099477 | 9/2010 |
| WO | WO 2010/107825 | 9/2010 |
| WO | WO 2010/120509 | 10/2010 |
| WO | WO 2011/072265 | 6/2011 |
| WO | WO 2011/072266 | 6/2011 |
| WO | WO 2011/097031 | 8/2011 |
| WO | WO 2012/009289 | 1/2012 |

OTHER PUBLICATIONS

Supplementary European Search Report for European Application No. 06838844.6, mailed Apr. 9, 2009, 10 pages.
Office Action for U.S. Appl. No. 12/085,884, mailed Jan. 20, 2011.
International Preliminary Report on Patentability for International Application No. PCT/US2006/046106, dated Jun. 4, 2008.
International Search Report and Written Opinion for International Application No. PCT/US2006/046106, mailed Aug. 9, 2007.
Supplementary European Search Report for European Application No. 10746935.5, mailed Oct. 26, 2012.
Office Action for U.S. Appl. No. 13/203,831, mailed Oct. 7, 2013, 20 pages.
Office Action for U.S. Appl. No. 13/203,831, mailed Apr. 7, 2014, 24 pages.
International Preliminary Report on Patentability for International Application No. PCT/US2010/025642, dated Aug. 30, 2011.
International Search Report and Written Opinion for International Application No. PCT/US2010/025642, mailed Oct. 29, 2010.
Supplementary European Search Report for European Application No. 10764856.0, mailed Sep. 5, 2012.
Office Action for U.S. Appl. No. 12/751,358, mailed Oct. 3, 2011.
Office Action for U.S. Appl. No. 12/751,358, mailed Mar. 3, 2011.
International Preliminary Report on Patentability for International Application No. PCT/US2010/029377, dated Oct. 4, 2011.
International Search Report and Written Opinion for International Application No. PCT/US2010/029377, mailed Jan. 26, 2011.
Office Action for U.S. Appl. No. 12/725,272,mailed Jul. 13, 2012, 9 pages.
Restriction Requirement for U.S. Appl. No. 12/725,272, mailed Apr. 27, 2012.
International Preliminary Report on Patentability for International Application No. PCT/US2010/027525, dated Sep. 20, 2011.
International Search Report and Written Opinion for International Application No. PCT/US2010/027525, mailed Jan. 10, 2011.
International Search Report and Written Opinion for International Application No. PCT/US2010/059964, mailed Aug. 25, 2011.
International Preliminary Report on Patentability for International Application No. PCT/US2010/059964, dated Jun. 12, 2012.
International Preliminary Report on Patentability for International Application No. PCT/US2010/059963, dated Jun. 12, 2012, 18 pages.
International Search Report and Written Opinion for International Application No. PCT/US2010/059963, mailed May 12, 2011.
International Search Report and Written Opinion for International Application No. PCT/US2011/000210, mailed Aug. 12, 2011.
International Search Report and Written Opinion for International Application No. PCT/US2011/043596, mailed on Feb. 29, 2012.
International Preliminary Report on Patentability for International Application No. PCT/US2011/043596, dated Jan. 15, 2013.
International Search Report and Written Opinion for International Application No. PCT/US2012/068282, mailed on Apr. 1, 2013.
International Search Report and Written Opinion for International Application No. PCT/US2012/068296, mailed on Apr. 19, 2013.
Adams, M. D. et al., "The genome sequence of drosophila melanogaster," Science, 287(5961):2185-2195 (2000).
Aderem, A. et al., "Toll-like receptors in the induction of the innate immune response," Nature, 406:782-787 (2000).
Amaar, Y. G. et al., "Cloning and characterization of the C.elegans histidyl-tRNA synthetase gene," Nucleic Acids Research, 21(18):4344-4347 (1993).
Antonellis, A. et al., "The Role of Aminoacyl-tRNA Synthetases in Genetic Diseases," Annual Review of Genomics and Human Genetics, 9(1):87-107 (2008).
Ascherman, D. P. et al., "Critical Requirement for Professional APCs in Eliciting T Cell Responses to Novel Fragments of Histidyl-tRNA Synthetase (Jo-1) in Jo-1 Antibody-Positive Polymyositis," J. Immunol., 169:7127-7134 (2002).
Ascherman, D. P., "The Role of Jo-1 in the Immunopathogenesis of Polymyositis: Current Hypotheses," Current Rheumatology Reports, 5:425-430 (2003).
Barbasso, S. et al., "Sera From Anti-Jo-1-Positive Patients with Polymyositis and Interstitial Lung Disease Induce Expression of Intercellular Adhesion Molecule 1 in Human Lung Endothelial Cells," Arthritis & Rheumatism, 60(8):2524-2530 (2009).
Bernstein, R. M. et al., "Anti-Jo-1 antibody: a marker for myositis with interstitial lung disease," British Medical Journal, 289:151-152 (1984).
Blechynden, L.M. et al., "Sequence and polymorphism analysis of the murine gene encoding histidyl-tRNA synthetase," Gene, 178:151-156 (1996).
Blechynden, L.M. et al., "Myositis Induced by Naked DNA Immunization with the Gene for Histidyl-tRNA Synthetase," Human Gene Therapy, 8:1469-1480 (Aug. 10, 1997).
Blum, D. et al., "Extracellular toxicity of 6-hydroxydopamine on PC12 cells," Neuroscience Letters, 283(3):193-196 (2000).
Branden et al., "Introduction to Protein Structure," Garland Publishing Inc., New York, p. 247 (1991).
Brightbill, H. D. et al., "Toll-like receptors: molecular mechanisms of the mammalian immune response," Immunology, 101:1-10 (2000).
Broun, P. et al., "Catalytic plasticity of fatty acid modification enzymes underlying chemical diversity of plant lipids," Science, 282:1315-1317 (1998).
Brown, M. V. et al., "Mammalian aminoacyl-tRNA synthetases: Cell signaling functions of the protein translation machinery," Vascular Pharmacology, 52(1-2):21-26 (2010).
Car, B. D. et al., "Interferon y Receptor Deficient Mice Are Resistant to Endotoxic Shock," J. Exp. Med., 179:1437-1444, 1994.
Casciola-Rosen, L. et al., "Cleavage by Granzyme B is Strongly Predictive of Autoantigen Status: Implications for Initiation of Autoimmunity," J. Exp. Med., 190(6):815-825 (1999).
Casciola-Rosen, L., "Histidyl-Transfer RNA Synthetase: A Key Participant in Idiopathic Inflammatory Myopathies," Arthritis and Rheumatism, 63(2):331-333 (2011).
Cheong et al., "Structure of the N-terminal extension of human aspartyl-tRNA synthetase: implications for its biological function," The International Journal of Biochemistry & Cell Biology, 35:1548-1557, 2003.
Chica, R. A. et al., "Semi-rational approaches to engineering enzyme activity: combining the benefits of directed evolution and rational design," Curr. Opin. Biotechnol., 16:378-384 (2005).
Choi, W. S. et al., "Two Distinct Mechanisms Are Involved in 6-Hydroxydopamine-and MPP+-Induced Dopaminergic Neuronal Cell Death: Role of Caspases, ROS, and JNK," Journal of Neuroscience Research, 57(1):86-94 (1999).
Datson, N. A. et al., "Development of the first marmoset-specific DNA microarray (EUMAMA): a new genetic tool for large-scale expression profiling in a non-human primate," BMC Genomics, 8(190):1-9 (2007).

(56) References Cited

OTHER PUBLICATIONS

Delgado, C. et al., "The uses and properties of PEG-linked proteins," Critical Reviews in Therapeutic Drug Carrier Systems, 9(3,4):249-304 (1992).
Devos, D. et al., "Practical limits of function prediction," Proteins: Structure, Function, and Genetics, 41:98-107 (2000).
Eriani, G. et al., "Cytoplasmic aspartyl-tRNA synthetase from Saccharomyces cerevisiae. Study of its functional organisation by deletion analysis," European Journal of Biochemistry, 200(2):337-343 (1991).
Escalante, C., et al., "Expression of human aspartyl-tRNA synthetase in COS cells," Molecular and Cellular Biochemistry, 140(1):55-63 (1994).
Escalante, C. et al., "Expression of Human Aspartyl-tRNA Synthetase in Escherichia coli: Functional Analysis of the N-Terminal Putative Amphiphilic Helix," The Journal of Biological Chemistry, 268(8):6014-6023 (1993).
Ewalt, K. L. et al., "Activation of Angiogenic Signaling Pathways by Two Human tRNA Synthetases," Biochemistry, 41(45):13344-13349 (2002).
Frommhold, D. et al., "Sialyltransferase ST3Gal-IV controls CXCR2-mediated firm leukocyte arrest during inflammation," Journal of Experimental Medicine, 205(6):1435-1446 (2008).
GenBank Accession No. AA131122, Nov. 27, 1996.
GenBank Accession No. AA281081, Apr. 2, 1997.
GenBank Accession No. AA355758, Apr. 21, 1997.
GenBank Accession No. AA984229, published May 27, 1998.
GenBank Accession No. AI985978, Aug. 31, 1999.
GenBank Accession No. AK055917, published Jan. 19, 2008.
GenBank Accession No. AK124831, published Jul. 3, 2008.
GenBank Accession No. AK225776, published Jul. 22, 2006.
GenBank Accession No. AK293154, published Jul. 24, 2008.
GenBank Accession No. AK295219, published Jul. 24, 2008.
GenBank Accession No. AK302295, published Jul. 24, 2008.
GenBank Accession No. AK303778, published Jul. 24, 2008.
GenBank Accession No. AU129836, published Feb. 18, 2011.
GenBank Accession No. AV685924, Sep. 25, 2000.
GenBank Accession No. AW070887, Oct. 13, 1999.
GenBank Accession No. BE695954, Sep. 11, 2000.
GenBank Accession No. BE872272, published Jan. 13, 2011.
GenBank Accession No. BF437672, Nov. 29, 2000.
GenBank Accession No. BF526055, Dec. 4, 2000.
GenBank Accession No. BF791754, published Jan. 13, 2011.
GenBank Accession No. BG108830, published Jun. 1, 2001.
GenBank Accession No. BG700836, May 7, 2001.
GenBank Accession No. BI559642, Sep. 4, 2001.
GenBank Accession No. BI599431, Sep. 5, 2001.
GenBank Accession No. BM827507, Mar. 6, 2002.
GenBank Accession No. BP268250, published Feb. 10, 2011.
GenBank Accession No. BQ002750, Mar. 26, 2002.
GenBank Accession No. BU599828, Sep. 19, 2002.
GenBank Accession No. CA865450, Dec. 20, 2002.
GenBank Accession No. CA865692, Dec. 20, 2002.
GenBank Accession No. CD694017, Jun. 25, 2003.
GenBank Accession No. CR749809, Oct. 7, 2008.
GenBank Accession No. DA083923, published Feb. 17, 2011.
GenBank Accession No. DB146646, published Feb. 16, 2011.
GenBank Accession No. J05032, published Apr. 27, 1993.
GenBank Accession No. Q7QD89, Anopheles gambiae Sequence Committee, submitted Apr. 2002, [Retrieved from the Internet Apr. 24, 2007], <URL: http://www.ncbi.nlm.nih.gov/entrez/viewer.fcgi?db=protein&val=74803944>.
GenBank Accession No. Q9VV60, published May 1, 2000.
GenBank Accession No. Z11518, published Oct. 7, 2008.
Goldgur, Y. et al., "The crystal structure of phenylalanyl-tRNA synthetase from Thermus thermophilus complexed with cognate tRNA," Structure, 5(1):59-68 (1997).
Greenberg, Y. et al., "The novel fragment of tyrosyl tRNA synthetase, mini-TyrRS, is secreted to induce an angiogenic response in endothelial cells," FASEB Journal, 22(5):1597-1605 (2008).
Guijarro, J. I. et al., "Structure and Dynamics of the Anticodon Arm Binding Domain of Bacillus stearothermophilus Tyrosyl-tRNA Synthetase," Structure, 10(3):311-317 (2002).
Guo, R-T. et al., "Crystal structures and biochemical analyses suggest a unique mechanism and role for human glycyl-tRNA synthetase in Ap4A homeostasis," Journal of Biological Chemistry, 284(42):28968-28976 (2009).
Guo, M. et al., "Functional expansion of human tRNA synthetases achieved by structural inventions," FEBS Letters, 584(2):434-442 (2010).
Guo, M. et al., "New functions of aminoacyl-tRNA synthetases beyond translation," Nature Reviews Molecular Cell Biology, 11:668-674 (2010).
Hanrott, K. et al., "6-Hydroxydopamine-induced Apoptosis is Mediated via Extracellular Auto-oxidation and Caspase 3-dependent Activation of Protein Kinase C8," The Journal of Biological Chemistry, 281(9):5373-5382 (2006).
Hausmann, C. D. et al., "Aminoacyl-tRNA synthetase complexes: molecular multitasking revealed," FEMS Microbiol. Rev., 32(4):705-721 (2008).
Hengstman, G. J. D. et al., "Anti-Jo-1 positive inclusion body myositis with a marked and sustained clinical improvement after oral prednisone," J. Neurol. Neurosurg. Psychiatry, 70(5):706 (2001).
Hou, Y-M. et al., "Sequence determination and modeling of structural motifs for the smallest monomeric aminoacyl-tRNA synthetase," Proc. Nat. Acad. Sci., 88(3):976-980 (1991).
Howard, O. M. Z. et al., "Histidyl-tRNA Synthetase and Asparaginyl-tRNA Synthetase, Autoantigens in Myositis, Activate Chemokine Receptors on T Lymphocytes and Immature Dendritic Cells," The Journal of Experimental Medicine, 196(6):781-791 (2002).
Howard, O. M. Z. et al., "Autoantigens signal through cheokine receptors: uveitis antigens induce CXCR3- and CRCR5-expressing lymphocytes and immature dendritic cells to migrate", Blood, 105(11) 4207-4214 (2005).
Ivakhno, S. S. et al., "Cytokine-Like Activities of Some Aminoacyl-tRNA Synthetases and Auxiliary p43 Cofactor of Aminoacylation Reaction and Their Role in Oncogenesis," Exp. Oncol., 26(4):250-255 (2004).
Izumi, Y. et al., "p-Quinone Mediates 6-Hydroxydopamine-Induced Dopaminergic Neuronal Death and Ferrous Iron Accelerates the conversion of p-Quinone Into Melanin Extracellularly," Journal of Neuroscience Research, 79(6):849-860 (2005).
Jacobo-Molina, A. et al., "cDNA Sequence, Predicted Primary Structure, and Evolving Amphiphilic Helix of Human Aspartyl-tRNA Synthetase," Journal of Biological Chemistry, 264(28):16608-16612 (1989).
Jura, M. et al., "Comprehensive Insight into human aminoacyl-tRNA synthetases as autoantigens in idiopathic inflammatory myopathies," Critical Reviews in Immunology, 27(6):559-572 (2007).
Kapoor, M. et al., "Mutational separation of aminoacylation and cytokine activities of human tyrosyl-tRNA synthetase," Chemistry & Biology, 16(5):531-539 (2009).
Katsumata, Y. et al., "Species-specific immune responses generated by histidyl-tRNA synthetase immunization are associated with muscle and lung inflammation," Journal of Autoimmunity, 29:174-186 (2007).
Katsumata, Y. et al., "Animal models in myositis," Current Opinion in Rheumatology, 20:681-685 (2008).
Kimchi-Sarfaty, C. et al., "A 'Silent' polymorphism in the MDR1 gene changes substrate specificty," Science, 315:525-528 (2007).
Kise, Y. et al., "A short peptide insertion crucial for angiostatic activity of human tryptophanyl-tRNA synthetase," Nature Structural & Molecular Biology, 11(2):149-156 (2004).
Kochendoerfer, G. G., "Site-specific polymer modification of therapeutic proteins," Current Opinion in Chemical Biology, 9:555-560 (2005).

(56) References Cited

OTHER PUBLICATIONS

Kovaleski, B. J. et al.,"In vitro characterization of the interaction between HIV-1 Gag and human lysyl-tRNA synthetase," J. Bio. Chem., 281(28):19449-19456 (2006).
Levine, S. M. et al., "Anti-aminoacyl tRNA synthetase immune responses: insights into the pathogenesis of the idiopathic inflammatory myopathies," Current Opinion in Rheumatology, 15(6):708-713 (2003).
Levine, S. M., et al., "Novel Conformation of Histidyl-Transfer RNA Synthetase in the Lung", Arthritis & Rheumatism, 56(8): 2729-2739, 2007.
Link, A. J. et al., "Discovery of aminoacyl-tRNA synthetase activity through cell-surface display of noncanonical amino acids," Proc. Nat. Acad. Sci., 103(27):10180-10185 (2006).
Lorber, Bernard, et al., "Properties of N-terminal truncated yeast aspartyl-tRNA synthetase and structural characteristics of the cleaved domain," Eur. J. Biochem. 174, pp. 155-161, 1988.
Martin, A. et al., "Epitope studies indicate that histidyl-tRNA synthetase is a stimulating antigen in idiopathic myositis," The FASEB Journal, 9:1226-1233 (1995).
Miller, F. W., et al., "Origin and Regulation of a Disease-specific Autoantibody Response, Antigenic Epitopes, Spectrotype Stability, and Isotype Restriction of Anti-Jo-1 Autoantibodies," J. Clin. Invest., 85:468-475 (1990).
Mirande, M. et al., "Engineering mammalian aspartyl-tRNA synthetase to probe structural features mediating its association with the multisynthetase complex," Eur. J. Biochem., 203(3):459-466 (1992).
Molecular Modeling Database (MMDB), "Solution Structures of the Whep-trs domain of human histidyl-trna synthetase," MMDB ID No. 35920, available for www.ncbi.nlm.nih.gov/Structure/mmdb, accessed Aug. 24, 2012.
Nackley, A. G. et al., "Human Caechol-O-Methyltransferase haplotypes modulate protein expression by altering mRNA secondary structure," Science, 314:1930-1933 (2006).
NCBI Accession No. NP001340, Feb. 27, 2011.
Ngo, J. T. et al., "Computational complexity, protein structure prediction, and the Levinthal paradox," In The Protein Folding Problem and Tertiary Structure Prediction, Merz et al. (ed.), Birkhauser, Boston, MA, pp. 433 and 492-495 (1994).
Nichols, R. C. et al., "Human isoleucyl-tRNA synthetase: sequence of the cDNA, alternative mRNA splicing, and the characteristics of an unusually long C-terminal extension," Gene, 155(2):299-304 (1995).
Nishikai, M. et al., "Heterogeneity of Precipitating Antibodies in Polymyositis and Dermatomyositis," Arthritis and Rheumatism, 23(8):881-888 (1980).
O'Hanlon, T. P. et al., "Genomic organization, transcriptional mapping, and evolutionary implications of the human bi-directional histidyl-tRNA synthetase locus (HARS/HARSL)," Biochemical and Biophysical Research Communications, 294:609-614 (2002).
Oppenheim, J. J. et al., "Autoantigens act as tissue-specific chemoattractants," Journal of Leukocyte Biology, 77:854-861 (2005).
Park, S. G., et al., "Aminoacyl tRNA synthetases and their connections to disease," PNAS, 105(32):11043-11049 (2008).
Park, S. G. et al., "Dose-dependent biphasic activity of tRNA synthetase-associating factor, p43, in angiogenesis," The Journal of Biological Chemistry, 277(47):45243-45248 (2002).
Park, S. G. et al., "Human lysyl-tRNA syntetase is secreted to trigger proinflammatory response," PNAS, 102(18):6356-6361 (2005).
Park, S. G. et al., "Is there an answer? Do aminoacyl-tRNA synthetases have biological functions other than in protein biosynthesis?" IUBMB Life, 58(9):556-558 (2006).
Parker, L. C. et al., "Toll-Like Receptor (TLR)2 and TLR4 Agonists Regulate CCR Expression in Human Monocytic Cells," The Journal of Immunology, 172:4977-4986 (2004).
Pierce, S. B. et al., "Mutations in mitochondrial histidyl tRNA synthetase HARS2 cause ovarian dysgenesis and sensorineural hearing loss of Perrault syndrome," PNAS, 108(16):6543-6548 (2011).
Quesniaux, V. F.J. et al., "Hematopoiesis, including lymphocyte developmet and maturation," Principles of Immunopharmacology, pp. 3-17 (2005).
Raben, N. et al., "A Motif in Human Histidyl-tRNA Synthetase Which is Shared among Several Aminoacyl-tRNA Synthetases is a Coiled-coil That is Essential for Enzymatic Activity and Contains the Major Autoantigenic Epitope," The Journal of Biological Chemistry, 269(39): 24277-24283 (1994).
Reed, V. S. et al., "Characterization of a Novel N-terminal Peptide in Human Aspartyl-tRNA Synthetase," Journal of Biological Chemistry, 269(52):32937-32941 (1994).
Rho, S. B. et al., "Genetic dissection of protein-protein interactions in multi-tRNA synthetase complex," Proc. Natl. Acad. Sci. USA, 96:4488-4493 (1999).
Richardson, R. M. et al., "Role of the cytoplasmic tails of CXCR1 and CXCR2 in mediating leukocyte migration, activation, and regulation," Journal of Immunology, 170(6):2904-2911 (2003).
Sato et al., "Synergy and Cross-Tolerance Between Toll-Like Receptor (TLR) 2- and TLR4-Mediated Signaling Pathways," The Journal of Immunology, 165:7096-7101, 2000.
Sauna, Z. E. et al., "Silent polymorhisms speak: How they affect pharmacogenomics and the treatment of cancer," Cancer Res., 67(20):9609-9612 (2007).
Seburn, K. L. et al., "An active dominant mutation of glycyl-tRNA synthetase causes neuropathy in a Charcot-Marie-Tooth 2D mouse model," Neuron, 51(6):715-726 (2006).
Sen, S. et al., "Developments in directed evolution for improving enzyme functions," Appl. Biochem. Biotechnol., 143:212-223 (2007).
Smith, D. F. et al., "Leukocyte phosphoinositide-3 kinase γ is required for chemokine-induced, sustained adhesion under flow in vivo," Journal of Leukocte Biology, 80(6):1491-1499 (2006).
Soejima, M. et al., "Role of Innate Immunity in a Murine Model of Histidyl-Transfer RNA Snythetase (Jo-1)-Mediated Myositis," Arthritis and Rheumatism, 63(2):479-487 (2011).
Sultan, S. M. et al., "Re-classifiyng myositis," Rheumatology, 49:831-833 (2010).
Tarabishy, A. B. et al., "Retinal Vasculitis Associated with the Anti-Synthetase Syndrome," Ocular Immunology & Inflamation, 18(1):16-18 (2010).
Targoff, I. N., "Update on myositis-specific and myositis-associated autoantibodies," Current Opinion in Rheumatology, 12:475-481 (2000).
Traves, S. L. et al., "Specific CXC but not CC chemokines cause elevated monocyte migration in COPD: a role for $CXCR_2$," Journal of Leukocyte Biology, 76(2):441-450 (2004).
Tsui, H. W. et al., "Transcriptional analyses of the gene region that encodes human histidyl-tRNA sysnthetase: identification of a novel bidirectional regulatory element," Gene, 131:201-208 (1993).
Tzioufas, A. G. et al., "Antisynthetase syndrome," Orphanet Encyclopedia, http://www.orpha.net/data/patho/GB/uk-antisynthetase.pdf, pp. 1-5 Nov. 2001.
Veronese, F. M. et al., "Preface: Introduction and overview of peptide and protein pegylation," Advanced Drug Delivery Reviews, 54:453-456 (2002).
Wakasugi, K. et al., "Two distinct cytokines released from a human aminoacyl-tRNA synthetase," Science, 284:147-151 (1999).
Wakasugi, K. et al., "A human aminoacyl-tRNA synthetase as a regulator of angiogenesis," PNAS USA, 99(1):173-177 (2002).
Wakasugi, K. et al., "Induction of angiogenesis by a frament of human tyrosyl-tRNA synthetase," The Journal of Biological Chemistry, 277(23):20124-20126 (2002).
Wallace, E. A. et al., "Diagnosis and management of inflammatory muscle disease," The Journal of Musculoskeletal Medicine, 27(12):1-7 (2010).
Whisstock, J. C. et al., "Prediction of protein function from protein sequence," Q. Rev. Biophysics., 36(3):307-340 (2003).

(56) References Cited

OTHER PUBLICATIONS

Wishart, M. J. et al., "A single mutation converts a novel phosphotyrosine binding domain into a dual-specificity phosphatase," J. Biol. Chem., 270(45):26782-26785 (1995).

Witkowski, A. et al., "Conversion of β-ketoacyl synthase to a Malonyl Decarboxylase by replacement of the active cysteine with glutamine," Biochemistry, 38:11643-11650 (1999).

Xie, W. et al., "Long-range structural effects of a Charcot-Marie-Tooth disease-causing mutation in human glycyl-tRNA synthetase," PNAS, 104(24):9976-9981 (2007).

Yang, X-L et al., "Crystal structure of a human aminoacyl-tRNA synthetase cytokine," PNAS, 99(24):15369-15374 (2002).

Yang, X-L et al., "Relationship of two human tRNA synthetases used in cell signaling," Trends in Biochemical Sciences, 29(5):250-256 (2004).

Yang, X-L et al., "Gain-of-Function Mutational Activation of Human tRNA Synthetase Procytokine," Chemistry & Biology, 14(12):1323-1333 (2007).

Yousem, S. A. et al., "The pulmonary histopathologic manifestations of the anti-Jo-1 tRNA synthetase syndrome," Modern Pathology, 23:874-880 (2010).

Yu, Y. et al., "Crystal structure of human tryptophanyl-tRNA synthetase catalytic fragment," The Journal of Biological Chemistry, 279(9):8378-8388 (2004).

Zalipsky, S. et al., "Use of functionalized poly(ethylene glycol)s for modification of polypeptides," Polyethylene glycol chemistry: Biotechnical and Biomedical Applications, pp. 347-370, Plenum Press, New York (1992).

Zhou, Q. et al., "Orthogonal use of a human tRNA synthetase active site to achieve multifunctionality," Nature Structural & Molecular Biology, 17(1):57-62 (2010).

Zwijnenburg, P. J. G. et al., B-1426, "Tyrosyl tRNA synthetase is a chemotactic factor in cerebrospinal fluid from patients with bacterial meningitis," Abstracts of the 42nd Interscience Conference on Antimicrobial Agents and Chemotherapy, San Diego, California, Sep. 27-30, 2002, Session 156(B), p. 55.

\* cited by examiner

SEQUENCE LISTING

```
<160> NUMBER OF SEQ ID NOS: 13

<210> SEQ ID NO 1
<211> LENGTH: 685
<212> TYPE: PRT
<213> ORGANISM: Homo sapiens

<400> SEQUENCE: 1

Met Asp Gly Ala Gly Ala Glu Glu Val Leu Ala Pro Leu Arg Leu Ala
1               5                   10                  15

Val Arg Gln Gln Gly Asp Leu Val Arg Lys Leu Lys Glu Asp Lys Ala
                20                  25                  30

Pro Gln Val Asp Val Asp Lys Ala Val Ala Glu Leu Lys Ala Arg Lys
            35                  40                  45

Arg Val Leu Glu Ala Lys Glu Leu Ala Leu Gln Pro Lys Asp Ile
    50                  55                  60

Val Asp Arg Ala Lys Met Glu Asp Thr Leu Lys Arg Arg Phe Phe Tyr
65                  70                  75                  80

Asp Gln Ala Phe Ala Ile Tyr Gly Gly Val Ser Gly Leu Tyr Asp Phe
                85                  90                  95
```

-continued

Gly Pro Val Gly Cys Ala Leu Lys Asn Asn Ile Ile Gln Thr Trp Arg
            100                 105                 110

Gln His Phe Ile Gln Glu Glu Gln Ile Leu Glu Ile Asp Cys Thr Met
            115                 120                 125

Leu Thr Pro Glu Pro Val Leu Lys Thr Ser Gly His Val Asp Lys Phe
130                 135                 140

Ala Asp Phe Met Val Lys Asp Val Lys Asn Gly Glu Cys Phe Arg Ala
145                 150                 155                 160

Asp His Leu Leu Lys Ala His Leu Gln Lys Leu Met Ser Asp Lys Lys
                165                 170                 175

Cys Ser Val Glu Lys Lys Ser Glu Met Glu Ser Val Leu Ala Gln Leu
            180                 185                 190

Asp Asn Tyr Gly Gln Gln Glu Leu Ala Asp Leu Phe Val Asn Tyr Asn
            195                 200                 205

Val Lys Ser Pro Ile Thr Gly Asn Asp Leu Ser Pro Pro Val Ser Phe
            210                 215                 220

Asn Leu Met Phe Lys Thr Phe Ile Gly Pro Gly Asn Met Pro Gly
225                 230                 235                 240

Tyr Leu Arg Pro Glu Thr Ala Gln Gly Ile Phe Leu Asn Phe Lys Arg
                245                 250                 255

Leu Leu Glu Phe Asn Gln Gly Lys Leu Pro Phe Ala Ala Ala Gln Ile
            260                 265                 270

Gly Asn Ser Phe Arg Asn Glu Ile Ser Pro Arg Ser Gly Leu Ile Arg
            275                 280                 285

Val Arg Glu Phe Thr Met Ala Glu Ile Glu His Phe Val Asp Pro Ser
            290                 295                 300

Glu Lys Asp His Pro Lys Phe Gln Asn Val Ala Asp Leu His Leu Tyr
305                 310                 315                 320

Leu Tyr Ser Ala Lys Ala Gln Val Ser Gly Gln Ser Ala Arg Lys Met
                325                 330                 335

Arg Leu Gly Asp Ala Val Glu Gln Gly Val Ile Asn Asn Thr Val Leu
            340                 345                 350

Gly Tyr Phe Ile Gly Arg Ile Tyr Leu Tyr Leu Thr Lys Val Gly Ile
            355                 360                 365

Ser Pro Asp Lys Leu Arg Phe Arg Gln His Met Glu Asn Glu Met Ala
370                 375                 380

His Tyr Ala Cys Asp Cys Trp Asp Ala Glu Ser Lys Thr Ser Tyr Gly
385                 390                 395                 400

Trp Ile Glu Ile Val Gly Cys Ala Asp Arg Ser Cys Tyr Asp Leu Ser
                405                 410                 415

Cys His Ala Arg Ala Thr Lys Val Pro Leu Val Ala Glu Lys Pro Leu
            420                 425                 430

Lys Glu Pro Lys Thr Val Asn Val Val Gln Phe Glu Pro Ser Lys Gly
            435                 440                 445

Ala Ile Gly Lys Ala Tyr Lys Lys Asp Ala Lys Leu Val Met Glu Tyr
            450                 455                 460

Leu Ala Ile Cys Asp Glu Cys Tyr Ile Thr Glu Met Glu Met Leu Leu
465                 470                 475                 480

Asn Glu Lys Gly Glu Phe Thr Ile Glu Thr Glu Gly Lys Thr Phe Gln
                485                 490                 495

Leu Thr Lys Asp Met Ile Asn Val Lys Arg Phe Gln Lys Thr Leu Tyr
            500                 505                 510

Val Glu Glu Val Val Pro Asn Val Ile Glu Pro Ser Phe Gly Leu Gly
            515                 520                 525

Arg Ile Met Tyr Thr Val Phe Glu His Thr Phe His Val Arg Glu Gly
    530                 535                 540

Asp Glu Gln Arg Thr Phe Phe Ser Phe Pro Ala Val Val Ala Pro Phe
545                 550                 555                 560

Lys Cys Ser Val Leu Pro Leu Ser Gln Asn Gln Glu Phe Met Pro Phe
                565                 570                 575

Val Lys Glu Leu Ser Glu Ala Leu Thr Arg His Gly Val Ser His Lys
            580                 585                 590

Val Asp Asp Ser Ser Gly Ser Ile Gly Arg Arg Tyr Ala Arg Thr Asp
            595                 600                 605

Glu Ile Gly Val Ala Phe Gly Val Thr Ile Asp Phe Asp Thr Val Asn
            610                 615                 620

Lys Thr Pro His Thr Ala Thr Leu Arg Asp Arg Asp Ser Met Arg Gln
625                 630                 635                 640

Ile Arg Ala Glu Ile Ser Glu Leu Pro Ser Ile Val Gln Asp Leu Ala
                645                 650                 655

Asn Gly Asn Ile Thr Trp Ala Asp Val Glu Ala Arg Tyr Pro Leu Phe
            660                 665                 670

Glu Gly Gln Glu Thr Gly Lys Lys Glu Thr Ile Glu Glu
            675                 680                 685

<210> SEQ ID NO 2
<211> LENGTH: 501
<212> TYPE: PRT
<213> ORGANISM: Homo sapiens

<400> SEQUENCE: 2

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val Ile Asp Leu Arg Thr Ser Thr Ser
            180                 185                 190

Gln Ala Val Phe Arg Leu Gln Ser Gly Ile Cys His Leu Phe Arg Glu
        195                 200                 205

```
Thr Leu Ile Asn Lys Gly Phe Val Glu Ile Gln Thr Pro Lys Ile Ile
    210                 215                 220
Ser Ala Ala Ser Glu Gly Gly Ala Asn Val Phe Thr Val Ser Tyr Phe
225                 230                 235                 240
Lys Asn Asn Ala Tyr Leu Ala Gln Ser Pro Gln Leu Tyr Lys Gln Met
                245                 250                 255
Cys Ile Cys Ala Asp Phe Glu Lys Val Phe Ser Ile Gly Pro Val Phe
            260                 265                 270
Arg Ala Glu Asp Ser Asn Thr His Arg His Leu Thr Glu Phe Val Gly
        275                 280                 285
Leu Asp Ile Glu Met Ala Phe Asn Tyr His Tyr His Glu Val Met Glu
    290                 295                 300
Glu Ile Ala Asp Thr Met Val Gln Ile Phe Lys Gly Leu Gln Glu Arg
305                 310                 315                 320
Phe Gln Thr Glu Ile Gln Thr Val Asn Lys Gln Phe Pro Cys Glu Pro
                325                 330                 335
Phe Lys Phe Leu Glu Pro Thr Leu Arg Leu Glu Tyr Cys Glu Ala Leu
            340                 345                 350
Ala Met Leu Arg Glu Ala Gly Val Glu Met Gly Asp Glu Asp Asp Leu
        355                 360                 365
Ser Thr Pro Asn Glu Lys Leu Leu Gly His Leu Val Lys Glu Lys Tyr
    370                 375                 380
Asp Thr Asp Phe Tyr Ile Leu Asp Lys Tyr Pro Leu Ala Val Arg Pro
385                 390                 395                 400
Phe Tyr Thr Met Pro Asp Pro Arg Asn Pro Lys Gln Ser Asn Ser Tyr
                405                 410                 415
Asp Met Phe Met Arg Gly Glu Glu Ile Leu Ser Gly Ala Gln Arg Ile
            420                 425                 430
His Asp Pro Gln Leu Leu Thr Glu Arg Ala Leu His His Gly Ile Asp
        435                 440                 445
Leu Glu Lys Ile Lys Ala Tyr Ile Asp Ser Phe Arg Phe Gly Ala Pro
    450                 455                 460
Pro His Ala Gly Gly Gly Ile Gly Leu Glu Arg Val Thr Met Leu Phe
465                 470                 475                 480
Leu Gly Leu His Asn Val Arg Gln Thr Ser Met Phe Pro Arg Asp Pro
                485                 490                 495
Lys Arg Leu Thr Pro
            500

<210> SEQ ID NO 3
<211> LENGTH: 509
<212> TYPE: PRT
<213> ORGANISM: Homo sapiens

<400> SEQUENCE: 3

Met Ala Glu Arg Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
```

```
            65                  70                  75                  80
Ile Arg Cys Phe Lys Arg His Gly Ala Glu Val Ile Asp Thr Pro Val
                     85                  90                  95
Phe Glu Leu Lys Glu Thr Leu Met Gly Lys Tyr Gly Glu Asp Ser Lys
            100                 105                 110
Leu Ile Tyr Asp Leu Lys Asp Gln Gly Gly Leu Leu Ser Leu Arg
            115                 120                 125
Tyr Asp Leu Thr Val Pro Phe Ala Arg Tyr Leu Ala Met Asn Lys Leu
            130                 135                 140
Thr Asn Ile Lys Arg Tyr His Ile Ala Lys Val Tyr Arg Arg Asp Asn
145                 150                 155                 160
Pro Ala Met Thr Arg Gly Arg Tyr Arg Glu Phe Tyr Gln Cys Asp Phe
                     165                 170                 175
Asp Ile Ala Gly Asn Phe Asp Pro Met Ile Pro Asp Ala Glu Cys Leu
            180                 185                 190
Lys Ile Met Cys Glu Ile Leu Ser Ser Leu Gln Ile Gly Asp Phe Leu
            195                 200                 205
Val Lys Val Asn Asp Arg Arg Ile Leu Asp Gly Met Phe Ala Ile Cys
            210                 215                 220
Gly Val Ser Asp Ser Lys Phe Arg Thr Ile Cys Ser Ser Val Asp Lys
225                 230                 235                 240
Leu Asp Lys Val Ser Trp Glu Glu Val Lys Asn Glu Met Val Gly Glu
                     245                 250                 255
Lys Gly Leu Ala Pro Glu Val Ala Asp Arg Ile Gly Asp Tyr Val Gln
            260                 265                 270
Gln His Gly Gly Val Ser Leu Val Glu Gln Leu Leu Gln Asp Pro Lys
            275                 280                 285
Leu Ser Gln Asn Lys Gln Ala Leu Glu Gly Leu Gly Asp Leu Lys Leu
            290                 295                 300
Leu Phe Glu Tyr Leu Thr Leu Phe Gly Ile Asp Asp Lys Ile Ser Phe
305                 310                 315                 320
Asp Leu Ser Leu Ala Arg Gly Leu Asp Tyr Tyr Thr Gly Val Ile Tyr
                     325                 330                 335
Glu Ala Val Leu Leu Gln Thr Pro Ala Gln Ala Gly Glu Glu Pro Leu
            340                 345                 350
Gly Val Gly Ser Val Ala Ala Gly Gly Arg Tyr Asp Gly Leu Val Gly
            355                 360                 365
Met Phe Asp Pro Lys Gly Arg Lys Val Pro Cys Val Gly Leu Ser Ile
370                 375                 380
Gly Val Glu Arg Ile Phe Ser Ile Val Glu Gln Arg Leu Glu Ala Leu
385                 390                 395                 400
Glu Glu Lys Ile Arg Thr Thr Glu Thr Gln Val Leu Val Ala Ser Ala
                     405                 410                 415
Gln Lys Lys Leu Leu Glu Glu Arg Leu Lys Leu Val Ser Glu Leu Trp
            420                 425                 430
Asp Ala Gly Ile Lys Ala Glu Leu Leu Tyr Lys Lys Asn Pro Lys Leu
            435                 440                 445
Leu Asn Gln Leu Gln Tyr Cys Glu Glu Ala Gly Ile Pro Leu Val Ala
            450                 455                 460
Ile Ile Gly Glu Gln Glu Leu Lys Asp Gly Val Ile Lys Leu Arg Ser
465                 470                 475                 480
Val Thr Ser Arg Glu Glu Val Asp Val Arg Arg Glu Asp Leu Val Glu
                     485                 490                 495
```

```
Glu Ile Lys Arg Arg Thr Gly Gln Pro Leu Cys Ile Cys
            500                 505
```

<210> SEQ ID NO 4
<211> LENGTH: 723
<212> TYPE: PRT
<213> ORGANISM: Homo sapiens

<400> SEQUENCE: 4

```
Met Phe Glu Glu Lys Ala Ser Ser Pro Ser Gly Lys Met Gly Gly Glu
1               5                   10                  15

Glu Lys Pro Ile Gly Ala Gly Glu Glu Lys Gln Lys Glu Gly Gly Lys
            20                  25                  30

Lys Lys Asn Lys Glu Gly Ser Gly Asp Gly Gly Arg Ala Glu Leu Asn
        35                  40                  45

Pro Trp Pro Glu Tyr Ile Tyr Thr Arg Leu Glu Met Tyr Asn Ile Leu
    50                  55                  60

Lys Ala Glu His Asp Ser Ile Leu Ala Glu Lys Ala Glu Lys Asp Ser
65                  70                  75                  80

Lys Pro Ile Lys Val Thr Leu Pro Asp Gly Lys Gln Val Asp Ala Glu
                85                  90                  95

Ser Trp Lys Thr Thr Pro Tyr Gln Ile Ala Cys Gly Ile Ser Gln Gly
            100                 105                 110

Leu Ala Asp Asn Thr Val Ile Ala Lys Val Asn Asn Val Val Trp Asp
        115                 120                 125

Leu Asp Arg Pro Leu Glu Glu Asp Cys Thr Leu Glu Leu Leu Lys Phe
    130                 135                 140

Glu Asp Glu Glu Ala Gln Ala Val Tyr Trp His Ser Ser Ala His Ile
145                 150                 155                 160

Met Gly Glu Ala Met Glu Arg Val Tyr Gly Gly Cys Leu Cys Tyr Gly
                165                 170                 175

Pro Pro Ile Glu Asn Gly Phe Tyr Tyr Asp Met Tyr Leu Glu Glu Gly
            180                 185                 190

Gly Val Ser Ser Asn Asp Phe Ser Ser Leu Glu Ala Leu Cys Lys Lys
        195                 200                 205

Ile Ile Lys Glu Lys Gln Ala Phe Glu Arg Leu Glu Val Lys Lys Glu
    210                 215                 220

Thr Leu Leu Ala Met Phe Lys Tyr Asn Lys Phe Lys Cys Arg Ile Leu
225                 230                 235                 240

Asn Glu Lys Val Asn Thr Pro Thr Thr Thr Val Tyr Arg Cys Gly Pro
                245                 250                 255

Leu Ile Asp Leu Cys Arg Gly Pro His Val Arg His Thr Gly Lys Ile
            260                 265                 270

Lys Ala Leu Lys Ile His Lys Asn Ser Ser Thr Tyr Trp Glu Gly Lys
        275                 280                 285

Ala Asp Met Glu Thr Leu Gln Arg Ile Tyr Gly Ile Ser Phe Pro Asp
    290                 295                 300

Pro Lys Met Leu Lys Glu Trp Glu Lys Phe Gln Glu Glu Ala Lys Asn
305                 310                 315                 320

Arg Asp His Arg Lys Ile Gly Arg Asp Gln Glu Leu Tyr Phe Phe His
                325                 330                 335

Glu Leu Ser Pro Gly Ser Cys Phe Phe Leu Pro Lys Gly Ala Tyr Ile
            340                 345                 350

Tyr Asn Ala Leu Ile Glu Phe Ile Arg Ser Glu Tyr Arg Lys Arg Gly
```

```
                355                 360                 365
Phe Gln Glu Val Val Thr Pro Asn Ile Phe Asn Ser Arg Leu Trp Met
370                 375                 380

Thr Ser Gly His Trp Gln His Tyr Ser Glu Asn Met Phe Ser Phe Glu
385                 390                 395                 400

Val Glu Lys Glu Leu Phe Ala Leu Lys Pro Met Asn Cys Pro Gly His
            405                 410                 415

Cys Leu Met Phe Asp His Arg Pro Arg Ser Trp Arg Glu Leu Pro Leu
        420                 425                 430

Arg Leu Ala Asp Phe Gly Val Leu His Arg Asn Glu Leu Ser Gly Ala
435                 440                 445

Leu Thr Gly Leu Thr Arg Val Arg Arg Phe Gln Gln Asp Asp Ala His
450                 455                 460

Ile Phe Cys Ala Met Glu Gln Ile Glu Asp Ile Lys Gly Cys Leu
465                 470                 475                 480

Asp Phe Leu Arg Thr Val Tyr Ser Val Phe Gly Phe Ser Phe Lys Leu
            485                 490                 495

Asn Leu Ser Thr Arg Pro Glu Lys Phe Leu Gly Asp Ile Glu Val Trp
        500                 505                 510

Asp Gln Ala Glu Lys Gln Leu Glu Asn Ser Leu Asn Glu Phe Gly Glu
    515                 520                 525

Lys Trp Glu Leu Asn Ser Gly Asp Gly Ala Phe Tyr Gly Pro Lys Ile
530                 535                 540

Asp Ile Gln Ile Lys Asp Ala Ile Gly Arg Tyr His Gln Cys Ala Thr
545                 550                 555                 560

Ile Gln Leu Asp Phe Gln Leu Pro Ile Arg Phe Asn Leu Thr Tyr Val
            565                 570                 575

Ser His Asp Gly Asp Asp Lys Lys Arg Pro Val Ile Val His Arg Ala
        580                 585                 590

Ile Leu Gly Ser Val Glu Arg Met Ile Ala Ile Leu Thr Glu Asn Tyr
    595                 600                 605

Gly Gly Lys Trp Pro Phe Trp Leu Ser Pro Arg Gln Val Met Val Val
610                 615                 620

Pro Val Gly Pro Thr Cys Asp Glu Tyr Ala Gln Lys Val Arg Gln Gln
625                 630                 635                 640

Phe His Asp Ala Lys Phe Met Ala Asp Ile Asp Leu Asp Pro Gly Cys
            645                 650                 655

Thr Leu Asn Lys Lys Ile Arg Asn Ala Gln Leu Ala Gln Tyr Asn Phe
        660                 665                 670

Ile Leu Val Val Gly Glu Lys Glu Lys Ile Ser Gly Thr Val Asn Ile
    675                 680                 685

Arg Thr Arg Asp Asn Lys Val His Gly Glu Arg Thr Ile Ser Glu Thr
690                 695                 700

Ile Glu Arg Leu Gln Gln Leu Lys Glu Phe Arg Ser Lys Gln Ala Glu
705                 710                 715                 720

Glu Glu Phe

<210> SEQ ID NO 5
<211> LENGTH: 1512
<212> TYPE: PRT
<213> ORGANISM: Homo sapiens

<400> SEQUENCE: 5

Met Ala Thr Leu Ser Leu Thr Val Asn Ser Gly Asp Pro Pro Leu Gly
```

-continued

```
1               5                   10                  15
Ala Leu Leu Ala Val Glu His Val Lys Asp Val Ser Ile Ser Val
            20                  25                  30
Glu Glu Gly Lys Glu Asn Ile Leu His Val Ser Glu Asn Val Ile Phe
            35                  40                  45
Thr Asp Val Asn Ser Ile Leu Arg Tyr Leu Ala Arg Val Ala Thr Thr
            50                  55                  60
Ala Gly Leu Tyr Gly Ser Asn Leu Met Glu His Thr Glu Ile Asp His
65                  70                  75                  80
Trp Leu Glu Phe Ser Ala Thr Lys Leu Ser Ser Cys Asp Ser Phe Thr
                85                  90                  95
Ser Thr Ile Asn Glu Leu Asn His Cys Leu Ser Leu Arg Thr Tyr Leu
            100                 105                 110
Val Gly Asn Ser Leu Ser Leu Ala Asp Leu Cys Val Trp Ala Thr Leu
            115                 120                 125
Lys Gly Asn Ala Ala Trp Gln Glu Gln Leu Lys Gln Lys Lys Ala Pro
130                 135                 140
Val His Val Lys Arg Trp Phe Gly Phe Leu Glu Ala Gln Gln Ala Phe
145                 150                 155                 160
Gln Ser Val Gly Thr Lys Trp Asp Val Ser Thr Lys Ala Arg Val
                165                 170                 175
Ala Pro Glu Lys Lys Gln Asp Val Gly Lys Phe Val Glu Leu Pro Gly
            180                 185                 190
Ala Glu Met Gly Lys Val Thr Val Arg Phe Pro Pro Glu Ala Ser Gly
            195                 200                 205
Tyr Leu His Ile Gly His Ala Lys Ala Ala Leu Leu Asn Gln His Tyr
210                 215                 220
Gln Val Asn Phe Lys Gly Lys Leu Ile Met Arg Phe Asp Thr Asn
225                 230                 235                 240
Pro Glu Lys Glu Lys Glu Asp Phe Glu Lys Val Ile Leu Glu Asp Val
                245                 250                 255
Ala Met Leu His Ile Lys Pro Asp Gln Phe Thr Tyr Thr Ser Asp His
            260                 265                 270
Phe Glu Thr Ile Met Lys Tyr Ala Glu Lys Leu Ile Gln Glu Gly Lys
            275                 280                 285
Ala Tyr Val Asp Asp Thr Pro Ala Glu Gln Met Lys Ala Glu Arg Glu
            290                 295                 300
Gln Arg Ile Glu Ser Lys His Arg Lys Asn Pro Ile Glu Lys Asn Leu
305                 310                 315                 320
Gln Met Trp Glu Glu Met Lys Lys Gly Ser Gln Phe Gly His Ser Cys
                325                 330                 335
Cys Leu Arg Ala Lys Ile Asp Met Ser Ser Asn Gly Cys Met Arg
            340                 345                 350
Asp Pro Thr Leu Tyr Arg Cys Lys Ile Gln Pro His Pro Arg Thr Gly
            355                 360                 365
Asn Lys Tyr Asn Val Tyr Pro Thr Tyr Asp Phe Ala Cys Pro Ile Val
370                 375                 380
Asp Ser Ile Glu Gly Val Thr His Ala Leu Arg Thr Thr Glu Tyr His
385                 390                 395                 400
Asp Arg Asp Glu Gln Phe Tyr Trp Ile Ile Glu Ala Leu Gly Ile Arg
                405                 410                 415
Lys Pro Tyr Ile Trp Glu Tyr Ser Arg Leu Asn Leu Asn Asn Thr Val
            420                 425                 430
```

```
Leu Ser Lys Arg Lys Leu Thr Trp Phe Val Asn Glu Gly Leu Val Asp
    435                 440                 445

Gly Trp Asp Asp Pro Arg Phe Pro Thr Val Arg Gly Val Leu Arg Arg
    450                 455                 460

Gly Met Thr Val Glu Gly Leu Lys Gln Phe Ile Ala Ala Gln Gly Ser
465                 470                 475                 480

Ser Arg Ser Val Val Asn Met Glu Trp Asp Lys Ile Trp Ala Phe Asn
                485                 490                 495

Lys Lys Val Ile Asp Pro Val Ala Pro Arg Tyr Val Ala Leu Leu Lys
                500                 505                 510

Lys Glu Val Ile Pro Val Asn Val Pro Glu Ala Gln Glu Glu Met Lys
                515                 520                 525

Glu Val Ala Lys His Pro Lys Asn Pro Glu Val Gly Leu Lys Pro Val
                530                 535                 540

Trp Tyr Ser Pro Lys Val Phe Ile Glu Gly Ala Asp Ala Glu Thr Phe
545                 550                 555                 560

Ser Glu Gly Glu Met Val Thr Phe Ile Asn Trp Gly Asn Leu Asn Ile
                565                 570                 575

Thr Lys Ile His Lys Asn Ala Asp Gly Lys Ile Ile Ser Leu Asp Ala
                580                 585                 590

Lys Phe Asn Leu Glu Asn Lys Asp Tyr Lys Lys Thr Thr Lys Val Thr
                595                 600                 605

Trp Leu Ala Glu Thr Thr His Ala Leu Pro Ile Pro Val Ile Cys Val
    610                 615                 620

Thr Tyr Glu His Leu Ile Thr Lys Pro Val Leu Gly Lys Asp Glu Asp
625                 630                 635                 640

Phe Lys Gln Tyr Val Asn Lys Asn Ser Lys His Glu Glu Leu Met Leu
                645                 650                 655

Gly Asp Pro Cys Leu Lys Asp Leu Lys Lys Gly Asp Ile Ile Gln Leu
                660                 665                 670

Gln Arg Arg Gly Phe Phe Ile Cys Asp Gln Pro Tyr Glu Pro Val Ser
    675                 680                 685

Pro Tyr Ser Cys Lys Glu Ala Pro Cys Val Leu Ile Tyr Ile Pro Asp
    690                 695                 700

Gly His Thr Lys Glu Met Pro Thr Ser Gly Ser Lys Glu Lys Thr Lys
705                 710                 715                 720

Val Glu Ala Thr Lys Asn Glu Thr Ser Ala Pro Phe Lys Glu Arg Pro
                725                 730                 735

Thr Pro Ser Leu Asn Asn Asn Cys Thr Thr Ser Glu Asp Ser Leu Val
                740                 745                 750

Leu Tyr Asn Arg Val Ala Val Gln Gly Asp Val Val Arg Glu Leu Lys
                755                 760                 765

Ala Lys Lys Ala Pro Lys Glu Asp Val Asp Ala Val Lys Gln Leu
                770                 775                 780

Leu Ser Leu Lys Ala Glu Tyr Lys Glu Lys Thr Gly Gln Glu Tyr Lys
785                 790                 795                 800

Pro Gly Asn Pro Pro Ala Glu Ile Gly Gln Asn Ile Ser Ser Asn Ser
                805                 810                 815

Ser Ala Ser Ile Leu Glu Ser Lys Ser Leu Tyr Asp Glu Val Ala Ala
                820                 825                 830

Gln Gly Glu Val Val Arg Lys Leu Lys Ala Glu Lys Ser Pro Lys Ala
                835                 840                 845
```

```
Lys Ile Asn Glu Ala Val Glu Cys Leu Leu Ser Leu Lys Ala Gln Tyr
850                 855                 860

Lys Glu Lys Thr Gly Lys Glu Tyr Ile Pro Gly Gln Pro Pro Leu Ser
865                 870                 875                 880

Gln Ser Ser Asp Ser Ser Pro Thr Arg Asn Ser Glu Pro Ala Gly Leu
                885                 890                 895

Glu Thr Pro Glu Ala Lys Val Leu Phe Asp Lys Val Ala Ser Gln Gly
            900                 905                 910

Glu Val Val Arg Lys Leu Lys Thr Glu Lys Ala Pro Lys Asp Gln Val
        915                 920                 925

Asp Ile Ala Val Gln Glu Leu Leu Gln Leu Lys Ala Gln Tyr Lys Ser
930                 935                 940

Leu Ile Gly Val Glu Tyr Lys Pro Val Ser Ala Thr Gly Ala Glu Asp
945                 950                 955                 960

Lys Asp Lys Lys Lys Lys Glu Lys Glu Asn Lys Ser Glu Lys Gln Asn
                965                 970                 975

Lys Pro Gln Lys Gln Asn Asp Gly Gln Arg Lys Asp Pro Ser Lys Asn
            980                 985                 990

Gln Gly Gly Gly Leu Ser Ser Ser  Gly Ala Gly Glu Gly  Gln Gly Pro
            995                 1000                 1005

Lys Lys  Gln Thr Arg Leu Gly  Leu Glu Ala Lys Lys  Glu Glu Asn
    1010                 1015                 1020

Leu Ala  Asp Trp Tyr Ser Gln  Val Ile Thr Lys Ser  Glu Met Ile
    1025                 1030                 1035

Glu Tyr  His Asp Ile Ser Gly  Cys Tyr Ile Leu Arg  Pro Trp Ala
    1040                 1045                 1050

Tyr Ala  Ile Trp Glu Ala Ile  Lys Asp Phe Phe Asp  Ala Glu Ile
    1055                 1060                 1065

Lys Lys  Leu Gly Val Glu Asn  Cys Tyr Phe Pro Met  Phe Val Ser
    1070                 1075                 1080

Gln Ser  Ala Leu Glu Lys Glu  Lys Thr His Val Ala  Asp Phe Ala
    1085                 1090                 1095

Pro Glu  Val Ala Trp Val Thr  Arg Ser Gly Lys Thr  Glu Leu Ala
    1100                 1105                 1110

Glu Pro  Ile Ala Ile Arg Pro  Thr Ser Glu Thr Val  Met Tyr Pro
    1115                 1120                 1125

Ala Tyr  Ala Lys Trp Val Gln  Ser His Arg Asp Leu  Pro Ile Lys
    1130                 1135                 1140

Leu Asn  Gln Trp Cys Asn Val  Val Arg Trp Glu Phe  Lys His Pro
    1145                 1150                 1155

Gln Pro  Phe Leu Arg Thr Arg  Glu Phe Leu Trp Gln  Glu Gly His
    1160                 1165                 1170

Ser Ala  Phe Ala Thr Met Glu  Glu Ala Ala Glu Glu  Val Leu Gln
    1175                 1180                 1185

Ile Leu  Asp Leu Tyr Ala Gln  Val Tyr Glu Glu Leu  Leu Ala Ile
    1190                 1195                 1200

Pro Val  Val Lys Gly Arg Lys  Thr Glu Lys Glu Lys  Phe Ala Gly
    1205                 1210                 1215

Gly Asp  Tyr Thr Thr Thr Ile  Glu Ala Phe Ile Ser  Ala Ser Gly
    1220                 1225                 1230

Arg Ala  Ile Gln Gly Gly Thr  Ser His His Leu Gly  Gln Asn Phe
    1235                 1240                 1245

Ser Lys  Met Phe Glu Ile Val  Phe Glu Asp Pro Lys  Ile Pro Gly
```

```
                    1250                1255                1260
Glu Lys Gln Phe Ala Tyr Gln Asn Ser Trp Gly Leu Thr Thr Arg
    1265                1270                1275
Thr Ile Gly Val Met Thr Met Val His Gly Asp Asn Met Gly Leu
    1280                1285                1290
Val Leu Pro Pro Arg Val Ala Cys Val Gln Val Ile Ile Pro
    1295                1300                1305
Cys Gly Ile Thr Asn Ala Leu Ser Glu Glu Asp Lys Glu Ala Leu
    1310                1315                1320
Ile Ala Lys Cys Asn Asp Tyr Arg Arg Arg Leu Leu Ser Val Asn
    1325                1330                1335
Ile Arg Val Arg Ala Asp Leu Arg Asp Asn Tyr Ser Pro Gly Trp
    1340                1345                1350
Lys Phe Asn His Trp Glu Leu Lys Gly Val Pro Ile Arg Leu Glu
    1355                1360                1365
Val Gly Pro Arg Asp Met Lys Ser Cys Gln Phe Val Ala Val Arg
    1370                1375                1380
Arg Asp Thr Gly Glu Lys Leu Thr Val Ala Glu Asn Glu Ala Glu
    1385                1390                1395
Thr Lys Leu Gln Ala Ile Leu Glu Asp Ile Gln Val Thr Leu Phe
    1400                1405                1410
Thr Arg Ala Ser Glu Asp Leu Lys Thr His Met Val Val Ala Asn
    1415                1420                1425
Thr Met Glu Asp Phe Gln Lys Ile Leu Asp Ser Gly Lys Ile Val
    1430                1435                1440
Gln Ile Pro Phe Cys Gly Glu Ile Asp Cys Glu Asp Trp Ile Lys
    1445                1450                1455
Lys Thr Thr Ala Arg Asp Gln Asp Leu Glu Pro Gly Ala Pro Ser
    1460                1465                1470
Met Gly Ala Lys Ser Leu Cys Ile Pro Phe Lys Pro Leu Cys Glu
    1475                1480                1485
Leu Gln Pro Gly Ala Lys Cys Val Cys Gly Lys Asn Pro Ala Lys
    1490                1495                1500
Tyr Tyr Thr Leu Phe Gly Arg Ser Tyr
    1505                1510

<210> SEQ ID NO 6
<211> LENGTH: 514
<212> TYPE: PRT
<213> ORGANISM: Homo sapiens

<400> SEQUENCE: 6

Met Val Leu Asp Leu Asp Leu Phe Arg Val Lys Gly Gly Asp Pro
1               5                   10                  15

Ala Leu Ile Arg Glu Thr Gln Glu Lys Arg Phe Lys Asp Pro Gly Leu
                20                  25                  30

Val Asp Gln Leu Val Lys Ala Asp Ser Glu Trp Arg Arg Cys Arg Phe
            35                  40                  45

Arg Ala Asp Asn Leu Asn Lys Leu Lys Asn Leu Cys Ser Lys Thr Ile
        50                  55                  60

Gly Glu Lys Met Lys Lys Lys Glu Pro Val Gly Asp Asp Glu Ser Val
65                  70                  75                  80

Pro Glu Asn Val Leu Ser Phe Asp Asp Leu Thr Ala Asp Ala Leu Ala
                85                  90                  95
```

```
Asn Leu Lys Val Ser Gln Ile Lys Lys Val Arg Leu Leu Ile Asp Glu
             100                 105                 110

Ala Ile Leu Lys Cys Asp Ala Glu Arg Ile Lys Leu Glu Ala Glu Arg
         115                 120                 125

Phe Glu Asn Leu Arg Glu Ile Gly Asn Leu Leu His Pro Ser Val Pro
     130                 135                 140

Ile Ser Asn Asp Glu Asp Val Asp Asn Lys Val Glu Arg Ile Trp Gly
145                 150                 155                 160

Asp Cys Thr Val Arg Lys Lys Tyr Ser His Val Asp Leu Val Val Met
                 165                 170                 175

Val Asp Gly Phe Glu Gly Glu Lys Gly Ala Val Val Ala Gly Ser Arg
             180                 185                 190

Gly Tyr Phe Leu Lys Gly Val Leu Val Phe Leu Glu Gln Ala Leu Ile
         195                 200                 205

Gln Tyr Ala Leu Arg Thr Leu Gly Ser Arg Gly Tyr Ile Pro Ile Tyr
     210                 215                 220

Thr Pro Phe Phe Met Arg Lys Glu Val Met Gln Glu Val Ala Gln Leu
225                 230                 235                 240

Ser Gln Phe Asp Glu Glu Leu Tyr Lys Val Ile Gly Lys Gly Ser Glu
                 245                 250                 255

Lys Ser Asp Asp Asn Ser Tyr Asp Glu Lys Tyr Leu Ile Ala Thr Ser
             260                 265                 270

Glu Gln Pro Ile Ala Ala Leu His Arg Asp Glu Trp Leu Arg Pro Glu
         275                 280                 285

Asp Leu Pro Ile Lys Tyr Ala Gly Leu Ser Thr Cys Phe Arg Gln Glu
     290                 295                 300

Val Gly Ser His Gly Arg Asp Thr Arg Gly Ile Phe Arg Val His Gln
305                 310                 315                 320

Phe Glu Lys Ile Glu Gln Phe Val Tyr Ser Ser Pro His Asp Asn Lys
                 325                 330                 335

Ser Trp Glu Met Phe Glu Met Ile Thr Thr Ala Glu Glu Phe Tyr
             340                 345                 350

Gln Ser Leu Gly Ile Pro Tyr His Ile Val Asn Ile Val Ser Gly Ser
         355                 360                 365

Leu Asn His Ala Ala Ser Lys Lys Leu Asp Leu Glu Ala Trp Phe Pro
     370                 375                 380

Gly Ser Gly Ala Phe Arg Glu Leu Val Ser Cys Ser Asn Cys Thr Asp
385                 390                 395                 400

Tyr Gln Ala Arg Arg Leu Arg Ile Arg Tyr Gly Gln Thr Lys Lys Met
                 405                 410                 415

Met Asp Lys Val Glu Phe Val His Met Leu Asn Ala Thr Met Cys Ala
             420                 425                 430

Thr Thr Cys Thr Ile Cys Ala Ile Leu Glu Asn Tyr Gln Thr Glu Lys
         435                 440                 445

Gly Ile Thr Val Pro Glu Lys Leu Lys Glu Phe Met Pro Pro Gly Leu
     450                 455                 460

Gln Glu Leu Ile Pro Phe Val Lys Pro Ala Pro Ile Glu Gln Glu Pro
465                 470                 475                 480

Ser Lys Lys Gln Lys Gln His Glu Gly Ser Lys Lys Ala Ala
                 485                 490                 495

Ala Arg Asp Val Thr Leu Glu Asn Arg Leu Gln Asn Met Glu Val Thr
             500                 505                 510

Asp Ala
```

<210> SEQ ID NO 7
<211> LENGTH: 508
<212> TYPE: PRT
<213> ORGANISM: Homo sapiens

<400> SEQUENCE: 7

```
Met Ala Asp Gly Gln Val Ala Glu Leu Leu Arg Arg Leu Glu Ala
1               5                   10                  15

Ser Asp Gly Gly Leu Asp Ser Ala Glu Leu Ala Ala Glu Leu Gly Met
                20                  25                  30

Glu His Gln Ala Val Val Gly Ala Val Lys Ser Leu Gln Ala Leu Gly
            35                  40                  45

Glu Val Ile Glu Ala Glu Leu Arg Ser Thr Lys His Trp Glu Leu Thr
        50                  55                  60

Ala Glu Gly Glu Glu Ile Ala Arg Glu Gly Ser His Glu Ala Arg Val
65                  70                  75                  80

Phe Arg Ser Ile Pro Pro Glu Gly Leu Ala Gln Ser Glu Leu Met Arg
                85                  90                  95

Leu Pro Ser Gly Lys Val Gly Phe Ser Lys Ala Met Ser Asn Lys Trp
                100                 105                 110

Ile Arg Val Asp Lys Ser Ala Ala Asp Gly Pro Arg Val Phe Arg Val
            115                 120                 125

Val Asp Ser Met Glu Asp Glu Val Gln Arg Arg Leu Gln Leu Val Arg
        130                 135                 140

Gly Gly Gln Ala Glu Lys Leu Gly Glu Lys Glu Arg Ser Glu Leu Arg
145                 150                 155                 160

Lys Arg Lys Leu Leu Ala Glu Val Thr Leu Lys Thr Tyr Trp Val Ser
                165                 170                 175

Lys Gly Ser Ala Phe Ser Thr Ser Ile Ser Lys Gln Glu Thr Glu Leu
                180                 185                 190

Ser Pro Glu Met Ile Ser Ser Gly Ser Trp Arg Asp Arg Pro Phe Lys
            195                 200                 205

Pro Tyr Asn Phe Leu Ala His Gly Val Leu Pro Asp Ser Gly His Leu
        210                 215                 220

His Pro Leu Leu Lys Val Arg Ser Gln Phe Arg Gln Ile Phe Leu Glu
225                 230                 235                 240

Met Gly Phe Thr Glu Met Pro Thr Asp Asn Phe Ile Glu Ser Ser Phe
                245                 250                 255

Trp Asn Phe Asp Ala Leu Phe Gln Pro Gln Gln His Pro Ala Arg Asp
                260                 265                 270

Gln His Asp Thr Phe Phe Leu Arg Asp Pro Ala Glu Ala Leu Gln Leu
            275                 280                 285

Pro Met Asp Tyr Val Gln Arg Val Lys Arg Thr His Ser Gln Gly Gly
        290                 295                 300

Tyr Gly Ser Gln Gly Tyr Lys Tyr Asn Trp Lys Leu Asp Glu Ala Arg
305                 310                 315                 320

Lys Asn Leu Leu Arg Thr His Thr Thr Ser Ala Ser Ala Arg Ala Leu
                325                 330                 335

Tyr Arg Leu Ala Gln Lys Lys Pro Phe Thr Pro Val Lys Tyr Phe Ser
                340                 345                 350

Ile Asp Arg Val Phe Arg Asn Glu Thr Leu Asp Ala Thr His Leu Ala
            355                 360                 365

Glu Phe His Gln Ile Glu Gly Val Val Ala Asp His Gly Leu Thr Leu
```

```
                    370                 375                 380
Gly His Leu Met Gly Val Leu Arg Glu Phe Phe Thr Lys Leu Gly Ile
385                 390                 395                 400

Thr Gln Leu Arg Phe Lys Pro Ala Tyr Asn Pro Tyr Thr Glu Pro Ser
                    405                 410                 415

Met Glu Val Phe Ser Tyr His Gln Gly Leu Lys Lys Trp Val Glu Val
                    420                 425                 430

Gly Asn Ser Gly Val Phe Arg Pro Glu Met Leu Leu Pro Met Gly Leu
                435                 440                 445

Pro Glu Asn Val Ser Val Ile Ala Trp Gly Leu Ser Leu Glu Arg Pro
450                 455                 460

Thr Met Ile Lys Tyr Gly Ile Asn Asn Ile Arg Glu Leu Val Gly His
465                 470                 475                 480

Lys Val Asn Leu Gln Met Val Tyr Asp Ser Pro Leu Cys Arg Leu Asp
                485                 490                 495

Ala Glu Pro Arg Pro Pro Pro Thr Gln Glu Ala Ala
                500                 505

<210> SEQ ID NO 8
<211> LENGTH: 597
<212> TYPE: PRT
<213> ORGANISM: Homo sapiens

<400> SEQUENCE: 8

Met Ala Ala Val Gln Ala Ala Glu Val Lys Val Asp Gly Ser Glu Pro
1               5                   10                  15

Lys Leu Ser Lys Asn Glu Leu Lys Arg Arg Leu Lys Ala Glu Lys Lys
                20                  25                  30

Val Ala Glu Lys Glu Ala Lys Gln Lys Glu Leu Ser Glu Lys Gln Leu
            35                  40                  45

Ser Gln Ala Thr Ala Ala Thr Asn His Thr Thr Asp Asn Gly Val
        50                  55                  60

Gly Pro Glu Glu Glu Ser Val Asp Pro Asn Gln Tyr Tyr Lys Ile Arg
65                  70                  75                  80

Ser Gln Ala Ile His Gln Leu Lys Val Asn Gly Glu Asp Pro Tyr Pro
                85                  90                  95

His Lys Phe His Val Asp Ile Ser Leu Thr Asp Phe Ile Gln Lys Tyr
                100                 105                 110

Ser His Leu Gln Pro Gly Asp His Leu Thr Asp Ile Thr Leu Lys Val
            115                 120                 125

Ala Gly Arg Ile His Ala Lys Arg Ala Ser Gly Gly Lys Leu Ile Phe
        130                 135                 140

Tyr Asp Leu Arg Gly Glu Gly Val Lys Leu Gln Val Met Ala Asn Ser
145                 150                 155                 160

Arg Asn Tyr Lys Ser Glu Glu Glu Phe Ile His Ile Asn Asn Lys Leu
                165                 170                 175

Arg Arg Gly Asp Ile Ile Gly Val Gln Gly Asn Pro Gly Lys Thr Lys
                180                 185                 190

Lys Gly Glu Leu Ser Ile Ile Pro Tyr Glu Ile Thr Leu Leu Ser Pro
            195                 200                 205

Cys Leu His Met Leu Pro His Leu His Phe Gly Leu Lys Asp Lys Glu
        210                 215                 220

Thr Arg Tyr Arg Gln Arg Tyr Leu Asp Leu Ile Leu Asn Asp Phe Val
225                 230                 235                 240
```

```
Arg Gln Lys Phe Ile Ile Arg Ser Lys Ile Thr Tyr Ile Arg Ser
                245                 250                 255

Phe Leu Asp Glu Leu Gly Phe Leu Glu Ile Glu Thr Pro Met Met Asn
            260                 265                 270

Ile Ile Pro Gly Gly Ala Val Ala Lys Pro Phe Ile Thr Tyr His Asn
        275                 280                 285

Glu Leu Asp Met Asn Leu Tyr Met Arg Ile Ala Pro Glu Leu Tyr His
    290                 295                 300

Lys Met Leu Val Val Gly Gly Ile Asp Arg Val Tyr Glu Ile Gly Arg
305                 310                 315                 320

Gln Phe Arg Asn Glu Gly Ile Asp Leu Thr His Asn Pro Glu Phe Thr
                325                 330                 335

Thr Cys Glu Phe Tyr Met Ala Tyr Ala Asp Tyr His Asp Leu Met Glu
            340                 345                 350

Ile Thr Glu Lys Met Val Ser Gly Met Val Lys His Ile Thr Gly Ser
        355                 360                 365

Tyr Lys Val Thr Tyr His Pro Asp Gly Pro Glu Gly Gln Ala Tyr Asp
    370                 375                 380

Val Asp Phe Thr Pro Pro Phe Arg Arg Ile Asn Met Val Glu Glu Leu
385                 390                 395                 400

Glu Lys Ala Leu Gly Met Lys Leu Pro Glu Thr Asn Leu Phe Glu Thr
                405                 410                 415

Glu Glu Thr Arg Lys Ile Leu Asp Asp Ile Cys Val Ala Lys Ala Val
            420                 425                 430

Glu Cys Pro Pro Pro Arg Thr Thr Ala Arg Leu Leu Asp Lys Leu Val
        435                 440                 445

Gly Glu Phe Leu Glu Val Thr Cys Ile Asn Pro Thr Phe Ile Cys Asp
    450                 455                 460

His Pro Gln Ile Met Ser Pro Leu Ala Lys Trp His Arg Ser Lys Glu
465                 470                 475                 480

Gly Leu Thr Glu Arg Phe Glu Leu Phe Val Met Lys Lys Glu Ile Cys
                485                 490                 495

Asn Ala Tyr Thr Glu Leu Asn Asp Pro Met Arg Gln Arg Gln Leu Phe
            500                 505                 510

Glu Glu Gln Ala Lys Ala Lys Ala Ala Gly Asp Asp Glu Ala Met Phe
        515                 520                 525

Ile Asp Glu Asn Phe Cys Thr Ala Leu Glu Tyr Gly Leu Pro Pro Thr
    530                 535                 540

Ala Gly Trp Gly Met Gly Ile Asp Arg Val Ala Met Phe Leu Thr Asp
545                 550                 555                 560

Ser Asn Asn Ile Lys Glu Val Leu Leu Phe Pro Ala Met Lys Pro Glu
                565                 570                 575

Asp Lys Lys Glu Asn Val Ala Thr Thr Asp Thr Leu Glu Ser Thr Thr
            580                 585                 590

Val Gly Thr Ser Val
        595

<210> SEQ ID NO 9
<211> LENGTH: 548
<212> TYPE: PRT
<213> ORGANISM: Homo sapiens

<400> SEQUENCE: 9

Met Val Leu Ala Glu Leu Tyr Val Ser Asp Arg Glu Gly Ser Asp Ala
1               5                   10                  15
```

```
Thr Gly Asp Gly Thr Lys Glu Lys Pro Phe Lys Thr Gly Leu Lys Ala
            20                  25                  30

Leu Met Thr Val Gly Lys Glu Pro Phe Pro Thr Ile Tyr Val Asp Ser
        35                  40                  45

Gln Lys Glu Asn Glu Arg Trp Asn Val Ile Ser Lys Ser Gln Leu Lys
    50                  55                  60

Asn Ile Lys Lys Met Trp His Arg Glu Gln Met Lys Ser Glu Ser Arg
65                  70                  75                  80

Glu Lys Lys Glu Ala Glu Asp Ser Leu Arg Arg Glu Lys Asn Leu Glu
                85                  90                  95

Glu Ala Lys Lys Ile Thr Ile Lys Asn Asp Pro Ser Leu Pro Glu Pro
            100                 105                 110

Lys Cys Val Lys Ile Gly Ala Leu Glu Gly Tyr Arg Gly Gln Arg Val
        115                 120                 125

Lys Val Phe Gly Trp Val His Arg Leu Arg Arg Gln Gly Lys Asn Leu
    130                 135                 140

Met Phe Leu Val Leu Arg Asp Gly Thr Gly Tyr Leu Gln Cys Val Leu
145                 150                 155                 160

Ala Asp Glu Leu Cys Gln Cys Tyr Asn Gly Val Leu Leu Ser Thr Glu
                165                 170                 175

Ser Ser Val Ala Val Tyr Gly Met Leu Asn Leu Thr Pro Lys Gly Lys
            180                 185                 190

Gln Ala Pro Gly Gly His Glu Leu Ser Cys Asp Phe Trp Glu Leu Ile
        195                 200                 205

Gly Leu Ala Pro Ala Gly Gly Ala Asp Asn Leu Ile Asn Glu Glu Ser
    210                 215                 220

Asp Val Asp Val Gln Leu Asn Asn Arg His Met Met Ile Arg Gly Glu
225                 230                 235                 240

Asn Met Ser Lys Ile Leu Lys Ala Arg Ser Met Val Thr Arg Cys Phe
                245                 250                 255

Arg Asp His Phe Phe Asp Arg Gly Tyr Tyr Glu Val Thr Pro Pro Thr
            260                 265                 270

Leu Val Gln Thr Gln Val Glu Gly Gly Ala Thr Leu Phe Lys Leu Asp
        275                 280                 285

Tyr Phe Gly Glu Glu Ala Phe Leu Thr Gln Ser Ser Gln Leu Tyr Leu
    290                 295                 300

Glu Thr Cys Leu Pro Ala Leu Gly Asp Val Phe Cys Ile Ala Gln Ser
305                 310                 315                 320

Tyr Arg Ala Glu Gln Ser Arg Thr Arg Arg His Leu Ala Glu Tyr Thr
                325                 330                 335

His Val Glu Ala Glu Cys Pro Phe Leu Thr Phe Asp Asp Leu Leu Asn
            340                 345                 350

Arg Leu Glu Asp Leu Val Cys Asp Val Val Asp Arg Ile Leu Lys Ser
        355                 360                 365

Pro Ala Gly Ser Ile Val His Glu Leu Asn Pro Asn Phe Gln Pro Pro
    370                 375                 380

Lys Arg Pro Phe Lys Arg Met Asn Tyr Ser Asp Ala Ile Val Trp Leu
385                 390                 395                 400

Lys Glu His Asp Val Lys Lys Glu Asp Gly Thr Phe Tyr Glu Phe Gly
                405                 410                 415

Glu Asp Ile Pro Glu Ala Pro Glu Arg Leu Met Thr Asp Thr Ile Asn
            420                 425                 430
```

```
Glu Pro Ile Leu Leu Cys Arg Phe Pro Val Glu Ile Lys Ser Phe Tyr
                435                 440                 445

Met Gln Arg Cys Pro Glu Asp Ser Arg Leu Thr Glu Ser Val Asp Val
450                 455                 460

Leu Met Pro Asn Val Gly Glu Ile Val Gly Gly Ser Met Arg Ile Phe
465                 470                 475                 480

Asp Ser Glu Glu Ile Leu Ala Gly Tyr Lys Arg Gly Ile Asp Pro
                485                 490                 495

Thr Pro Tyr Tyr Trp Tyr Thr Asp Gln Arg Lys Tyr Gly Thr Cys Pro
                500                 505                 510

His Gly Gly Tyr Gly Leu Gly Leu Glu Arg Phe Leu Thr Trp Ile Leu
                515                 520                 525

Asn Arg Tyr His Ile Arg Asp Val Cys Leu Tyr Pro Arg Phe Val Gln
                530                 535                 540

Arg Cys Thr Pro
545

<210> SEQ ID NO 10
<211> LENGTH: 968
<212> TYPE: PRT
<213> ORGANISM: Homo sapiens

<400> SEQUENCE: 10

Met Asp Ser Thr Leu Thr Ala Ser Glu Ile Arg Gln Arg Phe Ile Asp
1               5                   10                  15

Phe Phe Lys Arg Asn Glu His Thr Tyr Val His Ser Ser Ala Thr Ile
                20                  25                  30

Pro Leu Asp Asp Pro Thr Leu Leu Phe Ala Asn Ala Gly Met Asn Gln
                35                  40                  45

Phe Lys Pro Ile Phe Leu Asn Thr Ile Asp Pro Ser His Pro Met Ala
    50                  55                  60

Lys Leu Ser Arg Ala Ala Asn Thr Gln Lys Cys Ile Arg Ala Gly Gly
65              70                  75                  80

Lys His Asn Asp Leu Asp Asp Val Gly Lys Asp Val Tyr His His Thr
                85                  90                  95

Phe Phe Glu Met Leu Gly Ser Trp Ser Phe Gly Asp Tyr Phe Lys Glu
                100                 105                 110

Leu Ala Cys Lys Met Ala Leu Glu Leu Leu Thr Gln Glu Phe Gly Ile
                115                 120                 125

Pro Ile Glu Arg Leu Tyr Val Thr Tyr Phe Gly Gly Asp Glu Ala Ala
    130                 135                 140

Gly Leu Glu Ala Asp Leu Glu Cys Lys Gln Ile Trp Gln Asn Leu Gly
145                 150                 155                 160

Leu Asp Asp Thr Lys Ile Leu Pro Gly Asn Met Lys Asp Asn Phe Trp
                165                 170                 175

Glu Met Gly Asp Thr Gly Pro Cys Gly Pro Cys Ser Glu Ile His Tyr
                180                 185                 190

Asp Arg Ile Gly Gly Arg Asp Ala Ala His Leu Val Asn Gln Asp Asp
                195                 200                 205

Pro Asn Val Leu Glu Ile Trp Asn Leu Val Phe Ile Gln Tyr Asn Arg
    210                 215                 220

Glu Ala Asp Gly Ile Leu Lys Pro Leu Pro Lys Lys Ser Ile Asp Thr
225                 230                 235                 240

Gly Met Gly Leu Glu Arg Leu Val Ser Val Leu Gln Asn Lys Met Ser
                245                 250                 255
```

-continued

Asn Tyr Asp Thr Asp Leu Phe Val Pro Tyr Phe Glu Ala Ile Gln Lys
            260                 265                 270

Gly Thr Gly Ala Arg Pro Tyr Thr Gly Lys Val Gly Ala Glu Asp Ala
        275                 280                 285

Asp Gly Ile Asp Met Ala Tyr Arg Val Leu Ala Asp His Ala Arg Thr
        290                 295                 300

Ile Thr Val Ala Leu Ala Asp Gly Gly Arg Pro Asp Asn Thr Gly Arg
305                 310                 315                 320

Gly Tyr Val Leu Arg Arg Ile Leu Arg Arg Ala Val Arg Tyr Ala His
                325                 330                 335

Glu Lys Leu Asn Ala Ser Arg Gly Phe Phe Ala Thr Leu Val Asp Val
                340                 345                 350

Val Val Gln Ser Leu Gly Asp Ala Phe Pro Glu Leu Lys Lys Asp Pro
            355                 360                 365

Asp Met Val Lys Asp Ile Ile Asn Glu Glu Glu Val Gln Phe Leu Lys
        370                 375                 380

Thr Leu Ser Arg Gly Arg Arg Ile Leu Asp Arg Lys Ile Gln Ser Leu
385                 390                 395                 400

Gly Asp Ser Lys Thr Ile Pro Gly Asp Thr Ala Trp Leu Leu Tyr Asp
                405                 410                 415

Thr Tyr Gly Phe Pro Val Asp Leu Thr Gly Leu Ile Ala Glu Glu Lys
                420                 425                 430

Gly Leu Val Val Asp Met Asp Gly Phe Glu Glu Arg Lys Leu Ala
            435                 440                 445

Gln Leu Lys Ser Gln Gly Lys Gly Ala Gly Gly Glu Asp Leu Ile Met
        450                 455                 460

Leu Asp Ile Tyr Ala Ile Glu Glu Leu Arg Ala Arg Gly Leu Glu Val
465                 470                 475                 480

Thr Asp Asp Ser Pro Lys Tyr Asn Tyr His Leu Asp Ser Ser Gly Ser
                485                 490                 495

Tyr Val Phe Glu Asn Thr Val Ala Thr Val Met Ala Leu Arg Arg Glu
            500                 505                 510

Lys Met Phe Val Glu Glu Val Ser Thr Gly Gln Glu Cys Gly Val Val
        515                 520                 525

Leu Asp Lys Thr Cys Phe Tyr Ala Glu Gln Gly Gly Gln Ile Tyr Asp
530                 535                 540

Glu Gly Tyr Leu Val Lys Val Asp Asp Ser Ser Glu Asp Lys Thr Glu
545                 550                 555                 560

Phe Thr Val Lys Asn Ala Gln Val Arg Gly Gly Tyr Val Leu His Ile
                565                 570                 575

Gly Thr Ile Tyr Gly Asp Leu Lys Val Gly Asp Gln Val Trp Leu Phe
            580                 585                 590

Ile Asp Glu Pro Arg Arg Pro Ile Met Ser Asn His Thr Ala Thr
        595                 600                 605

His Ile Leu Asn Phe Ala Leu Arg Ser Val Leu Gly Glu Ala Asp Gln
        610                 615                 620

Lys Gly Ser Leu Val Ala Pro Asp Arg Leu Arg Phe Asp Phe Thr Ala
625                 630                 635                 640

Lys Gly Ala Met Ser Thr Gln Gln Ile Lys Lys Ala Glu Glu Ile Ala
                645                 650                 655

Asn Glu Met Ile Glu Ala Ala Lys Ala Val Tyr Thr Gln Asp Cys Pro
            660                 665                 670

```
Leu Ala Ala Ala Lys Ala Ile Gln Gly Leu Arg Ala Val Phe Asp Glu
            675                 680                 685

Thr Tyr Pro Asp Pro Val Arg Val Val Ser Ile Gly Val Pro Val Ser
690                 695                 700

Glu Leu Leu Asp Asp Pro Ser Gly Pro Ala Gly Ser Leu Thr Ser Val
705                 710                 715                 720

Glu Phe Cys Gly Gly Thr His Leu Arg Asn Ser Ser His Ala Gly Ala
                725                 730                 735

Phe Val Ile Val Thr Glu Glu Ala Ile Ala Lys Gly Ile Arg Arg Ile
            740                 745                 750

Val Ala Val Thr Gly Ala Glu Ala Gln Lys Ala Leu Arg Lys Ala Glu
            755                 760                 765

Ser Leu Lys Lys Cys Leu Ser Val Met Glu Ala Lys Val Lys Ala Gln
770                 775                 780

Thr Ala Pro Asn Lys Asp Val Gln Arg Glu Ile Ala Asp Leu Gly Glu
785                 790                 795                 800

Ala Leu Ala Thr Ala Val Ile Pro Gln Trp Gln Lys Asp Glu Leu Arg
                805                 810                 815

Glu Thr Leu Lys Ser Leu Lys Lys Val Met Asp Asp Leu Asp Arg Ala
            820                 825                 830

Ser Lys Ala Asp Val Gln Lys Arg Val Leu Glu Lys Thr Lys Gln Phe
            835                 840                 845

Ile Asp Ser Asn Pro Asn Gln Pro Leu Val Ile Leu Glu Met Glu Ser
850                 855                 860

Gly Ala Ser Ala Lys Ala Leu Asn Glu Ala Leu Lys Leu Phe Lys Met
865                 870                 875                 880

His Ser Pro Gln Thr Ser Ala Met Leu Phe Thr Val Asp Asn Glu Ala
                885                 890                 895

Gly Lys Ile Thr Cys Leu Cys Gln Val Pro Gln Asn Ala Ala Asn Arg
            900                 905                 910

Gly Leu Lys Ala Ser Glu Trp Val Gln Gln Val Ser Gly Leu Met Asp
            915                 920                 925

Gly Lys Gly Gly Lys Asp Val Ser Ala Gln Ala Thr Gly Lys Asn
930                 935                 940

Val Gly Cys Leu Gln Glu Ala Leu Gln Leu Ala Thr Ser Phe Ala Gln
945                 950                 955                 960

Leu Arg Leu Gly Asp Val Lys Asn
            965

<210> SEQ ID NO 11
<211> LENGTH: 105
<212> TYPE: PRT
<213> ORGANISM: Homo sapiens

<400> SEQUENCE: 11

Met Val Lys Gln Ile Glu Ser Lys Thr Ala Phe Gln Glu Ala Leu Asp
1               5                   10                  15

Ala Ala Gly Asp Lys Leu Val Val Val Asp Phe Ser Ala Thr Trp Cys
            20                  25                  30

Gly Pro Cys Lys Met Ile Lys Pro Phe Phe His Ser Leu Ser Glu Lys
        35                  40                  45

Tyr Ser Asn Val Ile Phe Leu Glu Val Asp Val Asp Asp Cys Gln Asp
    50                  55                  60

Val Ala Ser Glu Cys Glu Val Lys Cys Met Pro Thr Phe Gln Phe Phe
65                  70                  75                  80
```

```
Lys Lys Gly Gln Lys Val Gly Glu Phe Ser Gly Ala Asn Lys Glu Lys
                85                  90                  95

Leu Glu Ala Thr Ile Asn Glu Leu Val
            100                 105

<210> SEQ ID NO 12
<211> LENGTH: 115
<212> TYPE: PRT
<213> ORGANISM: Homo sapiens

<400> SEQUENCE: 12

Met Pro Met Phe Ile Val Asn Thr Asn Val Pro Arg Ala Ser Val Pro
1               5                   10                  15

Asp Gly Phe Leu Ser Glu Leu Thr Gln Gln Leu Ala Gln Ala Thr Gly
            20                  25                  30

Lys Pro Pro Gln Tyr Ile Ala Val His Val Val Pro Asp Gln Leu Met
        35                  40                  45

Ala Phe Gly Gly Ser Ser Glu Pro Cys Ala Leu Cys Ser Leu His Ser
    50                  55                  60

Ile Gly Lys Ile Gly Gly Ala Gln Asn Arg Ser Tyr Ser Lys Leu Leu
65                  70                  75                  80

Cys Gly Leu Leu Ala Glu Arg Leu Arg Ile Ser Pro Asp Arg Val Tyr
                85                  90                  95

Ile Asn Tyr Tyr Asp Met Asn Ala Ala Asn Val Gly Trp Asn Asn Ser
            100                 105                 110

Thr Phe Ala
        115

<210> SEQ ID NO 13
<211> LENGTH: 170
<212> TYPE: PRT
<213> ORGANISM: Homo sapiens

<400> SEQUENCE: 13

Met Gly Leu Ala Gly Val Cys Ala Leu Arg Arg Ser Ala Gly Tyr Ile
1               5                   10                  15

Leu Val Gly Gly Ala Gly Gly Gln Ser Ala Ala Ala Ala Ala Arg Arg
            20                  25                  30

Cys Ser Glu Gly Glu Trp Ala Ser Gly Val Arg Ser Phe Ser Arg
        35                  40                  45

Ala Ala Ala Ala Met Ala Pro Ile Lys Val Gly Asp Ala Ile Pro Ala
    50                  55                  60

Val Glu Val Phe Glu Gly Glu Pro Gly Asn Lys Val Asn Leu Ala Glu
65                  70                  75                  80

Leu Phe Lys Gly Lys Lys Gly Val Leu Phe Gly Val Pro Gly Ala Phe
                85                  90                  95

Thr Pro Gly Cys Ser Lys Val Arg Leu Leu Ala Asp Pro Thr Gly Ala
            100                 105                 110

Phe Gly Lys Glu Thr Asp Leu Leu Leu Asp Asp Ser Leu Val Ser Ile
        115                 120                 125

Phe Gly Asn Arg Arg Leu Lys Arg Phe Ser Met Val Val Gln Asp Gly
    130                 135                 140

Ile Val Lys Ala Leu Asn Val Glu Pro Asp Gly Thr Gly Leu Thr Cys
145                 150                 155                 160

Ser Leu Ala Pro Asn Ile Ile Ser Gln Leu
                165                 170
```

POLYPEPTIDE STRUCTURAL MOTIFS ASSOCIATED WITH CELL SIGNALING ACTIVITY

CROSS REFERENCE TO RELATED APPLICATIONS

This application is a Continuation of U.S. patent application Ser. No. 13/203,831, filed Aug. 29, 2011; which is a 371 National Stage entry of PCT/US2010/025642, filed Feb. 26, 2010; which claims the benefit under 35 U.S.C. §119(e) of U.S. Provisional Patent Application No. 61/156,370, filed Feb. 27, 2009, each of which is incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ATYR_011_02US_ST25.txt. The text file is about 64 KB, was created on Nov. 19, 2014, and is being submitted electronically via EFS-Web, concurrent with the filing of the specification.

BACKGROUND OF THE INVENTION

1. Field of the Invention

The present invention relates generally to polypeptides containing structural motifs associated with cell signaling and other biologically relevant activities, compositions comprising such polypeptides, and methods of identifying and using same.

2. Description of the Related Art

Aminoacyl-tRNA synthetase (AARS) proteins, which catalyze the aminoacylation of tRNA molecules, are essential for decoding genetic information during the process of translation. Each of the eukaryotic tRNA synthetases consists of a core enzyme, which is closely related to the prokaryotic tRNA synthetase, as well as additional domains that are appended to the amino-terminal end, carboxyl-terminal end or inserted into a region internal to the core enzyme. Human tyrosyl-tRNA synthetase (TyrRS), for example, has a carboxyl-terminal domain that is not part of prokaryotic and lower eukaryotic TyrRS molecules. Several aminoacyl-tRNA synthetases have been demonstrated to have non-canonical functions distinct from their involvement in translation. For example, mini-tyrosyl tRNA synthetase (mini-TyrRS), the N-terminal domain of TyrRS which corresponds to amino acid residues 1-364 and is cleaved by polymorphonuclear cell elastase and plasmin, exhibits non-canonical activities not found in the full-length protein. In vitro, mini-TyrRS has been shown to stimulate neutrophil activation and chemotaxis, endothelial cell proliferation and migration, and is pro-angiogenic in chick chorioallantoic membrane (CAM) and mouse matrigel assays. Mini-TyrRS has an ELR motif that, like CXC-chemokines such as IL-8, is involved in many of its chemokine and angiogenic activities. As in other ELR-containing cytokines, mutation of this motif inhibits mini-TyrRS binding to and stimulation of leukocytes and angiogenesis.

In addition, truncated forms of TrpRS have been demonstrated to have anti-angiogenic properties. In normal human cells, there are two forms of TrpRS that can be detected: a major form consisting of the full-length molecule (amino acid residues 1-471) and a minor truncated form. The minor form is generated by the deletion of an amino-terminal domain through alternative splicing of the pre-mRNA and is termed mini-TrpRS. The amino-terminus of miniTrpRS has been determined to be the methionine residue at position 48 of the full-length TrpRS molecule. Alternatively, truncated TrpRS can be generated by proteolysis. For example, bovine TrpRS is highly expressed in the pancreas and is secreted into the pancreatic juice, thus resulting in the production of a truncated TrpRS molecule. Additional studies indicate that miniTrpRS inhibits VEGF-induced cell proliferation and migration (Wakasugi et al., Proc. Natl. Acad. Sci. 99: 173-177 (2002)). In particular, a chick CAM assay shows that miniTrpRS blocks angiogenic activity of VEGF. In contrast, the full-length TrpRS does not inhibit angiogenesis. Thus, removal of the first 48 amino acid residues exposes the anti-angiogenic activity of TrpRS. Therefore, as with TyrRS, certain forms of TrpRS possess activities other than the aminoacylation of tRNA.

Other cytoplasmic proteins have also been shown to have isoforms with extracellular biological activities. For example, human thioredoxin (Hu-Trx) serves a key role in redox activities within the cytoplasm of cells, but has a truncated secreted form that is a mitogenic cytokine (Arner, 2000; Eur J biochem 267:6102-6109).

Unfortunately, there are no reliable methods available for predicting or identifying which cytoplasmic proteins or polypeptide fragments derived from AARS proteins and/or other proteins may have novel and previously unappreciated activities. The present invention addresses these needs and offers other related advantages.

SUMMARY OF THE INVENTION

The present invention relates to isolated polypeptides comprising or consisting essentially of particular structural motifs, as described herein, which exhibit at least one cell signaling and/or other non-canonical activity of biological relevance. The present invention further relates to polynucleotides encoding such polypeptides, binding agents that bind such polypeptides, analogs, variants and fragments of such polypeptides, etc., as well as compositions and methods of identifying and using any of the foregoing.

Therefore, according to one aspect of the invention, there are provided isolated polypeptides comprising or consisting essentially of three β-sheets and two α-helices, wherein the polypeptides exhibit a cell signaling and/or other non-canonical activity relative to the protein from which they were derived. The precise order and orientation of the required β-sheets and α-helices within a polypeptide of the invention may vary while still giving rise to the desired cell signaling and/or other non-canonical activities. However, in a particularly illustrative embodiment, a polypeptide of the invention consists essentially of three antiparallel β-sheets flanked at each end by an α-helix.

The size of a polypeptide of the invention can vary while still having the desired structural and functional features described herein. However, in certain illustrative embodiments, an isolated polypeptide of the invention will have a size in the range of about 40-400, 50-300 or 60-200 amino acid residues.

In many embodiments, a polypeptide of the invention will be a contiguous fragment of a mammalian protein (e.g., a human protein), or a sequence sharing substantial structural identity (e.g., at least 70%, 80% or 90%) with said contiguous fragment. However, in other embodiments, it will be understood that the polypeptide may be comprised of two or more non-contiguous fragments of a protein, or sequences sharing substantial sequence identity with said non-contiguous fragments.

In a specific embodiment of the invention, an isolated polypeptide of the invention is a GlyRS (GRS) polypeptide comprising or consisting essentially of residues 345-438 of SEQ ID NO: 1, which fragment has been identified herein as containing a structural motif of the invention and having cell signaling activity. In a related embodiment, the isolated polypeptide is an active fragment or variant of a polypeptide comprising residues 345-438 of SEQ ID NO: 1, e.g., a fragment of the polypeptide which retains the same or similar cell signaling activity or a variant which shares substantial sequence identity thereto (e.g., at least 80% or 90%) and which retains the same or similar cell signaling activity.

In another specific embodiment of the invention, the polypeptide is an AspRS (DRS) polypeptide comprising or consisting essentially of residues 367-448 of SEQ ID NO: 2 or an active fragment or variant thereof.

In another specific embodiment, the polypeptide is a HisRS (HRS) polypeptide comprising or consisting essentially of residues 294-372 of SEQ ID NO: 3 or an active fragment or variant thereof.

In yet another specific embodiment, the polypeptide is a ThrRS (TRS) polypeptide comprising or consisting essentially of residues 469-586 of SEQ ID NO: 4 or an active fragment or variant thereof.

In another specific embodiment, the polypeptide is a GluProRS (EPRS) polypeptide comprising or consisting essentially of residues 1171-1253 of SEQ ID NO: 5 or an active fragment or variant thereof.

In still another specific embodiment of the invention, the polypeptide is a SerRS (SRS) polypeptide comprising or consisting essentially of residues 325-410 of SEQ ID NO: 6 or an active fragment or variant thereof.

In still another specific embodiment of the invention, the polypeptide is a PheRS (FRS) polypeptide comprising or consisting essentially of residues 380-449 of SEQ ID NO: 7 or an active fragment or variant thereof.

In still another specific embodiment of the invention, the polypeptide is a LysRS (KRS) polypeptide comprising or consisting essentially of residues 425-523 of SEQ ID NO: 8 or an active fragment or variant thereof.

In still another specific embodiment of the invention, the polypeptide is a AspRS (NRS) polypeptide comprising or consisting essentially of residues 416-494 of SEQ ID NO: 9 or an active fragment or variant thereof.

In still another specific embodiment of the invention, the polypeptide is a AlaRS (ARS) polypeptide comprising or consisting essentially of residues 148-258 of SEQ ID NO: 10 or an active fragment or variant thereof.

In another specific embodiment of the invention, the polypeptide is a thioredoxin polypeptide comprising or consisting essentially of residues 20-105 of SEQ ID NO: 11 or an active fragment or variant thereof. In another embodiment, the polypeptide is a Trx80 polypeptide comprising or consisting essentially of residues 20-84 of Trx80, which is a secreted form of thioredoxin containing the N-terminal 84 amino acid residues of thioredoxin.

In another specific embodiment, the polypeptide is a macrophage inhibitory factor polypeptide comprising or consisting essentially of residues 1-90 of SEQ ID NO: 12 or an active fragment or variant thereof.

In yet another specific embodiment, the polypeptide is a human peroxiredoxin 5 isoform B polypeptide comprising or consisting essentially of residues 32-68 and 125-161 of SEQ ID NO: 13 or an active fragment or variant thereof.

In certain embodiments, the cell signaling activity of a polypeptide of the invention is a chemokine and/or cytokine activity and may be determined and/or confirmed using any of a variety of illustrative assays known and established in the art. In specific embodiments, cell signaling activity may be determined using essentially any assay that measures cytokine activity, chemokine activity, chemotaxis, cell migration, cytokine release, cell differentiation and/or cell toxicity. In more specific embodiments, cytokine activity may be determined, for example, using an assay which measures GPCR-dependent chemotaxis of monocytes, release of interleukins, and/or apoptosis.

Certain embodiments include methods of modulating chemokine activity, such as TNF-α secretion. Specific embodiments include methods of inducing TNF-α secretion. Certain embodiments include methods of modulating immune cell chemotaxis. Specific embodiments include methods of inducing monocyte chemotaxis. Certain embodiments include methods of modulating Toll-like receptor signaling. Specific embodiments include methods of inducing Toll-like receptor 2 signaling.

According to another aspect of the invention, there is provided an isolated polynucleotide encoding a polypeptide as described herein.

According to yet another aspect, the invention provides a pharmaceutical composition comprising a polypeptide as described herein, or a polynucleotide encoding a polypeptide as described herein.

According to another aspect, the invention provides a vector comprising an isolated polynucleotide as described herein, as well as a host cell comprising such a vector.

According to yet another aspect, the invention provides screening methods for identifying proteins containing a structural motif of the invention and thereby identifying novel polypeptide fragments within said proteins that possess cell signaling and/or other non-canonical activities. For example, in one embodiment, the invention provides a method for identifying a polypeptide fragment having a cytokine activity by identifying a protein sequence containing a structural motif as described herein, e.g., comprised of two α-helices and three β-sheets, determining the amino acid residue boundaries of the structural motif within said protein, and thereby identifying a polypeptide fragment of the protein which has a cytokine activity.

In certain embodiments of the described screening methods, the step of identifying a protein sequence containing a structural motif comprised of two α-helices and three antiparallel β-sheets is performed using a secondary structure prediction method known and available in the art, which may illustratively include, but are not limited to, PHDsec, NSSP, SOPM, DSC, SSPRED, MultiPredict, PSA, NNPREDICT, APSSP, GOR, HNN, HTMSRAP, Jpred, JUFO, nnPredict, Porter, PredictProtein, Prof, PSIpred, SOPMA, SSpro and DLP-SVM.

In still other aspects, the polypeptides, antibodies and/or other compositions of the present invention may be used in essentially any type of screening assay known and available in the art. For example, compositions of the invention (e.g., polypeptides, polynucleotides and/or antibodies) may be used in conjunction with essentially any known screening methodology in order to identify suitable cell types and/or disease conditions amenable to treatment according to the present invention. In other examples, compositions of the invention (e.g., polypeptides, polynucleotides and/or antibodies) may be used in conjunction with known screening methodologies in order to identify binding partners, competitive inhibitors, cellular effectors, and the like, that mediate or modulate, either directly or indirectly, the cell signaling and/or non-canonical activities of the compositions herein. For example, in a particular embodiment, a screening method is provided for identifying test compounds as inhibitors, or alternatively, potentiators, of an interaction between a composition of the invention and one or more of its binding partners, cellular effectors and/or cell types subject to modulation. This may include, for example, steps of forming a reaction mixture including: (i) a composition of the invention, (ii) a binding partner, cellular effector and/or cell type known to be modulated by said composition, and (iii) a test compound; and detecting interaction of the test compound with the binding partner, cellular effector and/or cell type. A statistically significant change (potentiation or inhibition) in activity or modulation in the presence of the test compound, relative to the interaction in the absence of the test compound, indicates a potential agonist (mimetic or potentiator) or antagonist (inhibitor) of activity.

BRIEF DESCRIPTION OF SEQUENCE IDENTIFIERS

SEQ ID NO: 1 is the full length amino acid sequence of human glycyl-tRNA synthetase (GlyRS).

SEQ ID NO: 2 is the full length amino acid sequence of human aspartyl-tRNA synthetase (AspRS).

SEQ ID NO: 3 is the full length amino acid sequence of human histidyl-tRNA synthetase (HisRS).

SEQ ID NO: 4 is the full length amino acid sequence of human threonyl-tRNA synthetase (ThrRS).

SEQ ID NO: 5 is the full length amino acid sequence of human glutamyl-/prolyl-tRNA synthetase (GluProRS).

SEQ ID NO: 6 is the full length amino acid sequence of human seryl-tRNA synthetase (SerRS).

SEQ ID NO: 7 is the full length amino acid sequence of human phenylalanyl-tRNA synthetase (FRSa).

SEQ ID NO: 8 is the full length amino acid sequence of human lysyl-tRNA synthetase (KRS).

SEQ ID NO: 9 is the full length amino acid sequence of human asparaginyl-tRNA synthetase (NRS).

SEQ ID NO: 10 is the full length amino acid sequence of human alanyl-tRNA synthetase (ARS).

SEQ ID NO: 11 is the full length amino acid sequence of human thioredoxin.

SEQ ID NO: 12 is the full length amino acid sequence of human macrophage inhibitory factor.

SEQ ID NO: 13 is the full length amino acid sequence of human peroxiredoxin 5 isoform B.

BRIEF DESCRIPTION OF THE DRAWINGS

FIG. 2A shows the location of the G6 fragment and structural motif within full-length GlyRS. FIG. 2B shows a structural model of GlyRS residues 344-420. FIG. 2C shows that the G6 fragment induces GPCR-dependent migration of THP-1 monocyte cells.

FIG. 7A shows S3 binding to human monocytes, FIG. 7B shows S3 binding to human B-cells, and FIG. 7C shows induction of TNF-α secretion from human monocytic cell line (THP-1) as compared to LPS control.

DETAILED DESCRIPTION OF THE INVENTION

Figure 1:
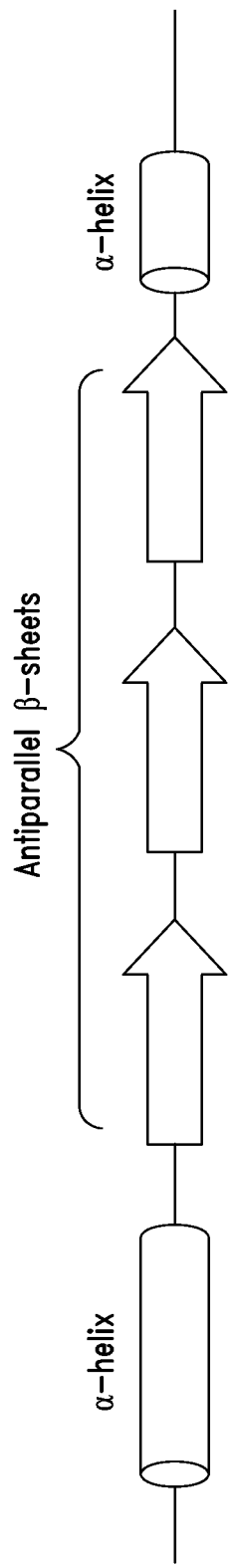
FIG. 1 shows an illustrative structural motif of the invention comprising three antiparallel β-sheets flanked by an α-helix at each end.

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., *Molecular Cloning: A Laboratory Manual* (2nd Edition, 1989); Maniatis et al., *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); *A Practical Guide to Molecular Cloning* (B. Perbal, ed., 1984).

All publications, patents and patent applications cited herein are hereby incorporated by reference in their entirety.

As used in this specification and the appended claims, the singular forms "a," "an" and "the" include plural references unless the content clearly dictates otherwise.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

An "agonist" refers to a molecule that intensifies or mimics the non-canonical biological activity of an AARS. Agonists may include proteins, nucleic acids, carbohydrates, small molecules, or any other compound or composition that modulates the activity of an AARS either by directly interacting with the AARS or its binding partner, or by acting on components of the biological pathway in which the ATRS participates. Included are partial and full agonists.

The term "antagonist" refers to a molecule that inhibits or attenuates the non-canonical biological activity of an AARS. Antagonists may include proteins such as antibodies, nucleic acids, carbohydrates, small molecules, or any other compound or composition that modulates the activity of an AARS or its binding partner, either by directly interacting with the AARS or its binding partner or by acting on components of the biological pathway in which the AARS participates. Included are partial and full antagonists.

The term "modulating" includes "increasing" or "stimulating," as well as "decreasing" or "reducing," typically in a statistically significant or a physiologically significant amount as compared to a control. An "increased" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the amount produced by no composition (the absence of an agent or compound) or a control composition. A "decreased" or reduced amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease in the amount produced by no composition (the absence of an agent or compound) or a control composition, including all integers in between.

A "subject," as used herein, includes any animal that exhibits a symptom, or is at risk for exhibiting a symptom, which can be treated or diagnosed with a composition of the invention. Suitable subjects (patients) include laboratory animals (such as mouse, rat, rabbit, or guinea pig), farm animals, and domestic animals or pets (such as a cat or dog). Non-human primates and, preferably, human patients, are included.

"Treatment" or "treating," as used herein, includes any desirable effect on the symptoms or pathology of a disease or condition that can be effected by the cell-modulatory activities of a composition as described herein, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

As used herein, the terms "polypeptide" and "protein" are used according to conventional meaning, i.e., as a sequence of amino acids. Polypeptides are not limited to a specific length, but, in the context of the present invention, typically represent a fragment of a full length protein, and may include post-translational modifications, for example, glycosylations, acetylations, phosphorylations and the like, as well as other modifications known in the art, both naturally occurring and non-naturally occurring. Polypeptides and proteins of the invention may be prepared using any of a variety of well known recombinant and/or synthetic techniques, illustrative examples of which are further discussed below.

The present invention relates generally to the identification of polypeptide structural motifs associated with unexpected biological activities of therapeutic relevance. For example, as further described herein, a protein structural motif was identified within an isolated fragment of the human glycyl-tRNA synthetase (GRS) protein, and this structural motif is believed to be responsible for the unexpected cell signaling activity found to be induced by the GlyRS fragment. Further analysis of the identified structural motif revealed its presence not only within other human AARS proteins, but also within other proteins unrelated to tRNA synthesis. Thus, based upon this discovery, the present invention provides a means for identifying polypeptide fragments having previously unrecognized cell signaling and/or other biological activities, and further provides the polypeptide fragments so identified. For example, in one illustrative embodiment, by identifying the presence of a structural motif of the invention within cytoplasmic proteins being screened, it is possible to delineate novel secreted polypeptide fragments of those cytoplasmic proteins having previously unappreciated activities unrelated to their canonical cytoplasmic activities.

Accordingly, the present invention broadly provides isolated polypeptides containing a structural motif as described herein, wherein the polypeptides exhibit at least one cell signaling or other non-canonical activity (e.g., an activity that is either not observed for the full length protein from which the polypeptide was derived or an activity that is significantly different (e.g., increased or decreased) relative to the full length protein from which it was derived).

In a particular embodiment of the invention, isolated polypeptides are provided that contain a structural motif comprised of two α-helices and three β-sheets, wherein the polypeptides exhibit at least one cell signaling or other non-canonical activity. In a more specific embodiment, isolated polypeptides are provided that contain a structural motif comprised of two α-helices and three antiparallel β-sheets, wherein the polypeptides exhibit at least one cell signaling or other non-canonical activity. In an even more specific embodiment, isolated polypeptides are provided that contain a structural motif comprised of three antiparallel β-sheets flanked by an α-helix at each end (e.g., as depicted illustratively in FIG. 1), wherein the polypeptides exhibit at least one cell signaling or other non-canonical activity.

A structural motif of the present invention, e.g., having three β-sheets and two α-helices, may be identified within a protein using essentially any of a variety of well known and established methodologies available in the art for the prediction of protein secondary structure. Secondary structure prediction is a set of techniques that can predict with high accuracy the local secondary structures of proteins based on knowledge of their primary amino acid sequence and/or other parameters. For proteins, a prediction generally consists of assigning regions of the amino acid sequence as likely to adopt a particular secondary structure, e.g., α-helices, β-strands, β-sheets, etc. The success of a prediction can be evaluated, for example, by comparing it to the results of the DSSP algorithm applied to the crystal structure of the protein (if available). Specialized algorithms have been developed for the detection of these and other well-defined patterns in proteins.

Accordingly, using such methodologies, the presence of structural motifs of the present invention within proteins being screened can be predicted with high accuracy using any of a number of well-known and publicly available programs and/or modeling tools for secondary structure prediction, several illustrative examples of which are set forth below:

ESyPred3D (http://www.fundp.ac.be/sciences/biologie/urbm/bioinfo/esypred/), Lambert C, Leonard N, De Bolle X, Depiereux E. *ESyPred3D: Prediction of proteins 3D structures*. Bioinformatics. 2002 September; 18(9):1250-1256, which is an automated homology modeling program;

I_Tasser (http://zhang.bioinformatics.ku.edu/I-TASSER/), which builds models based on multiple threading alignments;

Bhageerath (http://www.scfbio-iitd.res.in/bhageerath/index.jsp) an energy based protein structure prediction server'

PHDsec (http://www.embl-heidelberg.de/predictprotein/), which is a multiple alignment-based neural network system;

NSSP (http://dot.imgen.bcm.tmc.edu:9331/pssprediction/pssp.html), which is a multiple alignment-based nearest-neighbor method;

SOPM (http://www.ibcp.fr/predict.html), which is a multiple alignment-based method combining various prediction programs;

DSC (http://bonsai.lif.icnet.uk/bmm/dsc/dsc_read_align.html), which is a multiple alignment-based program using statistics;

SSPRED: (http://www.embl-heidelberg.de/sspred/ssp_mul.html), which is a multiple alignment-based program using statistics;

MultiPredict (http://kestrel.ludwig.ucl.ac.uk/zpred.html), which is a multiple alignment-based method using physicochemical information from a set of aligned sequences and statistical secondary structure decision constants;

PSA (http://bmerc-www.bu.edu/psa/), which analyzes amino acid sequences to predict secondary structures and folding classes;

NNPREDICT (http://www.cmpharm.ucsf.edu/~nomi/nnpredict.html), which is a single-sequence based neural network prediction;

APSSP (http://imtech.res.in/raghava/apssp/), which is known as the Advanced Protein Secondary Structure Prediction Server;

GOR (http://npsa-pbil.ibcp.fr/cgi-bin/npsa_automat.pl?page=npsa_gor4.html), which relies on Information theory/Bayesian inference (Garnier et al, 1996);

HNN (http://npsa-pbil.ibcp.fr/cgi-bin/npsa_automat.pl?page=npsa_nn.html) which relies on a Hierarchical Neural Network method (Guermeur, 1997);

HTMSRAP (http://biotechnology.tbzmed.ac.ir/htmsrap/index.htm), which employs Helical TransMembrane Segment Rotational Angle Prediction;

Jpred (http://www.compbio.dundee.ac.uk/~www-jpred/), which involves neural network-based secondary structure prediction;

JUFO (http://www.meilerlab.org/view.php?section=0&page=6), which involves neural network-based protein secondary structure prediction;

nnPredict (http://www.cmpharm.ucsf.edu/~nomi/nnpredict.html);

Porter (http://distill.ucd.ie/porter/);

PredictProtein (http://www.predictprotein.org/), which includes PHDsec, PHDacc, PHDhtm, PHDtopology, PHDthreader, MaxHom and EvalSec;

Prof (http://www.aber.ac.uk/~phiwww/prof/), which uses cascaded multiple classifiers for secondary structure prediction;

PSIpred (http://bioinf.cs.ucl.ac.uk/psipred/), which includes various protein structure prediction methods;

SOPMA (http://npsa-pbil.ibcp.fr/cgi-bin/npsa_automat.pl?page=npsa_sopma.html) (Geourjon and Déleage, 1995)

SSpro (http://www.igb.uci.edu/?page=tools&subPage=psss), which includes secondary structure prediction using bidirectional recurrent neural networks; and, DLP-SVM (http://www.tuat.ac.jp/~domserv/cgi-bin/DLP-SVM.cgi), which involves domain linker prediction using SVM.

Additional information regarding certain of these and other secondary structure prediction methodologies for single sequences can be found, for example, in Chou et al. (1974) *Biochemistry*, 13, 211-222; Lim (1974) *Journal of Molecular Biology*, 88, 857-872; Garnier et al. (1978) *Journal of Molecular Biology*, 120, 97-120; Kabsch et al. (1983) *FEBS Letters*, 155, 179-182; Deleage et al. (1987) *Protein Engineering*, 1, 289-294 (DPM; http://www.ibcp.fr/serv_pred.html); Presnell et al. (1992) *Biochemistry*, 31, 983-993; Holley et al. (1989) *Proceedings of the National Academy of Science*, 86, 152-156; King et al. (1990). *Journal of Molecular Biology*, 216, 441-457; and Kneller et al. (1990) *Journal of Molecular Biology*, 214, 171-182 (NNPRED; http://www.cmpharm.ucsf.edu/~nomi/nnpredict.html).

Furthermore, additional information regarding certain of these and other automated methods for predicting secondary structure from multiply aligned protein sequences can be found, for example, in Zvelebil et al. (1987) *Journal of Molecular Biology*, 195, 957-961 (ZPRED); Rost et al. (1993) *Journal of Molecular Biology*, 232, 584-599 (PHD; http://www.embl-heidelberg.de/predictprotein/predictprotein.html); Salamov et al. (1995) *Journal of Molecular Biology*, 247, 1 (NNSSP; http://dot.imgen.bcm.tmc.edu:9331/seq-search/struc-predict.html); Geourjon et al. (1994), *Protein Engineering*, 7, 157-16 (SOPMA; http://www.ibcp.fr/serv_pred.html); Solovyev et al. (1994) *Computer Applications in the Biosciences*, 10, 661-669. (SSP; http://dot.imgen.bcm.tmc.edu:9331/seq-search/struc-predict.html); Wako et al. (1994) *Journal of Molecular Biology*, 238, 693-708; Mehta et al. (1995) *Protein Science* 4, 2517-25 (SSPRED; http://www.embl-heidelberg.de/sspred/sspred_info.html); and King et al. (1996) *Protein Sci* 5, 2298-2310. (DSC; http://www.bmm.icnet.uk/dsc/dsc_form_align.html).

Structure visualization software can also be used, if desired, in conjunction with publically available crystal structures for AARS or non-AARS proteins (e.g., via Swiss Prot database on the NIH Entrez server) to visualize a protein of interest and identify structural motifs (e.g., Accelrys Software Inc., *Discovery Studio Modeling Environment*, Release 2.0, San Diego: Accelrys Software Inc., 2007). Still other illustrative software tools available for identifying secondary structural motifs include ESyPred3d (Lambert 2002; ESyPred3D: Prediction of proteins 3D structures. Bioinformatics 18:1250-1256). Structure predictions can then be visually inspected (e.g., in Accelrys Discovery Visualizer) for peptide domains that have the desired structural motif.

After identifying a protein or polypeptide containing a desired structural motif of the invention (e.g., containing three β-sheets flanked on each end by α-helices), using one or more suitable techniques such as those discussed above, the amino acid boundaries of the motif are determined and isolated polypeptide fragments containing the motif can be produced (e.g., synthetically or recombinantly) and tested for confirmation of cell signaling activity.

A polypeptide of the invention is said to have a "cell signaling activity" when the polypeptide exhibits one or more activities commonly associated with and/or induced by cell signaling proteins, either directly or indirectly. In certain embodiments, the cell signaling activity is a cytokine and/or chemokine activity. Cytokines are a category of cell-signaling molecules and chemokines are a family of small cytokines, or proteins secreted by cells.

Proteins are generally classified as chemokines according to shared structural characteristics such as small size (they are all approximately 8-10 kilodaltons in size), and the presence of four cysteine residues in conserved locations that are key to forming their 3-dimensional shape. A hallmark activity of chemokines is their ability to act as chemoattractants to induce and/or control the migration of cells. Cells that are attracted by chemokines generally follow a signal of increasing chemokine concentration towards the source of the chemokine.

Chemokines serve various biological roles. Some chemokines control cells of the immune system during processes of immune surveillance, such as directing lymphocytes to the lymph nodes so they can screen for invasion of pathogens by interacting with antigen-presenting cells residing in these tissues. These are known as homeostatic chemokines and are produced and secreted without any need to stimulate their source cells. Some chemokines have roles in development, such as promoting angiogenesis (the growth of new blood vessels), or guiding cells to tissues that provide specific signals critical for cellular maturation. Other chemokines are inflammatory and are released from a wide variety of cells in response to bacterial infection, viruses and agents that cause physical damage. Their release is often stimulated by pro-inflammatory cytokines such as interleukin 1. Inflammatory chemokines function mainly as chemoattractants for leukocytes, recruiting monocytes, neutrophils and other effector cells from the blood to sites of infection or tissue damage. Certain inflammatory chemokines activate cells to initiate an immune response or promote wound healing. They are released by many different cell types and serve to guide cells of both innate immune system and adaptive immune system. Chemokines exert many of their biological effects by interacting with G protein-linked transmembrane receptors called chemokine receptors, which are selectively found on the surfaces of their target cells.

Given these various biological roles and activities, the chemokine, cytokine or cell signaling activities of a polypeptide of the invention can be determined using any of a number of routine and art-recognized assays. In certain embodiment, cell signaling activity is determined using essentially any assay that measures chemotaxis, cell migration, cytokine release, cell differentiation and/or cell viability. In more specific embodiments, chemokine activity is determined, for example, using an assay which measures GPCR-dependent chemotaxis of monocytes release of interleukins and/or apoptosis.

The isolated polypeptides of the invention can be essentially any length and can be of essentially any origin as long as they provide the necessary elements to constitute a structural motif possessing the desired cell signaling or other non-canonical activity.

In certain illustrative embodiments, a polypeptide of the invention will range in size from about 30-100, 30-200, 30-300, 30-400, 30-500, 40-100, 40-200, 40-300, 40-400, 40-500, 50-100, 50-200, 50-300, 50-400, 50-500, 60-100, 60-200, 60-300, 60-400 or 60-500 amino acids.

In certain embodiments, a polypeptide of the invention is a truncated mammalian (e.g., human) protein or an active variant thereof. A truncated protein refers to a polypeptide which is shorter than its corresponding full length protein, for example, due to removal of amino acids from its N- and/or C-terminal ends. The extent of the truncation, that is, the number of N- and/or C-terminal amino acid residues removed from a full length protein can vary considerably while still providing desired cellular effects when administered to a cell, tissue or subject, as described herein. In certain embodiments, at least about 5, 10, 15, 20, 25, 50, 75, 100, 150, 200, 250, 300, 350 amino acids, or more, including all intermediate lengths, are truncated from the N- and/or C-terminus of a full length protein. Intermediate lengths are intended to include all integers there between, for example, 6, 7, 8, etc., 51, 52, 53, etc., 201, 202, 203, etc.

In other embodiments, a polypeptide of the invention is comprised of one or more fragments of a mammalian protein, or active variants thereof. For example, in one illustrative embodiment, a polypeptide of the invention is comprised of a linear stretch of contiguous amino acid (e.g., having a length within the ranges noted above) derived from a mammalian protein, such as a human protein. Alternatively, a polypeptide of the invention may be comprised of non-contiguous fragments of a mammalian protein, wherein the non-contiguous fragments are sufficient to constitute a structural motif as described herein.

In a specific embodiment of the invention, the polypeptide is a fragment of a GlyRS protein, wherein the fragment has a cell signaling or other non-canonical activity. In a more specific embodiment, the polypeptide is a truncated form of a GlyRS protein comprising amino acid residues 345-420 of the human GlyRS protein set forth in SEQ ID NO: 1, or an active fragment or variant thereof.

In another embodiment of the invention, the polypeptide is a fragment of an AspRS protein, wherein the fragment has a cell signaling or other non-canonical activity. In a more specific embodiment, the polypeptide is a truncated form of an AspRS protein comprising amino acid residues 367-448 of the human AspRS protein set forth in SEQ ID NO: 2, or an active fragment or variant thereof.

In another embodiment, the polypeptide is a fragment of a HisRS protein, wherein the fragment has a cell signaling or other non-canonical activity. In a more specific embodiment, the polypeptide is a truncated form of a HisRS protein comprising amino acid residues 294-372 of the human HisRS protein set forth in SEQ ID NO: 3, or an active fragment or variant thereof.

In yet another embodiment of the invention, the polypeptide is a fragment of a ThrRS protein, wherein the fragment has a cell signaling or other non-canonical activity. In a more specific embodiment, the polypeptide is a truncated form of a ThrRS protein comprising amino acid residues 469-586 of the human ThrRS protein set forth in SEQ ID NO: 4, or an active fragment or variant thereof.

In another embodiment, the polypeptide is a fragment of a GluProRS protein, wherein the fragment has a cell signaling or other non-canonical activity. In a more specific embodiment, the polypeptide is a truncated form of a GluProRS protein comprising amino acid residues 1171-1253 of the human GluProRS protein set forth in SEQ ID NO: 5, or an active fragment or variant thereof.

In another embodiment, the polypeptide is a fragment of a SerRS protein, wherein the fragment has a cell signaling or other non-canonical activity. In a more specific embodiment, the polypeptide is a truncated form of a SerRS protein comprising amino acid residues 325-410 of the human SerRS protein set forth in SEQ ID NO: 6, or an active fragment or variant thereof.

In another embodiment, the polypeptide is a fragment of a PheRS protein, wherein the fragment has a cell signaling or other non-canonical activity. In a more specific embodiment of the invention, the polypeptide is a PheRS (FRS) polypeptide comprising residues 380-449 of SEQ ID NO: 7 or an active fragment or variant thereof.

In another embodiment, the polypeptide is a fragment of a LysRS protein, wherein the fragment has a cell signaling or other non-canonical activity. In a more specific embodiment of the invention, the polypeptide is a LysRS (KRS) polypeptide comprising residues 425-523 of SEQ ID NO: 8 or an active fragment or variant thereof.

In another embodiment, the polypeptide is a fragment of a AsnRS protein, wherein the fragment has a cell signaling or other non-canonical activity. In a more specific embodiment of the invention, the polypeptide is a AsnRS(NRS) polypeptide comprising residues 416-494 of SEQ ID NO: 9 or an active fragment or variant thereof.

In another embodiment, the polypeptide is a fragment of a AlaRS protein, wherein the fragment has a cell signaling or other non-canonical activity. In a more specific embodiment of the invention, the polypeptide is a AlaRS (ARS) polypeptide comprising residues 148-258 of SEQ ID NO: 10 or an active fragment or variant thereof.

In still another embodiment, the polypeptide is a fragment of a thioredoxin protein, wherein the fragment has a cell signaling or other non-canonical activity. In a more specific embodiment, the polypeptide is a truncated form of a thioredoxin protein comprising amino acid residues 20-105 of the human thioredoxin protein set forth in SEQ ID NO: 11, or an active fragment or variant thereof.

In another embodiment, the polypeptide is a fragment of a macrophage inhibitory factor protein, wherein the fragment has a cell signaling or other non-canonical activity. In a more specific embodiment, the polypeptide is a truncated form of a macrophage inhibitory factor protein comprising amino acid residues 1-90 of the human macrophage inhibitory factor protein set forth in SEQ ID NO: 12, or an active fragment or variant thereof.

In yet another embodiment, the polypeptide is a fragment of a human peroxiredoxin 5 isoform B protein, wherein the fragment has a cell signaling or other non-canonical activity. In a more specific embodiment, the polypeptide is a truncated form of a human peroxiredoxin 5 isoform B comprising amino acid residues 32-68 and 125-161 of the sequence set forth in SEQ ID NO: 13, or an active fragment or variant thereof.

In another specific embodiment, the polypeptide if the invention is not a fragment of a TrpRS or TyrRS protein.

In another embodiment, the polypeptide is not a HisRS fragment consisting of the first 48 amino acids of the HisRS protein.

In another embodiment, the polypeptide is not a thioredoxin fragment consisting of the first 80 or 84 N-terminal amino acids of the thioredoxin protein.

The present invention further provides variants of the polypeptides described herein. Polypeptide variants encompassed by the present invention will typically exhibit at least about 70%, 75%, 80%, 85%, 90%, 91%, 92%, 93%, 94%, 95%, 96%, 97%, 98%, or 99% identity (determined, for example, as described below), along their lengths, to the corresponding region of a wild-type or reference sequence from which it is derived.

A polypeptide variant may differ from a naturally occurring polypeptide of the invention in one or more substitutions, deletions, additions and/or insertions. Such variants may be naturally occurring or may be synthetically generated, for example, by modifying one or more of the above polypeptide sequences of the invention and evaluating their biological activity as described herein using any of a number of techniques well known in the art.

In other illustrative embodiments, the variant may be a splice variant, whether naturally or non-naturally occurring, wherein the splice variant possesses at least one non-canonical activity, e.g., as described herein.

In other illustrative embodiments, the variant contains one or more point mutations relative to a wild type or reference polypeptide sequence, whether naturally or non-naturally occurring, wherein the variant polypeptide possesses at least one non-canonical activity, e.g., as described herein.

In certain embodiments, a variant will contain conservative substitutions. A "conservative substitution" is one in which an amino acid is substituted for another amino acid that has similar properties, such that one skilled in the art would expect the secondary structure and hydropathic nature of the polypeptide to be substantially unchanged. Modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant of a polypeptide of the invention, one skilled in the art, for example, can change one or more of the codons of the encoding DNA sequence according to Table 1.

For example, certain amino acids may be substituted for other amino acids in a protein structure without appreciable loss of interactive binding capacity with structures such as, for example, receptors, antigen-binding regions of antibodies or binding sites on a substrate molecule. Since it is the interactive capacity and nature of a protein that generally defines that protein's biological functional activity, certain amino acid sequence substitutions can be made in a protein sequence, and, of course, its underlying DNA coding sequence, and nevertheless obtain a protein with like properties. It is thus contemplated that various changes may be made in the polypeptide sequences of the disclosed compositions, or corresponding DNA sequences which encode said polypeptides without appreciable loss of their desired utility or activity.

TABLE 1

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |

TABLE 1-continued

| Amino Acids | | | Codons | | | | | |
|---|---|---|---|---|---|---|---|---|
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In making such changes, the hydropathic index of amino acids may also be considered. The importance of the hydropathic amino acid index in conferring interactive biologic function on a protein is generally understood in the art (Kyte and Doolittle, 1982, incorporated herein by reference). For example, it is known that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain non-conservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on secondary structure and hydropathic nature of the polypeptide.

Polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted, for example, using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 *Methods in Enzymology vol.* 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971)

*Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Nat'l Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Nat'l Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

Examples of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one illustrative approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

In certain embodiments of the invention, there are provided fusion polypeptides, and polynucleotides encoding fusion polypeptides. Fusion polypeptides refer to polypeptides of the invention that have been covalently linked, either directly or indirectly via an amino acid linker, to one or more heterologous polypeptide sequences (fusion partners). The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order.

The fusion partner may be designed and included for essentially any desired purpose provided they do not adversely effect the desired activity of the polypeptide. For example, in one embodiment, a fusion partner comprises a sequence that assists in expressing the protein (an expression enhancer) at higher yields than the native recombinant protein. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques. For example, DNA sequences encoding the polypeptide components of a desired fusion may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures, if desired. Such a peptide linker sequence is incorporated into the fusion protein using standard techniques well known in the art. Certain peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39 46 (1985); Murphy et al., *Proc. Natl. Acad. Sci. USA* 83:8258 8262 (1986); U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located 5' to the DNA sequence encoding the first polypeptides. Similarly, stop codons required to end translation and transcription termination signals are present 3' to the DNA sequence encoding the second polypeptide.

In general, polypeptides and fusion polypeptides (as well as their encoding polynucleotides) are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

In still other embodiments, a polypeptide of the invention may be part of a dimer. Dimers may include, for example, homodimers between two identical AARS polypeptides, heterodimers between two different AARS polypeptides (e.g., a full-length GlyRS polypeptide and a truncated GlyRS polypeptide, or two different truncated AARS polypeptides), and/or heterodimers between an AARS polypeptide and a heterologous polypeptide. The monomers and/or dimers may be soluble and may be isolated or purified to homogeneity. Certain heterodimers, such as those between an AARS polypeptide and a heterologous polypeptide, may be bi-functional.

Also included are monomeric or substantially monomeric proteins. In certain embodiments, a monomeric protein has reduced capacity to dimerize with itself (i.e., homodimerize) and/or dimerize with another AARS polypeptide (i.e., heterodimerize).

In other embodiments, a polypeptide of the invention may be part of a multi-unit complex. A multi-unit complex of the present invention can include, for example, at least 2, 3, 4, or 5 or more monomers. The monomers and/or multi-unit complexes may be soluble and may be isolated or purified to homogeneity. Monomer units of a multi-unit complex may be different, homologous, substantially homologous, or identical to one another. However, a multi-unit complex of the invention includes at least one monomer comprising a polypeptide as described herein or, in other embodiments, at least two or more polypeptides, as described herein.

Covalently linked monomers can be linked directly (by bonds) or indirectly (e.g., via a linker). For directly linking the polypeptide monomers herein, it may be beneficial to modify the polypeptides herein to enhance dimerization or multimerization. For example, one or more amino acid residues of an AARS polypeptide may be modified by the addition or substitution by one or more cysteines. Methods for creating amino acid substitutions, such as cysteine substitutions, or other modifications to facilitate linking, are well known to those skilled in the art.

Certain embodiments of the present invention also contemplate the use of modified AARS or other polypeptides, including modifications that improve desired characteristics of an AARS or other polypeptide, as described herein. Illustrative modifications of AARS polypeptides of the invention include, but are not limited to, chemical and/or enzymatic derivatizations at one or more constituent amino acid, including side chain modifications, backbone modifications, and N- and C-terminal modifications including acetylation, hydroxylation, methylation, amidation, and the attachment of carbohydrate or lipid moieties, cofactors, and the like. Exemplary modifications also include pegylation of polypeptides (see, e.g., Veronese and Harris, *Advanced Drug Delivery Reviews* 54: 453-456, 2002, herein incorporated by reference).

In certain aspects, chemoselective ligation technology may be utilized to modify truncated polypeptides of the invention, such as by attaching polymers in a site-specific and controlled manner. Such technology typically relies on the incorporation of chemoselective anchors into the protein backbone by either chemical or recombinant means, and subsequent modification with a polymer carrying a complementary linker. As a result, the assembly process and the covalent structure of the resulting protein-polymer conjugate may be controlled, enabling the rational optimization of drug properties, such as efficacy and pharmacokinetic properties (see, e.g., Kochendoerfer, *Current Opinion in Chemical Biology* 9:555-560, 2005).

The AARS polypeptides described herein may be prepared by any suitable procedure known to those of skill in the art, such as by recombinant techniques. For example, polypeptides may be prepared by a procedure including the steps of: (a) preparing a construct comprising a polynucleotide sequence that encodes an AARS polypeptide of the invention and that is operably linked to a regulatory element; (b) introducing the construct into a host cell; (c) culturing the host cell to express the polypeptide; and (d) isolating the polypeptide from the host cell. Recombinant AARS polypeptides can be conveniently prepared using standard protocols as described for example in Sambrook, et al., (1989, supra), in particular Sections 16 and 17; Ausubel et al., (1994, supra), in particular Chapters 10 and 16; and Coligan et al., Current Protocols in Protein Science (John Wiley & Sons, Inc. 1995-1997), in particular Chapters 1, 5 and 6.

In addition to recombinant production methods, polypeptides of the invention may be produced by direct peptide synthesis using solid-phase techniques (Merrifield, *J. Am. Chem. Soc.* 85:2149-2154 (1963)). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the desired molecule.

Polynucleotide Compositions

The present invention also provides isolated polynucleotides that encode the polypeptides of the invention, as well as compositions comprising such polynucleotides. For example, polynucleotide sequences encoding tRNA synthetase proteins, and other proteins described herein, are readily available via any of a number of public sequence databases (e.g., http://www.ncbi.nlm.nih.gov) and can be identified, made and used in the context of the present disclosure using techniques and methodologies described herein and/or well established in the art.

As used herein, the terms "DNA" and "polynucleotide" and "nucleic acid" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the polynucleotide sequences of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be recognized by the skilled artisan, polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a polypeptide of the invention or a portion thereof) or may comprise a variant, or a biological functional equivalent of such a sequence. Polynucleotide variants may contain one or more substitutions, additions, deletions and/or insertions, as further described below, preferably such that the desired activity of the encoded polypeptide is not substantially diminished relative to the unmodified polypeptide. The effect on the activity of the encoded polypeptide may generally be assessed as described herein.

In additional embodiments, the present invention provides isolated polynucleotides comprising various lengths of contiguous stretches of sequence identical to or complementary a polynucleotide encoding a polypeptide as described herein.

For example, polynucleotides are provided by this invention that encode at least about 5, 10, 15, 20, 25, 50, 75, 100, 150, 200, 250, 300, 350, 400, 450 or 500, or more, contiguous amino acid residues of a polypeptide of the invention, as well as all intermediate lengths. It will be readily understood that "intermediate lengths", in this context, means any length between the quoted values, such as 101, 102, 103, etc.; 151, 152, 153, etc.; 201, 202, 203, etc.

The polynucleotides of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a polynucleotide fragment of almost any length may be employed, with the total length preferably being limited by the ease of preparation and use in the intended recombinant DNA protocol.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention, for example polynucleotides that are optimized for human and/or primate codon selection. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides and fusions thereof may be prepared, manipulated and/or expressed using any of a variety of well established techniques known and available in the art. For example, polynucleotide sequences which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, expression and/or activity of the gene product.

In order to express a desired polypeptide, a nucleotide sequence encoding the polypeptide, or a functional equivalent, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (1989), and Ausubel et al., Current Protocols in Molecular Biology (1989).

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced; pIN vectors (Van Heeke & Schuster, *J. Biol. Chem.* 264:5503 5509 (1989)); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters such as alpha factor, alcohol oxidase, and PGH may be used. For reviews, see Ausubel et al. (supra) and Grant et al., *Methods Enzymol.* 153:516-544 (1987).

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, *EMBO J.* 6:307-311 (1987)). Alternatively, plant promoters such as the small subunit of RUBISCO or heat shock promoters may be used (Coruzzi et al., *EMBO J.* 3:1671-1680 (1984); Broglie et al., *Science* 224:838-843 (1984); and Winter et al., *Results Probl. Cell Differ.* 17:85-105 (1991)). These constructs can be introduced into plant cells by direct DNA transformation or pathogen-mediated transfection. Such techniques are described in a number of generally available reviews (see, e.g., Hobbs in McGraw Hill, *Yearbook of Science and Technology*, pp. 191-196 (1992)).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia larvae*. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia larvae* in which the polypeptide of interest may be expressed (Engelhard et al., *Proc. Natl. Acad. Sci. U.S.A.* 91:3224-3227 (1994)).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, Proc. *Natl. Acad. Sci. U.S.A.* 81:3655-3659 (1984)). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf et al., *Results Probl. Cell Differ.* 20:125-162 (1994)).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., *Cell* 11:223-232 (1977)) and adenine phosphoribosyltransferase (Lowy et al., *Cell* 22:817-823 (1990)) genes which can be employed in tk- or aprt-cells, respectively. Also, antimetabolite, antibiotic or herbicide resistance can be used as the basis for selection; for example, dhfr which confers resistance to methotrexate (Wigler et al., *Proc. Natl. Acad. Sci. U.S.A.* 77:3567-70 (1980)); npt, which confers resistance to the aminoglycosides, neomycin and G-418 (Colbere-Garapin et al., *J. Mol. Biol.* 150:1-14 (1981)); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman & Mulligan, *Proc. Natl. Acad. Sci. U.S.A.* 85:8047-51 (1988)). The use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes et al., *Methods Mol. Biol.* 55:121-131 (1995)).

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). These and other assays are described, among other places, in Hampton et al., *Serological Methods, a Laboratory Manual* (1990) and Maddox et al., *J. Exp. Med.* 158:1211-1216 (1983).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins.

In addition to recombinant production methods, polypeptides of the invention, and fragments thereof, may be produced by direct peptide synthesis using solid-phase techniques (Merrifield, *J. Am. Chem. Soc.* 85:2149-2154 (1963)). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

According to another aspect of the invention, polynucleotides encoding polypeptides of the invention may be delivered to a subject in vivo, e.g., using gene therapy techniques. Gene therapy refers generally to the transfer of heterologous nucleic acids to the certain cells, target cells, of a mammal, particularly a human, with a disorder or conditions for which such therapy is sought. The nucleic acid is introduced into the selected target cells in a manner such that the heterologous DNA is expressed and a therapeutic product encoded thereby is produced.

Various viral vectors that can be utilized for gene therapy as taught herein include adenovirus, herpes virus, vaccinia, adeno-associated virus (AAV), or, preferably, an RNA virus such as a retrovirus. Preferably, the retroviral vector is a derivative of a murine or avian retrovirus, or is a lentiviral vector. The preferred retroviral vector is a lentiviral vector. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of additional retroviral vectors can incorporate multiple genes. All of these vectors can transfer or incorporate a gene for a selectable marker so that transduced cells can be identified and generated. By inserting a zinc finger derived-DNA binding polypeptide sequence of interest into the viral vector, along with another gene that encodes the ligand for a receptor on a specific target cell, for example, the vector may be made target specific. Retroviral vectors can be made target specific by inserting, for example, a polynucleotide encoding a protein (dimer). Illustrative targeting may be accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the zinc finger-nucleotide binding protein polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsulation. Helper cell lines which have deletions of the packaging signal include but are not limited to PSI.2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. The vector virions produced by this method can then be used to infect a tissue cell line, such as NIH 3T3 cells, to produce large quantities of chimeric retroviral virions.

"Non-viral" delivery techniques for gene therapy can also be used including, for example, DNA-ligand complexes, adenovirus-ligand-DNA complexes, direct injection of DNA, $CaPO_4$ precipitation, gene gun techniques, electroporation, liposomes, lipofection, and the like. Any of these methods are widely available to one skilled in the art and would be suitable for use in the present invention. Other suitable methods are available to one skilled in the art, and it is to be understood that the present invention can be accomplished using any of the available methods of transfection. Lipofection can be accomplished by encapsulating an isolated DNA molecule within a liposomal particle and contacting the liposomal particle with the cell membrane of the target cell. Liposomes are self-assembling, colloidal particles in which a lipid bilayer, composed of amphiphilic molecules such as phosphatidyl serine or phosphatidyl choline, encapsulates a portion of the surrounding media such that the lipid bilayer surrounds a hydrophilic interior. Unilammellar or multilammellar liposomes can be constructed such that the interior contains a desired chemical, drug, or, as in the instant invention, an isolated DNA molecule.

Embodiments of the present invention also include oligonucleotides (e.g., antisense oligomers, probes, primers), whether for detection, amplification, antisense therapies, or other purpose. Oligonucleotides typically comprise or are complementary to at least a portion of an AARS polynucleotide sequence. For these and related purposes, the term "oligonucleotide" or "oligo" or "oligomer" is intended to encompass a singular "oligonucleotide" as well as plural "oligonucleotides," and refers to any polymer of two or more of nucleotides, nucleosides, nucleobases or related compounds used as a reagent in the amplification methods of the present invention, as well as subsequent detection methods. The oligonucleotide may be DNA and/or RNA and/or analogs thereof.

In certain embodiments, oligomers such as antisense oligomers as long as 40 bases may be suitable, where at least a minimum number of bases, e.g., 10-12 bases, are complementary to the target sequence (e.g., an AARS polynucleotide sequence). In general, however, facilitated or active uptake in cells is optimized at oligomer lengths less than about 30. For certain oligomers, described further below, an optimum balance of binding stability and uptake generally occurs at lengths of 18-25 bases. Included are antisense oligomers (e.g., PNAs, LNAs, 2'-OMe, MOE, morpholinos) that consist of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases, in which at least about 6, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 contiguous or non-contiguous bases are complementary to their AARS target sequence, or variants thereof.

Certain embodiments relate to RNA interference (RNAi) agents, such as short-interfering RNA (siRNA) or other siRNA agents, that target one or more mRNA transcripts of an AARS polynucleotide. For certain siRNA-related embodiments, each strand of an siRNA agent can be equal to or less than 35, 30, 25, 24, 23, 22, 21, 20, 19, 18, 17, 16, or 15 nucleotides in length. The strand is preferably at least 19 nucleotides in length. For example, each strand can be between 21 and 25 nucleotides in length. Preferred siRNA agents have a duplex region of 17, 18, 19, 29, 21, 22, 23, 24, or 25 nucleotide pairs, and one or more overhangs, preferably one or two 3' overhangs, of 2-3 nucleotides. Also included are methods of use thereof to modulate the levels of a selected AARS transcript, such as an AARS polynucleotide that encodes a motif as described herein.

As noted above, the AARS polynucleotides of the present invention can be used in any of the diagnostic, drug discovery, or therapeutic methods described herein.

Antibody Compositions, Fragments Thereof and Other Binding Agents

According to another aspect, the present invention further provides binding agents, such as antibodies and antigen-binding fragments thereof, soluble receptors, peptides, peptide mimetics, aptamers, etc., that exhibit binding specificity for a polypeptide disclosed herein, or to a portion, variant or derivative thereof, and methods of using same. Also included are binding agents that exhibit binding specificity for a cellular binding partner of a polypeptide disclosed herein. Preferably, such binding agents are effective for modulating one or more of the non-canonical activities mediated by a polypeptide of the invention.

In certain embodiments, for example, the binding agent is one that binds to a polypeptide of the invention and inhibits its ability to bind to one or more of its cellular binding partners. Accordingly, such binding agents may be used to treat or prevent diseases, disorders or other conditions that are mediated by a polypeptide of the invention by antagonizing its activity.

An antibody, or antigen-binding fragment thereof, is said to "specifically bind," "immunogically bind," and/or is "immunologically reactive" to a polypeptide of the invention if it reacts at a detectable level (within, for example, an ELISA assay) with the polypeptide, and does not react detectably with unrelated polypeptides under similar conditions.

Immunological binding, as used in this context, generally refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($k_{on}$) and the "off rate constant" ($k_{off}$) can be determined by calculation of the concentrations and the actual rates of association and dissociation. The ratio of $k_{off}/k_{on}$ enables cancellation of all parameters not related to affinity, and is thus equal to the dissociation constant $K_d$. See, generally, Davies et al. (1990) Annual Rev. Biochem. 59:439-473.

An "antigen-binding site," or "binding portion" of an antibody refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

A binding agent may be, for example, a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for a polypeptide of interest may be prepared, for example, using the technique of Kohler and Milstein, Eur. J. Immunol. 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of therapeutically useful molecules are known in the art which comprise antigen-binding sites that are capable of exhibiting immunological binding properties of an antibody molecule. The proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab')$_2$" fragment which comprises both antigen-binding sites. An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. Inbar et al. (1972) Proc. Nat. Acad. Sci. USA 69:2659-2662; Hochman et al. (1976) Biochem 15:2706-2710; and Ehrlich et al. (1980) Biochem 19:4091-4096.

A single chain Fv ("sFv") polypeptide is a covalently linked $V_H$::$V_L$ heterodimer which is expressed from a gene fusion including $V_H$- and $V_L$-encoding genes linked by a peptide-encoding linker. Huston et al. (1988) Proc. Nat. Acad. Sci. USA 85(16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRS and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRS. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

A number of "humanized" antibody molecules comprising an antigen-binding site derived from a non-human immunoglobulin have been described, including chimeric antibodies having rodent V regions and their associated CDRs fused to human constant domains (Winter et al. (1991) Nature 349:293-299; Lobuglio et al. (1989) Proc. Nat. Acad. Sci. USA 86:4220-4224; Shaw et al. (1987) J Immunol. 138:4534-4538; and Brown et al. (1987) Cancer Res. 47:3577-3583), rodent CDRs grafted into a human supporting FR prior to fusion with an appropriate human antibody constant domain (Riechmann et al. (1988) Nature 332:323-327; Verhoeyen et al. (1988) Science 239:1534-1536; and Jones et al. (1986) Nature 321:522-525), and rodent CDRs supported by recombinantly veneered rodent FRs (European Patent Publication No. 519,596, published Dec. 23, 1992). These "humanized" molecules are designed to minimize unwanted immunological response toward rodent antibody molecules which limits the duration and effectiveness of therapeutic applications of those moieties in human recipients.

As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site which retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface. Davies et al. (1990) Ann. Rev. Biochem. 59:439-473. Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

In another embodiment of the invention, monoclonal antibodies or other binding agents of the present invention may be coupled to one or more agents of interest. For example, a therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used.

As noted above, "peptides" are included as binding agents. The term peptide typically refers to a polymer of amino acid residues and to variants and synthetic analogues of the same. In certain embodiments, the term "peptide" refers to relatively short polypeptides, including peptides that consist of about 2, 3, 4, 5, 6, 7, 8, 9, 10, 11, 12, 13, 14, 15, 16, 17, 18, 19, 20, 25, 30, 35, 40, 45, or 50 amino acids, including all integers and ranges (e.g., 5-10, 8-12, 10-15) in between, and interact with an AARS polypeptide, its cellular binding partner, or both. Peptides can be composed of naturally-occurring amino acids and/or non-naturally occurring amino acids, as described herein.

A binding agent may include a peptide mimetic or other small molecule. A "small molecule" refers to an organic compound that is of synthetic or biological origin (biomolecule), but is typically not a polymer. Organic compounds refer to a large class of chemical compounds whose molecules contain carbon, typically excluding those that contain only carbonates, simple oxides of carbon, or cyanides. A "biomolecule" refers generally to an organic molecule that is produced by a living organism, including large polymeric molecules (biopolymers) such as peptides, polysaccharides, and nucleic acids as well, and small molecules such as primary secondary metabolites, lipids, phospholipids, glycolipids, sterols, glycerolipids, vitamins, and hormones. A "polymer" refers generally to a large molecule or macromolecule composed of repeating structural units, which are typically connected by covalent chemical bond.

In certain embodiments, a small molecule has a molecular weight of less than 1000 Daltons, typically between about 300 and 700 Daltons, and including about 50, 100, 150, 200, 250, 300, 350, 400, 450, 500, 550, 500, 650, 600, 750, 700, 850, 800, 950, or 1000 Daltons.

Aptamers are also included as binding agents. Examples of aptamers included nucleic acid aptamers (e.g., DNA aptamers, RNA aptamers) and peptide aptamers. Nucleic acid aptamers refer generally to nucleic acid species that have been engineered through repeated rounds of in vitro selection or equivalent method, such as SELEX (systematic evolution of ligands by exponential enrichment), to bind to various molecular targets such as small molecules, proteins, nucleic acids, and even cells, tissues and organisms. Hence, included are nucleic acid aptamers that bind to the AARS polypeptides described herein and/or their cellular binding partners.

Peptide aptamers typically include a variable peptide loop attached at both ends to a protein scaffold, a double structural constraint that typically increases the binding affinity of the peptide aptamer to levels comparable to that of an antibody's (e.g., in the nanomolar range). In certain embodiments, the variable loop length may be composed of about 10-20 amino acids (including all integers in between), and the scaffold may include any protein that has good solubility and compacity properties. Certain exemplary embodiments may utilize the bacterial protein Thioredoxin-A as a scaffold protein, the variable loop being inserted within the reducing active site (-Cys-Gly-Pro-Cys-loop in the wild protein), with the two cysteines lateral chains being able to form a disulfide bridge. Hence, included are peptide aptamers that bind to the AARS polypeptides described herein and/or their cellular binding partners. Peptide aptamer selection can be performed using different systems known in the art, including the yeast two-hybrid system.

As noted above, the AARS polypeptides and binding agents of the present invention can be used in any of the diagnostic, drug discovery, or therapeutic methods described herein.

Formulation and Administration

The compositions of the invention (e.g., polypeptides, polynucleotides, antibodies, etc.) are generally formulated in pharmaceutically-acceptable or physiologically-acceptable solutions for administration to a cell, tissue or animal, either alone, or in combination with one or more other modalities of therapy. It will also be understood that, if desired, the compositions of the invention may be administered in combination with other agents as well, such as, e.g., other proteins or polypeptides or various pharmaceutically-active agents. There is virtually no limit to other components that may also be included in the compositions, provided that the additional agents do not adversely affect properties of a polypeptide of the invention.

In the pharmaceutical compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, intracranial and intramuscular administration and formulation.

In certain applications, the pharmaceutical compositions disclosed herein may be delivered via oral administration to a subject. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the pharmaceutical compositions disclosed herein parenterally, intravenously, intramuscularly, or even intraperitoneally as described, for example, in U.S. Pat. No. 5,543,158; U.S. Pat. No. 5,641,515 and U.S. Pat. No. 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., *Remington's Pharmaceutical Sciences*, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions can be prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

In certain embodiments, the pharmaceutical compositions may be delivered by intranasal sprays, inhalation, and/or other aerosol delivery vehicles. Methods for delivering genes, polynucleotides, and peptide compositions directly to the lungs via nasal aerosol sprays has been described e.g., in U.S. Pat. No. 5,756,353 and U.S. Pat. No. 5,804,212 (each specifically incorporated herein by reference in its entirety). Likewise, the delivery of drugs using intranasal microparticle resins (Takenaga et al., 1998) and lysophosphatidylglycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

In certain embodiments, the delivery may occur by use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

Kits Comprising Compositions of the Invention

The invention, in other aspects, provides kits comprising one or more containers filled with one or more of the polypeptides, polynucleotides, antibodies, multiunit complexes, compositions thereof, etc., of the invention, as described herein. The kits can include written instructions on how to use such compositions (e.g., to modulate cellular signaling, angiogenesis, cancer, inflammatory conditions, etc.).

The kits herein may also include a one or more additional therapeutic agents or other components suitable or desired for the indication being treated. An additional therapeutic agent may be contained in a second container, if desired. Examples of additional therapeutic agents include, but are not limited to antineoplastic agents, anti-inflammatory agents, antibacterial agents, antiviral agents, angiogenic agents, etc.

The kits herein can also include one or more syringes or other components necessary or desired to facilitate an intended mode of delivery (e.g., stents, implantable depots, etc.).

Methods of Use

Embodiments of the present invention also include methods of using the aminoacyl-tRNA (AARS) "agents" described herein for diagnostic, drug discovery, and/or therapeutic purposes. The term AARS "agents" refers generally to the AARS polynucleotides, AARS polypeptides, binding agents such as peptide mimetics, and other compounds described herein. For diagnostic purposes, the AARS agents can be used in a variety of non-limiting ways, such as to distinguish between different cell types or different cellular states, or to identify subjects having a relevant disease or condition. For drug discovery purposes, the AARS agents can be used to identify one or more cellular "binding partners" of an AARS polypeptide, characterize one or more "non-canonical" activities of an AARS polypeptide, identify agents that selectively or non-selectively agonize or antagonize the interaction of an AARS polypeptide with its binding partner(s), and/or identify agents that selectively or non-selectively agonize or antagonize one or more "non-canonical" activities of an AARS polypeptide. For therapeutic purposes, the AARS agents or compositions provided herein can be used to treat a variety of diseases or conditions, detailed below.

Drug Discovery

Certain embodiments relate to the use of the aminoacyl-tRNA synthetase (AARS) polypeptide sequences described herein in drug discovery, typically to identify agents that modulate one or more of the non-canonical activities of the polypeptide. For example, certain embodiments include methods of identifying one or more "binding partners" of an AARS polypeptide of the present invention, such as a cellular protein or other host molecule that associates with the polypeptide and participates in its non-canonical activity or activities. Also included are methods of identifying a compound (e.g., polypeptide) or other agent that agonizes or antagonizes the non-canonical activity of a reference polypeptide or active variant thereof, such as by interacting with the polypeptide and/or one or more of its cellular binding partners.

Certain embodiments therefore include methods of identifying a binding partner of an AARS polypeptide, comprising a) combining the AARS polypeptide with a biological sample under suitable conditions, and b) detecting specific binding of the AARS polypeptide to a binding partner, thereby identifying a binding partner that specifically binds to the AARS polypeptide. Also included are methods of screening for a compound that specifically binds to an AARS polypeptide or a binding partner of the polypeptide, comprising a) combining the polypeptide or the binding partner with at least one test compound under suitable conditions, and b) detecting binding of the polypeptide or the binding partner to the test compound, thereby identifying a compound that specifically binds to the polypeptide or its binding partner. In certain embodiments, the compound is a polypeptide or peptide. In certain embodiments, the compound is a small molecule or other (e.g., non-biological) chemical compound. In certain embodiments, the compound is a peptide mimetic.

Any method suitable for detecting protein-protein interactions may be employed for identifying cellular proteins that interact with an AARS polypeptide, interact with one or more of its cellular binding partners, or both. Examples of traditional methods that may be employed include co-immunoprecipitation, cross-linking, and co-purification through gradients or chromatographic columns of cell lysates or proteins obtained from cell lysates, mainly to identify proteins in the lysate that interact with the AARS polypeptide.

In these and related embodiments, at least a portion of the amino acid sequence of a protein that interacts with an AARS polypeptide or its binding partner can be ascertained using techniques well known to those of skill in the art, such as via the Edman degradation technique. See, e.g., Creighton Proteins: Structures and Molecular Principles, W. H. Freeman & Co., N.Y., pp. 34 49, 1983. The amino acid sequence obtained may be used as a guide for the generation of oligonucleotide mixtures that can be used to screen for gene sequences encoding such proteins. Screening may be accomplished, for example, by standard hybridization or PCR techniques, as described herein and known in the art. Techniques for the generation of oligonucleotide mixtures and the screening are well known. See, e.g., Ausubel et al. Current Protocols in Molecular Biology Green Publishing Associates and Wiley Interscience, N.Y., 1989; and Innis et al., eds. PCR Protocols: A Guide to Methods and Applications Academic Press, Inc., New York, 1990.

Additionally, methods may be employed in the simultaneous identification of genes that encode the binding partner or other polypeptide. These methods include, for example, probing expression libraries, in a manner similar to the well known technique of antibody probing of lambda-gt11 libraries, using labeled AARS protein, or another polypeptide, peptide or fusion protein, e.g., a variant AARS polypeptide or AARS domain fused to a marker (e.g., an enzyme, fluor, luminescent protein, or dye), or an Ig-Fc domain.

One method that detects protein interactions in vivo, the two-hybrid system, is described in detail for illustration only and not by way of limitation. One example of this system has been described (Chien et al., PNAS USA 88:9578 9582, 1991) and is commercially available from Clontech (Palo Alto, Calif.).

Briefly, utilizing such a system, plasmids may be constructed that encode two hybrid proteins: one plasmid consists of nucleotides encoding the DNA-binding domain of a transcription activator protein fused to an AARS reference nucleotide sequence (or, in certain embodiments, its binding partner), or a variant thereof, and the other plasmid consists of nucleotides encoding the transcription activator protein's activation domain fused to a cDNA (or collection of cDNAs) encoding an unknown protein(s) that has been recombined into the plasmid as part of a cDNA library. The DNA-binding domain fusion plasmid and the activator cDNA library may be transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or other such methodology may be used to screen activation domain libraries for proteins that interact with the "bait" gene product. By way of example, and not by way of limitation, an AARS reference polypeptide or variant may be used as the bait gene product. An AARS binding partner may also be used as a "bait" gene product. Total genomic or cDNA sequences are fused to the DNA encoding an activation domain. This library and a plasmid encoding a hybrid of a bait AARS gene product fused to the DNA-binding domain are co-transformed into a yeast reporter strain, and the resulting transformants are screened for those that express the reporter gene.

A cDNA library of the cell line from which proteins that interact with bait AARS gene products are to be detected can be made using methods routinely practiced in the art. For example, the cDNA fragments can be inserted into a vector such that they are translationally fused to the transcriptional activation domain of GAL4. This library can be co-transformed along with the bait gene-GAL4 fusion plasmid into a yeast strain, which contains a lacZ gene driven by a promoter that contains GAL4 activation sequence. A cDNA encoded protein, fused to GAL4 transcriptional activation domain, that interacts with bait gene product will reconstitute an active GAL4 protein and thereby drive expression of the HIS3 gene. Colonies, which express HIS3, can be detected by their growth on Petri dishes containing semi-solid agar based media lacking histidine. The cDNA can then be purified from these strains, and used to produce and isolate the bait AARS gene-interacting protein using techniques routinely practiced in the art.

Also included are three-hybrid systems, which allow the detection of RNA-protein interactions in yeast. See, e.g., Hook et al., *RNA*. 11:227-233, 2005. Accordingly, these and related methods can be used to identify a cellular binding partner of an AARS polypeptide, and to identify other proteins or nucleic acids that interact with the AARS polypeptide, the cellular binding partner, or both.

As noted above, once isolated, binding partners can be identified and can, in turn, be used in conjunction with standard techniques to identify proteins or other compounds with which it interacts. Certain embodiments thus relate to methods of screening for a compound that specifically binds to the binding partner of an AARS reference polypeptide, comprising a) combining the binding partner with at least one test compound under suitable conditions, and b) detecting binding of the binding partner to the test compound, thereby identifying a compound that specifically binds to the binding partner. In certain embodiments, the test compound is a polypeptide. In certain embodiments, the test compound is a chemical compound, such as a small molecule compound or peptide mimetic.

Certain embodiments include methods of screening for a compound that modulates the activity of an AARS polypeptide, comprising a) combining the polypeptide with at least one test compound under conditions permissive for the activity of the polypeptide, b) assessing the activity of the polypeptide in the presence of the test compound, and c) comparing the activity of the polypeptide in the presence of the test compound with the activity of the polypeptide in the absence of the test compound, wherein a change in the activity of the polypeptide in the presence of the test compound is indicative of a compound that modulates the activity of the polypeptide. Certain embodiments include methods of screening for a compound that modulates the activity of a binding partner of an AARS polypeptide, comprising a) combining the polypeptide with at least one test compound under conditions permissive for the activity of the binding partner, b) assessing the activity of the binding partner in the presence of the test compound, and c) comparing the activity of the binding partner in the presence of the test compound with the activity of the binding partner in the absence of the test compound, wherein a change in the activity of the binding partner in the presence of the test compound is indicative of a compound that modulates the activity of the binding partner. Typically, these and related embodiments include assessing a selected non-canonical activity that is associated with the AARS polypeptide or its binding partner. Included are in vitro and in vivo conditions, such as cell culture conditions.

Certain embodiments include methods of screening a compound for effectiveness as a full or partial agonist of an AARS polypeptide or an active fragment or variant thereof, comprising a) exposing a sample comprising the polypeptide to a compound, and b) detecting agonist activity in the sample, typically by measuring an increase in the non-canonical activity of the AARS polypeptide. Certain methods include a) exposing a sample comprising a binding partner of the AARS polypeptide to a compound, and b)

detecting agonist activity in the sample, typically by measuring an increase in the selected non-canonical activity of the AARS polypeptide. Certain embodiments include compositions that comprise an agonist compound identified by the method and a pharmaceutically acceptable carrier or excipient.

Also included are methods of screening a compound for effectiveness as a full or partial antagonist of an AARS polypeptide, comprising a) exposing a sample comprising the polypeptide to a compound, and b) detecting antagonist activity in the sample, typically by measuring a decrease in the non-canonical activity of the AARS polypeptide. Certain methods include a) exposing a sample comprising a binding partner of the AARS polypeptide to a compound, and b) detecting antagonist activity in the sample, typically by measuring a decrease in the selected non-canonical activity of the AARS polypeptide. Certain embodiments include compositions that comprise an antagonist compound identified by the method and a pharmaceutically acceptable carrier or excipient.

In certain embodiments, in vitro systems may be designed to identify compounds capable of interacting with or modulating an AARS reference sequence or its binding partner. Certain of the compounds identified by such systems may be useful, for example, in modulating the activity of the pathway, and in elaborating components of the pathway itself. They may also be used in screens for identifying compounds that disrupt interactions between components of the pathway; or may disrupt such interactions directly. One exemplary approach involves preparing a reaction mixture of the AARS polypeptide and a test compound under conditions and for a time sufficient to allow the two to interact and bind, thus forming a complex that can be removed from and/or detected in the reaction mixture In vitro screening assays can be conducted in a variety of ways. For example, an AARS polypeptide, a cellular binding partner, or test compound(s) can be anchored onto a solid phase. In these and related embodiments, the resulting complexes may be captured and detected on the solid phase at the end of the reaction. In one example of such a method, the AARS polypeptide and/or its binding partner are anchored onto a solid surface, and the test compound(s), which are not anchored, may be labeled, either directly or indirectly, so that their capture by the component on the solid surface can be detected. In other examples, the test compound(s) are anchored to the solid surface, and the AARS polypeptide and/or its binding partner, which are not anchored, are labeled or in some way detectable. In certain embodiments, microtiter plates may conveniently be utilized as the solid phase. The anchored component (or test compound) may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

To conduct an exemplary assay, the non-immobilized component is typically added to the coated surface containing the anchored component. After the reaction is complete, un-reacted components are removed (e.g., by washing) under conditions such that any specific complexes formed will remain immobilized on the solid surface. The detection of complexes anchored on the solid surface can be accomplished in a number of ways. For instance, where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Alternatively, the presence or absence of binding of a test compound can be determined, for example, using surface plasmon resonance (SPR) and the change in the resonance angle as an index, wherein an AARS polypeptide or a cellular binding partner is immobilized onto the surface of a commercially available sensorchip (e.g., manufactured by Biacore™) according to a conventional method, the test compound is contacted therewith, and the sensorchip is illuminated with a light of a particular wavelength from a particular angle. The binding of a test compound can also be measured by detecting the appearance of a peak corresponding to the test compound by a method wherein an AARS polypeptide or a cellular binding partner is immobilized onto the surface of a protein chip adaptable to a mass spectrometer, a test compound is contacted therewith, and an ionization method such as MALDI-MS, ESI-MS, FAB-MS and the like is combined with a mass spectrometer (e.g., double-focusing mass spectrometer, quadrupole mass spectrometer, time-of-flight mass spectrometer, Fourier transformation mass spectrometer, ion cyclotron mass spectrometer and the like).

In certain embodiments, cell-based assays, membrane vesicle-based assays, or membrane fraction-based assays can be used to identify compounds that modulate interactions in the non-canonical pathway of the selected AARS polypeptide. To this end, cell lines that express an AARS polypeptide and/or a binding partner, or a fusion protein containing a domain or fragment of such proteins (or a combination thereof), or cell lines (e.g., COS cells, CHO cells, HEK293 cells, Hela cells etc.) that have been genetically engineered to express such protein(s) or fusion protein(s) can be used. Test compound(s) that influence the non-canonical activity can be identified by monitoring a change (e.g., a statistically significant change) in that activity as compared to a control or a predetermined amount.

For embodiments that relate to antisense and RNAi agents, for example, also included are methods of screening a compound for effectiveness in altering expression of an AARS polynucleotide sequence, comprising a) exposing a sample comprising the AARS polynucleotide to a compound such as a potential antisense oligonucleotide, and b) detecting altered expression of the AARS polynucleotide. In certain non-limiting examples, these and related embodiments can be employed in cell-based assays or in cell-free translation assays, according to routine techniques in the art. Also included are the antisense oligonucleotides and RNAi agents identified by such methods.

Also included are any of the above methods, or other screening methods known in the art, which are adapted for high-throughput screening (HTS). HTS typically uses automation to run a screen of an assay against a library of candidate compounds, for instance, an assay that measures an increase or a decrease in a non-canonical activity, as described herein.

Methods of Treatment

In another aspect, the present invention relates to methods of using the compositions of the present invention for treating a cell, tissue or subject with a composition as described herein. The cells or tissues that may be modulated by the present invention are preferably mammalian cells or tissues, or more preferably human cells or tissues. Such cells or tissues can be of a healthy state or of a diseased state.

In certain embodiments, for example, methods are provided for modulating therapeutically relevant cellular activities including, but not limited to, cellular metabolism, cell differentiation, cell proliferation, cell death, cell mobilization, cell migration, gene transcription, mRNA translation, cell impedence, and the like, comprising contacting a cell with a composition as described herein. Examples of cells or tissues that may be modulated include those of the skin (e.g., dermis, epidermis, subcutaneous layer), hair follicles, nervous system (e.g., brain, spinal cord, peripheral nerves), auditory system or balance organs (e.g., inner ear, middle ear, outer ear), respiratory system (e.g., nose, trachea, lungs), gastroesophageal tissues, the gastrointestinal system (e.g., mouth, esophagus, stomach, small intestines, large intestines, rectum), vascular system (e.g., heart, blood vessels and arteries), liver, gallbladder, lymphatic/immune system (e.g., lymph nodes, lymphoid follicles, spleen, thymus, bone marrow), uro-genital system (e.g., kidneys, ureter, bladder, urethra, cervix, Fallopian tubes, ovaries, uterus, vulva, prostate, bulbourethral glands, epidiymis, prostate, seminal vesicles, testicles), musculoskeletal system (e.g., skeletal muscles, smooth muscles, bone, cartilage, tendons, ligaments), adipose tissue, mammaries, and the endocrine system (e.g., hypothalamus, pituitary, thyroid, pancreas, adrenal glands). Accordingly, the compositions may be employed in treating essentially any cell or tissue or subject that would benefit from modulation of one or more such exemplary activities, or one or more of such exemplary cells or tissues.

The compositions may also be used in any of a number of therapeutic contexts including, for example, those relating to the treatment or prevention of neoplastic diseases, immune system diseases (e.g., autoimmune diseases and inflammation), infectious diseases, metabolic diseases, neuronal/neurological diseases, muscular/cardiovascular diseases, diseases associated with aberrant hematopoiesis, diseases associated with aberrant angiogenesis, diseases associated with aberrant cell survival, and others.

For example, in certain illustrative embodiments, the compositions of the invention may be used to modulate angiogenesis, e.g., via modulation of endothelial cell proliferation and/or signaling. Endothelial cell proliferation and/or signaling may be monitored using an appropriate cell line (e.g., human microvascular endothelial lung cells (HM-VEC-L) and human umbilical vein endothelial cells (HUVEC)), and using an appropriate assay (e.g., endothelial cell migration assays, endothelial cell proliferation assays, tube-forming assays, matrigel plug assays, etc.), many of which are known and available in the art.

Therefore, in related embodiments, the compositions of the invention may be employed in the treatment of essentially any cell or tissue or subject that would benefit from modulation of angiogenesis. For example, in some embodiments, a cell or tissue or subject experiencing or susceptible to angiogenesis (e.g., an angiogenic condition) may be contacted with a suitable composition of the invention to inhibit an angiogenic condition. In other embodiments, a cell or tissue experiencing or susceptible to insufficient angiogenesis (e.g., an angiostatic condition) may be contacted with an appropriate composition of the invention in order to interfere with angiostatic activity and/or promote angiogenesis.

Illustrative examples of angiogenic conditions include, but are not limited to, age-related macular degeneration (AMD), cancer (both solid and hematologic), developmental abnormalities (organogenesis), diabetic blindness, endometriosis, ocular neovascularization, psoriasis, rheumatoid arthritis (RA), and skin discolorations (e.g., hemangioma, nevus flammeus or nevus simplex). Examples of anti-angiogenic conditions include, but are not limited to, cardiovascular disease, restenosis, tissue damage after reperfusion of ischemic tissue or cardiac failure, chronic inflammation and wound healing.

The compositions of the invention may also be useful as immunomodulators for treating anti- or pro-inflammatory indications by modulating the cells that mediate, either directly or indirectly, autoimmune and/or inflammatory diseases, conditions and disorders. The utility of the compositions of the invention as immunomodulators can be monitored using any of a number of known and available techniques in the art including, for example, migration assays (e.g., using leukocytes or lymphocytes) or cell viability assays (e.g., using B-cells, T-cells, monocytes or NK cells). In certain embodiments, the compositions of the invention may modulate inflammatory cytokines, such as TNF-α. In certain embodiments, the compositions of the invention may modulate chemotaxis of immune cells, such as monocytes.

"Inflammation" refers generally to the biological response of tissues to harmful stimuli, such as pathogens, damaged cells (e.g., wounds), and irritants. The term "inflammatory response" refers to the specific mechanisms by which inflammation is achieved and regulated, including, merely by way of illustration, immune cell activation or migration, cytokine production, vasodilation, including kinin release, fibrinolysis, and coagulation, among others described herein and known in the art. Ideally, inflammation is a protective attempt by the body to both remove the injurious stimuli and initiate the healing process for the affected tissue or tissues. In the absence of inflammation, wounds and infections would never heal, creating a situation in which progressive destruction of the tissue would threaten survival. On the other hand, excessive or chronic inflammation may associate with a variety of diseases, such as hay fever, atherosclerosis, and rheumatoid arthritis, among others described herein and known in the art.

The compositions of the invention may modulate acute inflammation, chronic inflammation, or both. Certain embodiments relate to increasing acute inflammation or acute inflammatory responses, and certain embodiments relate to increasing chronic inflammation or chronic inflammatory responses. Depending on the needs of the subject, certain embodiments relate to reducing acute inflammation or inflammatory responses, and certain embodiments relate to reducing chronic inflammation or chronic inflammatory responses.

Acute inflammation relates to the initial response of the body to presumably harmful stimuli and involves increased movement of plasma and leukocytes from the blood into the injured tissues. It is a short-term process, typically beginning within minutes or hours and ending upon the removal of the injurious stimulus. Acute inflammation may be characterized by any one or more of redness, increased heat, swelling, pain, and loss of function. Redness and heat are due mainly to increased blood flow at body core temperature to the inflamed site, swelling is caused by accumulation of fluid, pain is typically due to release of chemicals that stimulate nerve endings, and loss of function has multiple causes.

Acute inflammatory responses are initiated mainly by local immune cells, such as resident macrophages, dendritic cells, histiocytes, Kuppfer cells and mastocytes. At the onset of an infection, burn, or other injuries, these cells undergo activation and release inflammatory mediators responsible for the clinical signs of inflammation, such as vasoactive amines and eicosanoids. Vasodilation and its resulting increased blood flow cause the redness and increased heat. Increased permeability of the blood vessels results in an exudation or leakage of plasma proteins and fluid into the tissue, which creates swelling. Certain released mediators such as bradykinin increase sensitivity to pain, and alter the blood vessels to permit the migration or extravasation of leukocytes, such as neutrophils, which typically migrate along a chemotactic gradient created by the local immune cells.

Acute inflammatory responses also includes one or more acellular biochemical cascade systems, consisting of preformed plasma proteins modulate, which act in parallel to initiate and propagate the inflammatory response. These systems include the complement system, which is mainly activated by bacteria, and the coagulation and fibrinolysis systems, which are mainly activated by necrosis, such as the type of tissue damage that is caused by certain infections, burns, or other trauma. Hence, the compositions of the invention may be used to modulate acute inflammation, or any of one or more of the individual acute inflammatory responses.

Chronic inflammation, a prolonged and delayed inflammatory response, is characterized by a progressive shift in the type of cells that are present at the site of inflammation, and often leads to simultaneous or near simultaneous destruction and healing of the tissue from the inflammatory process. At the cellular level, chronic inflammatory responses involve a variety of immune cells such as monocytes, macrophages, lymphocytes, plasma cells, and fibroblasts, though in contrast to acute inflammation, which is mediated mainly by granulocytes, chronic inflammation is mainly mediated by mononuclear cells such as monocytes and lymphocytes. Chronic inflammation also involves a variety of inflammatory mediators, such as IFN-γ and other cytokines, growth factors, reactive oxygen species, and hydrolytic enzymes. Chronic inflammation may last for many months or years, and may result in undesired tissue destruction and fibrosis.

Clinical signs of chronic inflammation are dependent upon duration of the illness, inflammatory lesions, cause and anatomical area affected. (see, e.g., Kumar et al., Robbins Basic Pathology-8$^{th}$ Ed., 2009 Elsevier, London; Miller, L M, Pathology Lecture Notes, Atlantic Veterinary College, Charlottetown, PEI, Canada). Chronic inflammation is associated with a variety of pathological conditions or diseases, including, for example, allergies, Alzheimer's disease, anemia, aortic valve stenosis, arthritis such as rheumatoid arthritis and osteoarthritis, cancer, congestive heart failure, fibromyalgia, fibrosis, heart attack, kidney failure, lupus, pancreatitis, stroke, surgical complications, inflammatory lung disease, inflammatory bowel disease, atherosclerosis, and psoriasis, among others described herein and known in the art. Hence, the compositions provided herein may be used to treat or manage chronic inflammation, modulate any of one or more of the individual chronic inflammatory responses, or treat any one or more diseases or conditions associated with chronic inflammation.

The compositions of the invention may also modulate proliferative inflammation, an inflammatory process characterized by an increase in the number of tissue cells. These can encompass skin conditions such as psoriasis, seborrhea or eczema, or can also be thought of in terms of cancers and abnormal growths especially in light of accumulating evidence based on more efficient molecular methods to document even low grade chronic inflammation.

Criteria for assessing the signs and symptoms of inflammatory and other conditions, including for purposes of making differential diagnosis and also for monitoring treatments such as determining whether a therapeutically effective dose has been administered in the course of treatment, e.g., by determining improvement according to accepted clinical criteria, will be apparent to those skilled in the art and are exemplified by the teachings of e.g., Berkow et al., eds., The Merck Manual, 16$^{th}$ edition, Merck and Co., Rahway, N.J., 1992; Goodman et al., eds., Goodman and Gilman's The Pharmacological Basis of Therapeutics, 10$^{th}$ edition, Pergamon Press, Inc., Elmsford, N.Y., (2001); Avery's Drug Treatment: Principles and Practice of Clinical Pharmacology and Therapeutics, 3rd edition, ADIS Press, Ltd., Williams and Wilkins, Baltimore, Md. (1987); Ebadi, Pharmacology, Little, Brown and Co., Boston, (1985); Osolci al., eds., Remington's Pharmaceutical Sciences, 18th edition, Mack Publishing Co., Easton, Pa. (1990); Katzung, Basic and Clinical Pharmacology, Appleton and Lange, Norwalk, Conn. (1992).

Illustrative immune system diseases, disorders or conditions that may be treated according to the present invention include, but are not limited to, primary immunodeficiencies, immune-mediated thrombocytopenia, Kawasaki syndrome, bone marrow transplant (for example, recent bone marrow transplant in adults or children), chronic B cell lymphocytic leukemia, HIV infection (for example, adult or pediatric HIV infection), chronic inflammatory demyelinating polyneuropathy, post-transfusion purpura, and the like.

As noted above, certain embodiments may employ the compositions of the invention to increase inflammation or increase an immune response. For instance, depending on the needs of the subject, certain embodiments may increase acute inflammation or increase acute inflammatory responses or both. Certain embodiments may increase chronic inflammation or chronic inflammatory responses or both. Certain embodiments may increase both acute and chronic inflammation. Certain embodiments may increase local or systemic inflammation or both.

In certain embodiments, compositions may be used to treat or manage immunodeficiencies, including primary immunodeficiencies and secondary immunodeficiencies, in which the body may not mount an adequate inflammatory response. Examples of primary immunodeficiencies include various autosomal recessive and X-linked genetic conditions such as T-cell and B-cell immunodeficiencies, including combined T-cell and B-cell immunodeficiencies, antibody deficiencies, well-defined syndromes, immune dysregulation diseases, phagocyte disorders, innate immunity disorders, and complement deficiencies.

Examples of T-cell and B-cell immunodeficiencies include T−/B+ deficiencies such as γc deficiency, JAK3 deficiency, interleukin 7 receptor chain α deficiency, CD45 deficiency, CD3δ/CD3ε deficiency; and T−/B− deficiencies such as RAG 1/2 deficiency, DCLRE1C deficiency, adenosine deaminase (ADA) deficiency, reticular dysgenesis. Additional examples include Omenn syndrome, DNA ligase type IV deficiency, CD40 ligand deficiency, CD40 deficiency, purine nucleoside phosphorylase (PNP) deficiency, MHC class II deficiency, CD3γ deficiency, CD8 deficiency, ZAP-70 deficiency, TAP-1/2 deficiency, and winged helix deficiency.

Examples of antibody deficiencies include X-linked agammaglobulinemia (btk deficiency, or Bruton's agammaglobulinemia), μ-Heavy chain deficiency, I-5 deficiency, Igα deficiency, BLNK deficiency, thymoma with immunodeficiency, common variable immunodeficiency (CVID), ICOS deficiency, CD19 deficiency, TACI (TNFRSF13B) deficiency, and BAFF receptor deficiency. Additional examples include AID deficiency, UNG deficiency, heavy chain deletions, kappa chain deficiency, isolated IgG subclass deficiency, IgA with IgG subclass deficiency, selective immunoglobulin A deficiency, and transient hypogammaglobulinemia of infancy (THI).

Examples of "well-defined syndromes" include Wiskott-Aldrich syndrome, ataxia telangiectasia, ataxia-like syndrome, Nijmegen breakage syndrome, Bloom syndrome, DiGeorge syndrome, immuno-osseous dysplasias such as cartilage-hair hypoplasia, Schimke syndrome, Hermansky-Pudlak syndrome type 2, Hyper-IgE syndrome, chronic mucocutaneous candidiasis.

Examples of immune dysregulation diseases include immunodeficiency with hypopigmentation or albinism such as Chediak-Higashi syndrome and Griscelli syndrome type 2, familial hemophagocytic lymphohistiocytosis such as perforin deficiency, MUNC13D deficiency, and syntaxin 11 deficiency, X-linked lymphoproliferative syndrome, autoimmune lymphoproliferative syndrome such as type 1a (CD95 defects), type 1b (Fas ligand defects), type 2a (CASP10 defects), and type 2b (CASP8 defects), autoimmune polyendocrinopathy with candidiasis and ectodermal dystrophy, and immunodysregulation polyendocrinopathy enteropathy X-linked syndrome. Additionally, diseases affecting the bone marrow may result in abnormal or few leukocytes, such as leukopenia. Leukopenia can be induced by certain infections and diseases, including viral infection, *Rickettsia* infection, some protozoa, tuberculosis, and certain cancers Examples of phagocyte disorders include severe congenital neutropenia such as ELA2 deficiency (e.g., with myelodysplasia), GFI1 deficiency (with T/B lymphopenia) or G-CSFR deficiency (G-CSF-unresponsive), Kostmann syndrome, cyclic neutropenia, X-linked neutropenia/myelodysplasia, leukocyte adhesion deficiency types 1, 2 and 3, RAC2 deficiency, β-actin deficiency, localized juvenile periodontitis, Papillon-Lefèvre syndrome, specific granule deficiency, Shwachman-Diamond syndrome, chronic granulomatous disease, including X-linked and autosomal forms, neutrophil glucose-6-phosphate dehydrogenase deficiency, IL-12 and IL-23 β1 chain deficiency, IL-12p40 deficiency, interferon γ receptor 1 deficiency, interferon γ receptor 2 deficiency, and STAT1 deficiency.

Examples of innate immunity deficiencies include hypohidrotic ectodermal dysplasia such as NEMO deficiency and IKBA deficiency, IRAK-4 deficiency, WHIM syndrome (warts, hypogammaglobulinaemia, infections, myleokathexis), and epidermodysplasia verruciformis. Examples of complement deficiencies and examplary associated conditions include C1q deficiency (e.g., lupus-like syndrome, rheumatoid disease, infections), C1r deficiency, C4 deficiency, C2 deficiency (e.g., lupus-like syndrome, vasculitis, polymyositis, pyogenic infections), C3 deficiency (e.g., recurrent pyogenic infections), C5 deficiency (e.g., neisserial infections), C6 deficiency, C7 deficiency (e.g., vasculitis), C8a and C8b deficiency, C9 deficiency (e.g., neisserial infections), C1-inhibitor deficiency (e.g., hereditary angioedema), Factor I deficiency (pyogenic infections), Factor H deficiency (e.g., haemolytic-uraemic syndrome, membranoproliferative glomerulonephritis), Factor D deficiency (e.g., neisserial infections), Properdin deficiency (e.g., neisserial infections), MBP deficiency (e.g., pyogenic infections), and MASP2 deficiency.

Primary immune deficiencies can be diagnosed according to routine techniques in the art. Exemplary diagnostic tests include, without limitation, performing counts of the different types of mononuclear cells in the blood (e.g., lymphocytes and monocytes, including lymphocytes, different groups of B lymphocytes such as CD19+, CD20+, and CD21+lymphocytes, natural killer cells, and monocytes positive for CD15+), measuring the presence of activation markers (e.g., HLA-DR, CD25, CD80), performing tests for T cell function such as skin tests for delayed-type hypersensitivity, cell responses to mitogens and allogeneic cells, cytokine production by cells, performing tests for B cell function such as by identifying antibodies to routine immunizations and commonly acquired infections and by quantifying IgG subclasses, and performing tests or phagocyte function, such as by measuring the reduction of nitro blue tetrazolium chloride, and performing assays of chemotaxis and bactericidal activity. AARS polypeptides may therefore be used to stimulate or maintain acute inflammation or acute inflammatory responses in subjects with a primary immunodeficiency, as described herein and known in the art.

Examples of causes of secondary immunodeficiencies include malnutrition, aging, and medications (e.g., chemotherapy, disease-modifying anti-rheumatic drugs, immunosuppressive drugs after organ transplants, glucocorticoids). Additional causes include various cancers, including cancers of the bone marrow and blood cells (e.g., leukemia, lymphoma, multiple myeloma), and certain chronic infections, such as acquired immunodeficiency syndrome (AIDS), caused by the human immunodeficiency virus (HIV). AARS polypeptides may be used to stimulate or maintain acute inflammation or acute inflammatory responses in subjects with an immunodeficiency, as described herein and known in the art. AARS polypeptides may also be used to stimulate or maintain chronic inflammation or chronic inflammatory responses in subjects with a secondary immunodeficiency, as described herein and known in the art.

Additionally, further diseases, disorders and conditions include Guillain-Barre syndrome, anemia (for example, anemia associated with parvovirus B19, patients with stable multiple myeloma who are at high risk for infection (for example, recurrent infection), autoimmune hemolytic anemia (for example, warm-type autoimmune hemolytic anemia), thrombocytopenia (for example, neonatal thrombocytopenia), and immune-mediated neutropenia, transplantation (for example, cytomegalovirus (CMV)-negative recipients of CMV-positive organs), hypogammaglobulinemia (for example, hypogammaglobulinemic neonates with risk factor for infection or morbidity), epilepsy (for example, intractable epilepsy), systemic vasculitic syndromes, myasthenia gravis (for example, decompensation in myasthenia gravis), dermatomyositis, and polymyositis.

Further autoimmune diseases, disorders and conditions include, but are not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (for example, IgA nephropathy), multiple sclerosis, neuritis, uveitis ophthalmia, polyendocrinopathies, purpura (for example, Henloch-Scoenlein purpura), Reiter's disease, stiff-man syndrome, autoimmune pulmonary inflammation, Guillain-Barre Syndrome, insulin dependent diabetes mellitis, and autoimmune inflammatory eye disease.

Additional autoimmune diseases, disorders or conditions include, but are not limited to, autoimmune thyroiditis; hypothyroidism, including Hashimoto's thyroiditis and thyroiditis characterized, for example, by cell-mediated and humoral thyroid cytotoxicity; SLE (which is often characterized, for example, by circulating and locally generated immune complexes); Goodpasture's syndrome (which is often characterized, for example, by anti-basement membrane antibodies); pemphigus (which is often characterized, for example, by epidermal acantholytic antibodies); receptor autoimmunities such as, for example, Graves' disease (which is often characterized, for example, by antibodies to a thyroid stimulating hormone receptor) myasthenia gravis, (which is often characterized, for example, by acetylcholine receptor antibodies); insulin resistance (which is often characterized, for example, by insulin receptor antibodies); autoimmune hemolytic anemia (which is often characterized, for example, by phagocytosis of antibody-sensitized red blood cells); and autoimmune thrombocytopenic purpura (which is often characterized, for example, by phagocytosis of antibody-sensitized platelets).

Further autoimmune diseases, disorders or conditions include, but are not limited to, rheumatoid arthritis (which is often characterized, for example, by immune complexes in joints); scleroderma with anti-collagen antibodies (which is often characterized, for example, by nucleolar and other nuclear antibodies); mixed connective tissue disease, (which is often characterized, for example, by antibodies to extractable nuclear antigens, for example, ribonucleoprotein); polymyositis/dermatomyositis (which is often characterized, for example, by nonhistone anti-nuclear antibodies); pernicious anemia (which is often characterized, for example, by antiparietal cell, antimicrosome, and anti-intrinsic factor antibodies); idiopathic Addison's disease (which is often characterized, for example, by humoral and cell-mediated adrenal cytotoxicity); infertility (which is often characterized, for example, by antispennatozoal antibodies); glomerulonephritis (which is often characterized, for example, by glomerular basement membrane antibodies or immune complexes); primary glomerulonephritis, IgA nephropathy; bullous pemphigoid (which is often characterized, for example, by IgG and complement in the basement membrane); Sjogren's syndrome (which is often characterized, for example, by multiple tissue antibodies and/or the specific nonhistone antinuclear antibody (SS-B)); diabetes mellitus (which is often characterized, for example, by cell-mediated and humoral islet cell antibodies); and adrenergic drug resistance, including adrenergic drug resistance with asthma or cystic fibrosis (which is often characterized, for example, by beta-adrenergic receptor antibodies).

Still further autoimmune diseases, disorders or conditions include, but are not limited to chronic active hepatitis (which is often characterized, for example by smooth muscle antibodies); primary biliary cirrhosis (which is often characterized, for example, by anti-mitchondrial antibodies); other endocrine gland failure (which is characterized, for example, by specific tissue antibodies in some cases); vitiligo (which is often characterized, for example, by anti-melanocyte antibodies); vasculitis (which is often characterized, for example, by immunoglobulin and complement in vessel walls and/or low serum complement); post-myocardial infarction conditions (which are often characterized, for example, by anti-myocardial antibodies); cardiotomy syndrome (which is often characterized, for example, by anti-myocardial antibodies); urticaria (which is often characterized, for example, by IgG and IgM antibodies to IgE); atopic dermatitis (which is often characterized, for example, by IgG and IgM antibodies to IgE); asthma (which is often characterized, for example, by IgG and IgM antibodies to IgE); inflammatory myopathies; and other inflammatory, granulomatous, degenerative, and atrophic disorders.

In other embodiments, the compositions of the invention may be used to modulate cellular proliferation and/or survival and, accordingly, for treating or preventing diseases, disorders or conditions characterized by abnormalities in cellular proliferation and/or survival. For example, in certain embodiments, the compositions may be used to modulate apoptosis and/or to treat diseases or conditions associated with abnormal apoptosis. Apoptosis is the term used to describe the cell signaling cascade known as programmed cell death. Various therapeutic indications exist for molecules that induce apoptosis (e.g., cancer), as well as those that inhibit apoptosis (e.g., stroke, myocardial infarction, sepsis, etc.). Apoptosis can be monitored by any of a number of available techniques known and available in the art including, for example, assays that measure fragmentation of DNA, alterations in membrane asymmetry, activation of apoptotic caspases and/or release of cytochrome C and AIF.

Illustrative diseases associated with increased cell survival, or the inhibition of apoptosis include, but are not limited to, cancers (such as follicular lymphomas, carcinomas, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Graves' disease, Hashimoto's thyroiditis, autoimmune diabetes, biliary cirrhosis, Behcet's disease, Crohn's disease, polymyositis, systemic lupus erythematosus and immune-related glomerulonephritis, autoimmune gastritis, autoimmune thrombocytopenic purpura, and rheumatoid arthritis), viral infections (such as herpes viruses, pox viruses and adenoviruses), inflammation, graft vs. host disease (acute and/or chronic), acute graft rejection, and chronic graft rejection.

Further illustrative diseases or conditions associated with increased cell survival include, but are not limited to, progression and/or metastases of malignancies and related disorders such as leukemia (including acute leukemias (for example, acute lymphocytic leukemia, acute myelocytic leukemia, including myeloblastic, promyelocytic, myelomonocytic, monocytic, and erythroleukemia)) and chronic leukemias (for example, chronic myelocytic (granulocytic) leukemia and chronic lymphocytic leukemia), myelodysplastic syndrome, polycythemia vera, lymphomas (for example, Hodgkin's disease and non-Hodgkin's disease), multiple myeloma, Waldenstrom's macroglobulinemia, heavy chain diseases, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Illustrative diseases associated with increased apoptosis include, but are not limited to, AIDS (such as HIV-induced nephropathy and HIV encephalitis), neurodegenerative disorders (such as Alzheimer's disease, Parkinson's disease, amyotrophic lateral sclerosis, retinitis pigmentosa, cerebellar degeneration and brain tumor or prior associated disease), autoimmune disorders such as multiple sclerosis, Sjogren's syndrome, Graves' disease, Hashimoto's thyroiditis, autoimmune diabetes, biliary cirrhosis, Behcet's disease, Crohn's disease, polymyositis, systemic lupus erythematosus, immune-related glomerulonephritis, autoimmune gastritis, thrombocytopenic purpura, rheumatoid arthritis, myelodysplastic syndromes (such as aplastic anemia), graft vs. host disease (acute and/or chronic), ischemic injury (such as that caused by myocardial infarction, stroke and reperfusion injury), liver injury or disease (for example, hepatitis related liver injury, cirrhosis, ischemia/reperfusion injury, cholestosis (bile duct injury) and liver cancer), toxin-induced liver disease (such as that caused by alcohol), septic shock, ulcerative colitis, cachexia, and anorexia.

In still further embodiments, the compositions of the invention may be used in the treatment of neuronal/neurological diseases or disorders, illustrative examples of which include Parkinson's disease, Alzheimer's disease, Pick's Disease, Creutzfeldt-Jacob disease, Huntington's chorea, alternating hemiplegia, amyotrophic lateral sclerosis, ataxia, cerebral palsy, chronic fatigue syndrome, chronic pain syndromes, congenital neurological anomalies, cranial nerve diseases, delirium, dementia, demyelinating diseases, dysautonomia, epilepsy, headaches, Huntington's disease, hydrocephalus, meningitis, movement disorders, muscle diseases, nervous system neoplasms, neurocutaneous syndromes, neurodegenerative diseases, neurotoxicity syndromes, ocular motility disorders, peripheral nervous system disorders, pituitary disorders, porencephaly, Rett syndrome, sleep disorders, spinal cord disorders, stroke, sydenham's chorea, tourette syndrome, nervous system trauma and injuries, etc.

Furthermore, additional embodiments relate to the use of the compositions of the invention in the treatment of metabolic disorders such as adrenoleukodystrophy, Krabbe's disease (globoid cell leukodystrophy), metachromatic leukodystrophy, Alexander's disease, Canavan's disease (spongiform leukodystrophy), Pelizaeus-Merzbacher disease, Cockayne's syndrome, Hurler's disease, Lowe's syndrome, Leigh's disease, Wilson's disease, Hallervorden-Spatz disease, Tay-Sachs disease, etc. The utility of the compositions of the invention in modulating metabolic processes may be monitored using any of a variety of techniques known and available in the art including, for example, assays which measure adipocyte lipogenesis or adipocyte lipolysis.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Figure 2A:
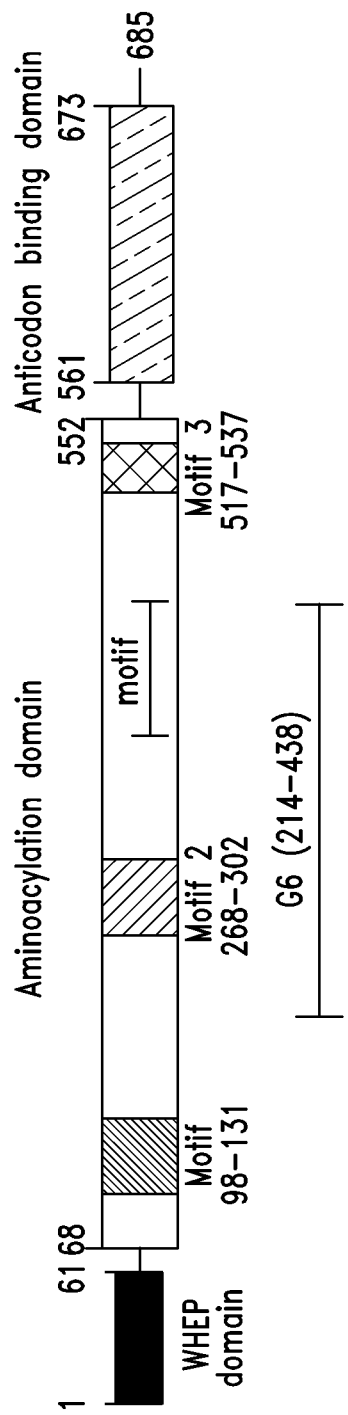
FIGS. 2A-2C show the identification of a fragment of human GlyRS containing a structural motif of the invention and demonstration that the fragment has chemokine activity.
Figure 2B:
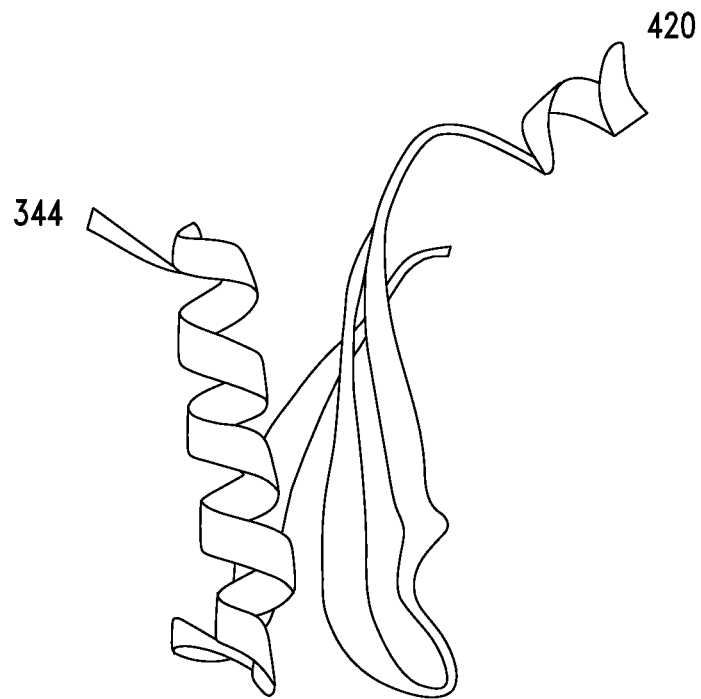
Figure 2C:
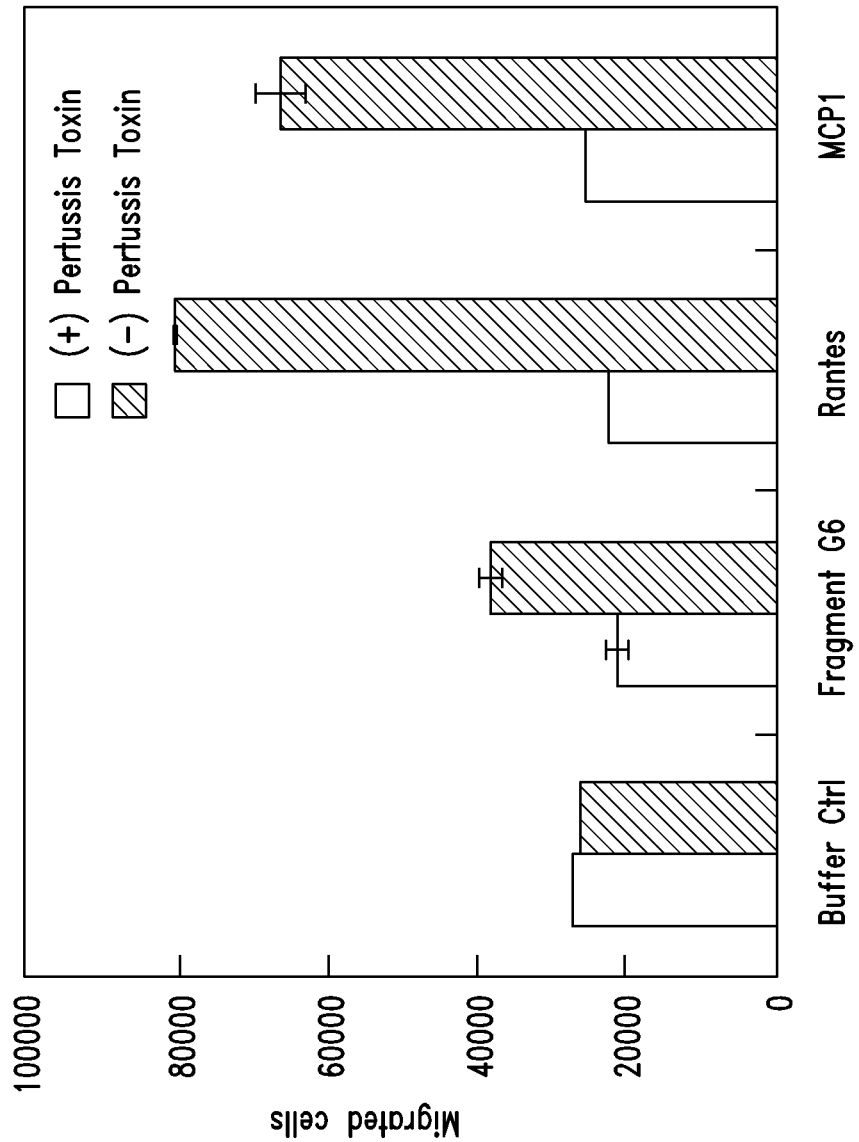
Figure 3:
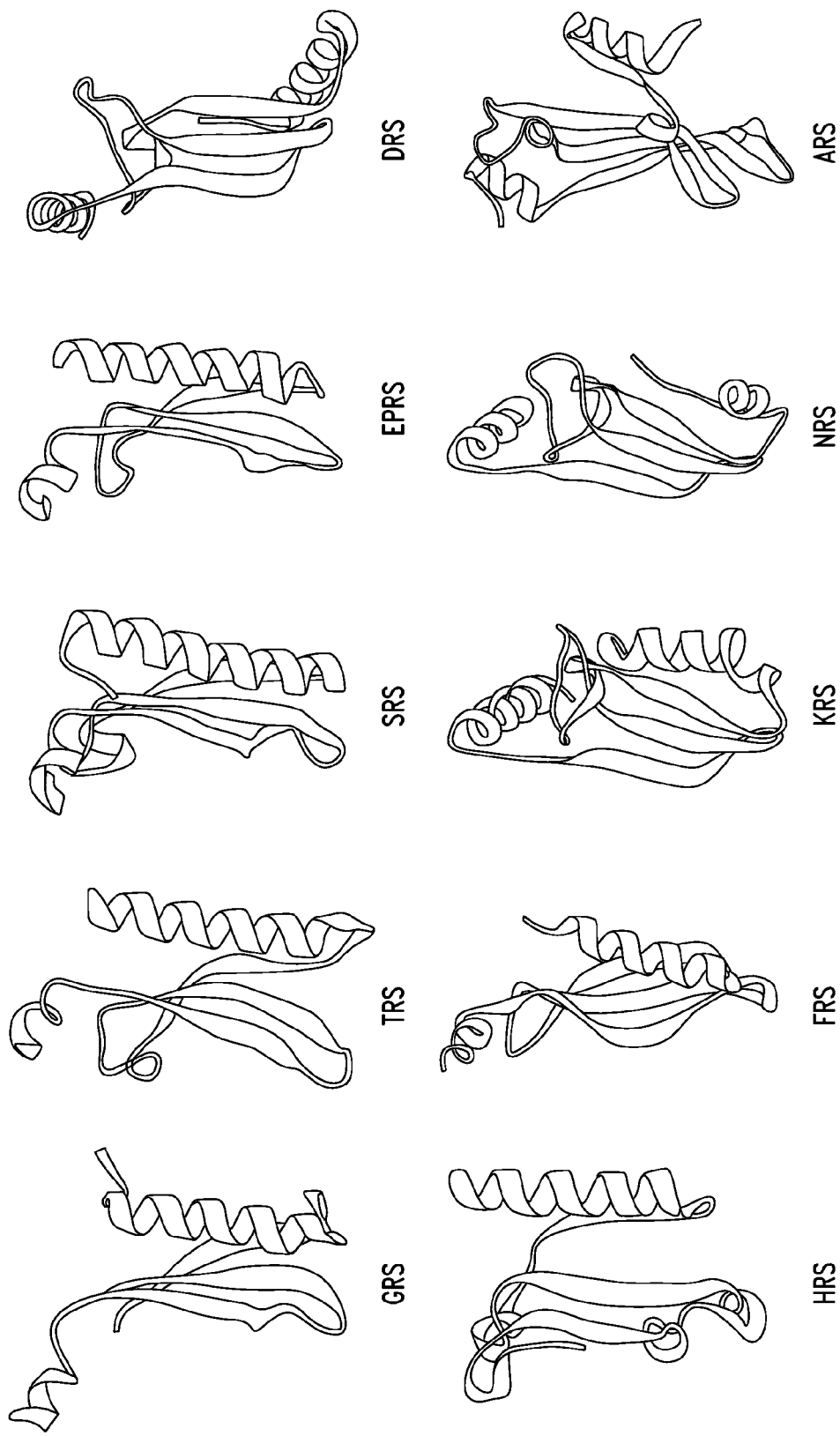
FIG. 3 shows that the identified structural motif is found in other class II AARS proteins, including GlyRS (GRS), ThrRS (TRS), HisRS (HRS), AspRS (DRS), GluProRS (EPRS), SerRS(SRS), AsnRS (NRS), AlaRS (ARS), PheRS (FRS) and LysRS (KRS).

Identification of Structural Motif within a GlyRS Polypeptide Fragment Having Cell Signaling Activity As shown in FIGS. 2A-2C, a fragment of human glycyl-tRNA synthetase (GlyRS) referred to as G6, and corresponding to residues 214-439 of human GlyRS (SEQ ID NO: 1), was unexpectedly discovered to be effective in inducing GPCR-dependent chemotaxis of THP-1 monocytes. Further analysis of this active fragment revealed the presence of a structural motif, comprising 3 antiparallel β-sheets flanked by an α-helix at each end, believed to be responsible for the observed chemokine activity. The structural motif was identified as being contained within amino acid residues 345-438 of the human GlyRS protein sequence set forth in SEQ ID NO: 1.

Example 2

Identification of Structural Motif in Other Class II AARS Proteins

Figure 4:
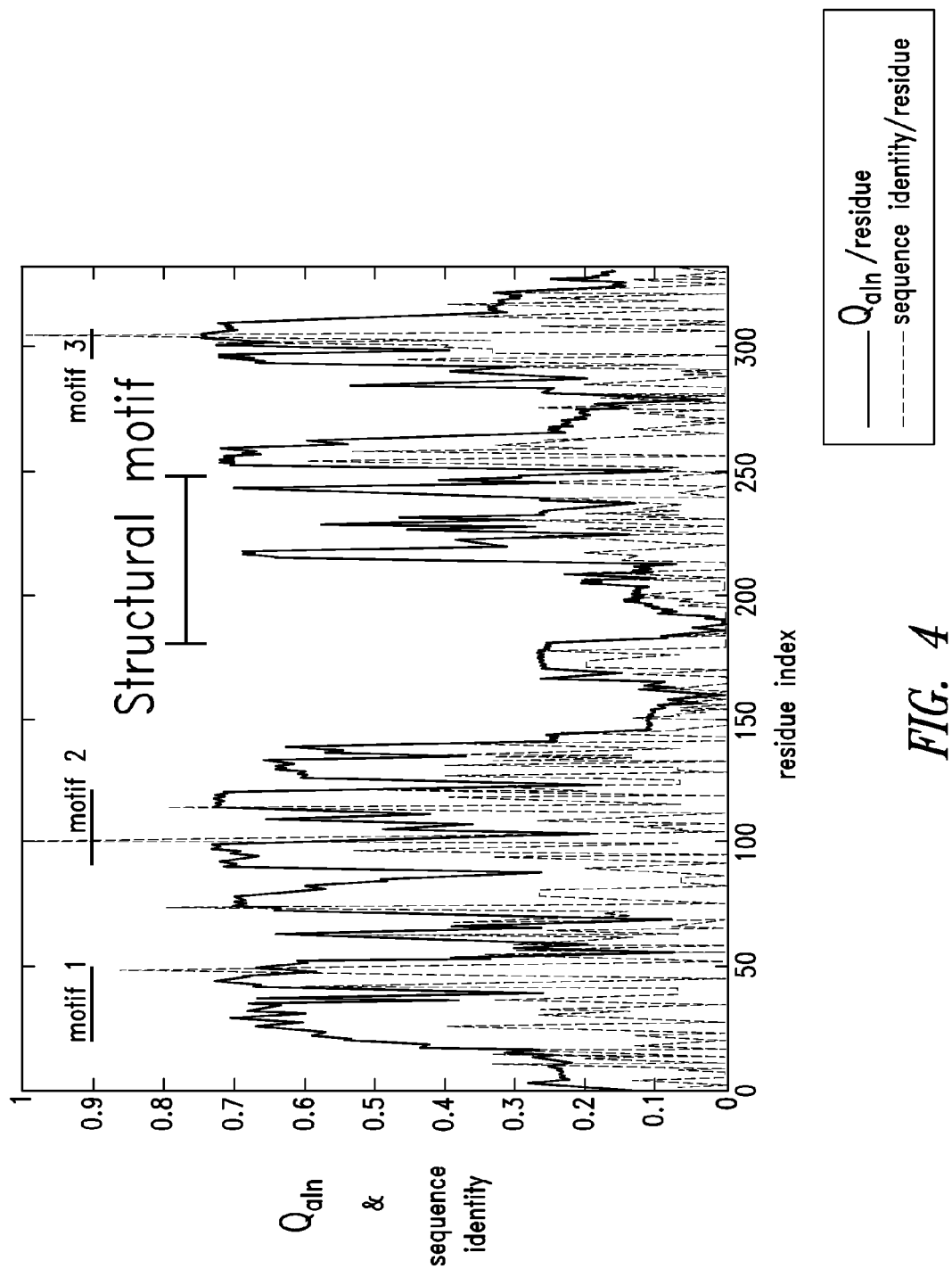
FIG. 4 shows the structural conservation of a motif of the invention across multiple class II AARS proteins, despite its relatively low sequence conservation.

The structural motif identified above in Example 1 was also found in similar regions of other human Class II AARS. These included AspRS, HisRS, ThrRS, GluProRS and SerRS. This region of Class II AARS proteins is highly conserved structurally among members of this AARS class indicating that the region contains the same basic structural architecture, but is not well conserved in residue sequence identity, creating the potential to display different sequences which may have different signaling activities on this architecture. (e.g., FIG. 4, adapted from O'Donoghue and Luthey-Schulten, Microbiology and Molecular Biology Reviews, December 2003)

The structural motif was identified as being contained within amino acid residues 367-448 of the human AspRS protein sequence set forth in SEQ ID NO: 2; within amino acid residues 294-372 of the human HisRS protein set forth in SEQ ID NO: 3; within amino acid residues 469-586 of the human ThrRS protein set forth in SEQ ID NO: 4; within amino acid residues 1171-1253 of the human GluProRS protein set forth in SEQ ID NO: 5; within amino acid residues 325-410 of the human SerRS protein set forth in SEQ ID NO: 6; within amino acid residues 380-449 of the human PheRS protein set forth in SEQ ID NO: 7; within amino acid residues 425-523 of the human LysRS protein set forth in SEQ ID NO: 8; within amino acid residues 416-494 of the human AsnRS protein set forth in SEQ ID NO: 9; and within amino acid residues 148-258 of the human AlaRS protein set forth in SEQ ID NO: 10.

Example 3

Illustrative Non-AARS Proteins Containing the Structural Motif

Figure 5C:
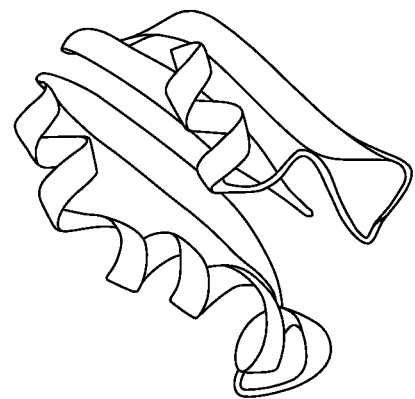
FIGS. 5A-C show that a structural motif of the invention is also found in non-AARS proteins, including (A) human thioredoxin, (B) macrophage inhibitory protein (residues 1-90), and (C) peroxiredoxin 5 isoform B (residues 32-68 and 125-161). One feature of the proteins that share this structural motif is that they are unconventionally secreted.
Figure 5B:
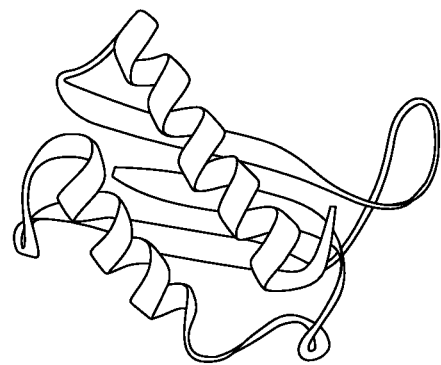
Figure 5A:
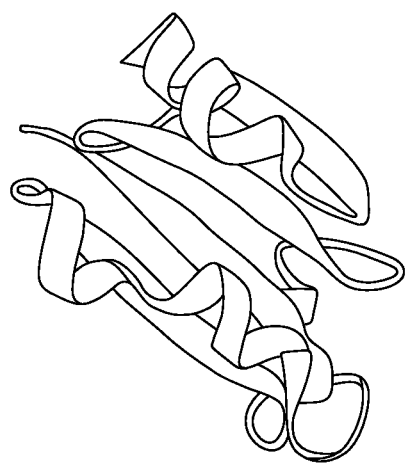
Figure 6:
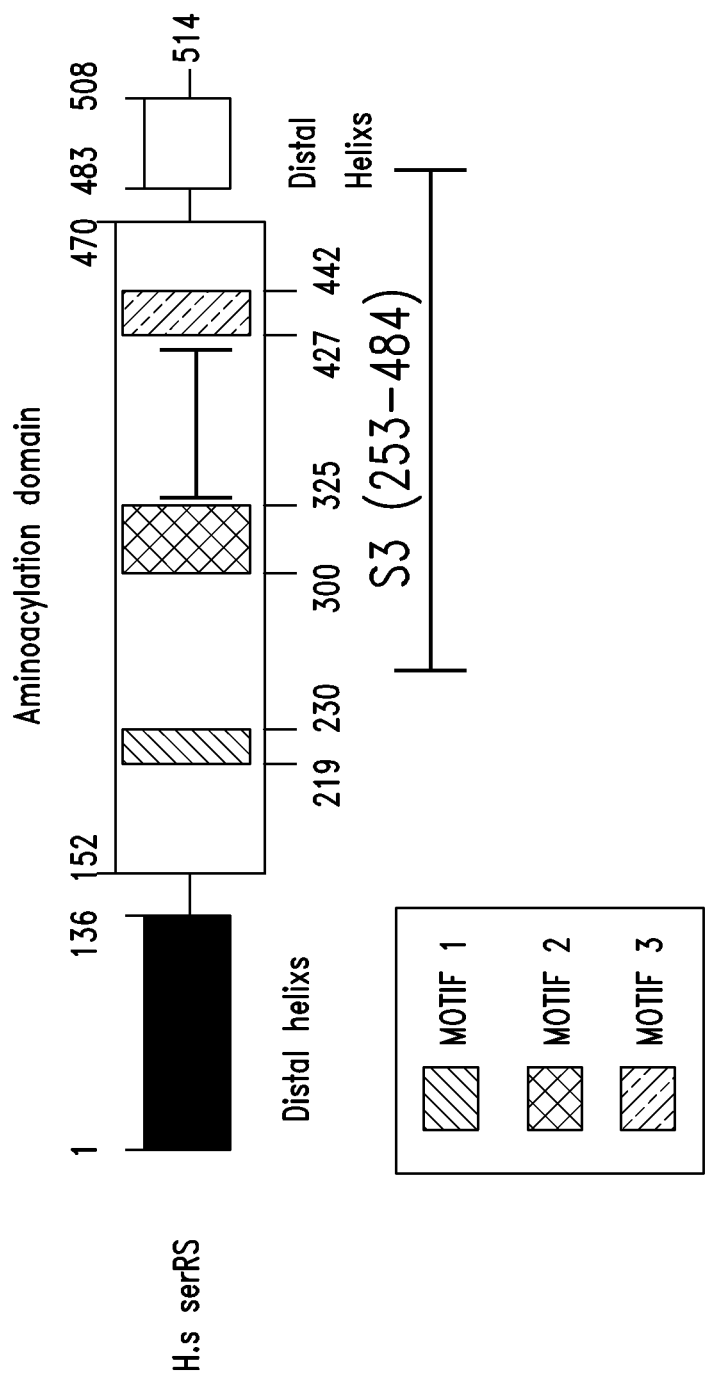
FIG. 6 shows that a structural motif of the invention is found within a fragment of human seryl tRNA synthetase (SerRS) that exhibits cell-signaling activity. This figure shows the location of the S3 fragment (residues 253-484 of full-length SerRS) and the structural motif (residues 325-410) within the full-length SerRS polypeptide sequence.

Further analysis identified the presence of this same structural motif comprising 3 antiparallel β-sheets and two α-helices in several non-AARS proteins (FIG. 5). For example, the motif was identified in human thioredoxin, contained within residues 20-105 of the human thioredoxin sequence of SEQ ID NO: 11, as well as within residues 20-84 of Trx80, which is a truncated, secreted form of thioredoxin containing the N-terminal 84 amino acid residues.

The motif was also identified in the human macrophage inhibitory factor protein, contained within residues 1-90 of the human thioredoxin sequence of SEQ ID NO: 12.

The motif was also identified in the human human peroxiredoxin 5 isoform B protein, contained within non-contiguous fragments corresponding to residues 32-68 and 125-161 of the human peroxiredoxin 5 isoform B sequence of SEQ ID NO: 13.

Thus, by screening non-AARS proteins for the presence of the identified structural motif, the present invention provides a means for identifying protein fragments having potential non-canonical biological activities of therapeutic relevance.

Example 4

Identification of Structural Motif within a SerRS Polypeptide Fragment Having Cell Signaling Activity As shown in FIG. 7, a fragment of human seryl-tRNA synthetase (SerRS) referred to as S3, and corresponding to residues 253-484 of full-length human SerRS (SEQ ID NO: 6), was unexpectedly discovered to be effective in binding to human monocytes and B-cells, stimulating secretion of TNF-α from a human monocytic cell line, and signaling through Toll-like receptor 2. Further analysis of this active fragment revealed the presence of a structural motif, comprising 3 antiparallel β-sheets flanked by an α-helix at each end, believed to be responsible for the observed activity. The structural motif was identified as being contained within amino acid residues 325-410 of the human SerRS protein sequence set forth in SEQ ID NO: 6.

Figure 7A:
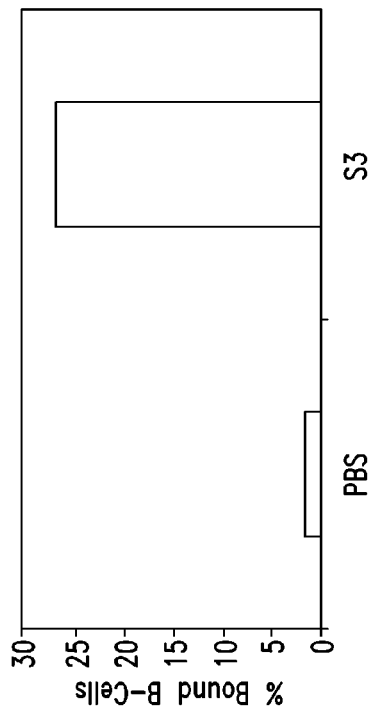
FIGS. 7A-7C show that the S3 fragment (residues 253-484 of full-length SerRS) containing a structural motif of the invention binds to human monocytes and B-cells and stimulates secretion of TNF-α from a human monocytic cell line.
Figure 7B:
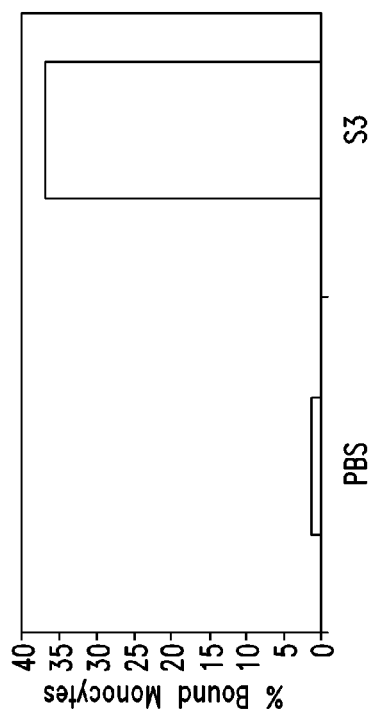

For S3 binding, peripheral blood mononuclear cells (PBMCs) were purified from a healthy blood donor and resuspended in RPMI with 10% FBS at 1×10$^7$ per ml. 1×10$^6$ cells in 100 μl of media were then treated with PBS or 500 nM S3. After 45 minutes cells were washed twice with 1 mL of staining buffer (PBS+2% FBS) and stained with αV5-FITC antibody from Invitrogen (Catalog #R96325), CD19 for B-cells (BD catalog #555413), in staining buffer with 200 μg/ml human IgG for 30 minutes. Cells were then washed twice with 1 mL staining buffer, resuspended and analyzed by FACS. The results are shown in FIG. 7A, which shows S3 binding to human monocytes, and FIG. 7B, which shows S3 binding to human B-cells, as compared to a PBS negative control.

Figure 7C:
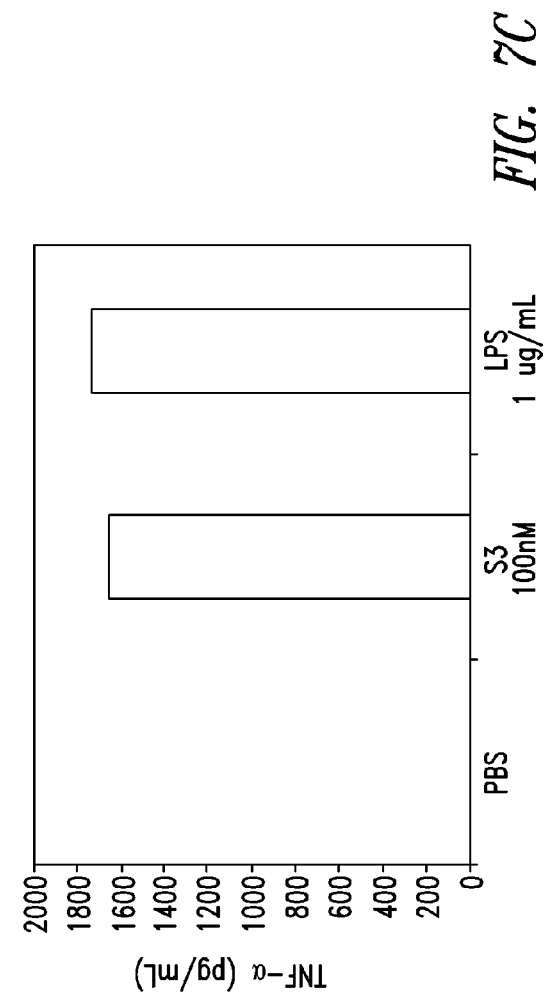

For TNFα secretion, THP cells were cultured in RPMI media with 10% FBS and 0.5 mM BME. One million cells were treated with PBS, S3 (100 nM), or Lipopolysaccharide (LPS, 1 μg/mL). After 4 hours, cell supernatants were collected by centrifugation at 2000×g for 10 minutes and evaluated in a TNFα ELISA (R&D Systems; Cat.#DTA00C) per kit directions. The results are shown in FIG. 7C, which shows induction of TNF-α secretion from human monocytic cell line (THP-1), as compared to an LPS positive control and a PBS negative control.

Figure 8:
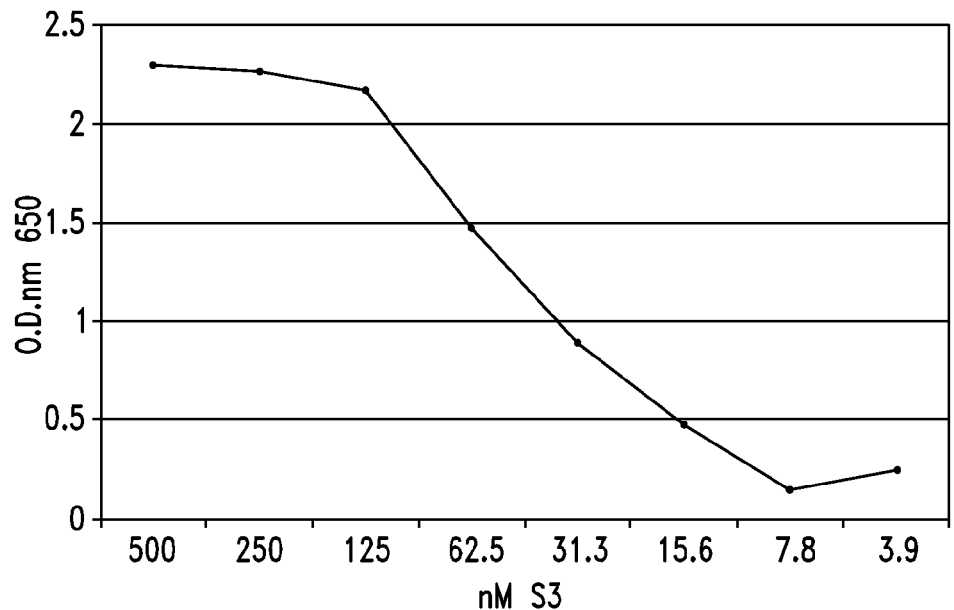
FIG. 8 shows that the S3 fragment signaled through Toll-like receptor 2 to elicit a strong secretion of alkaline phoshpatase in a dose-dependent manner (x-axis=dosage in nM; y-axis=$OD_{600}$).

For signaling through Toll-like receptor 2, HEK-Blue 2 cells (Invivogen #hb2-cells) stably transfected with mouse toll-like receptor 2 (mTLR2) linked to an NFκB alkaline phosphatase reporter gene were treated overnight with varying doses of S3 protein. The following day, media was removed and assayed four hours for secreted alkaline phosphatase using QUANTI-Blue (Invivogen #rep-qb). As shown in FIG. 8, treatment elicited a strong secretion of alkaline phoshpatase in a dose-dependent manner, indicating activation of the receptor and its associated NFκB signaling pathway.

Figure 9:
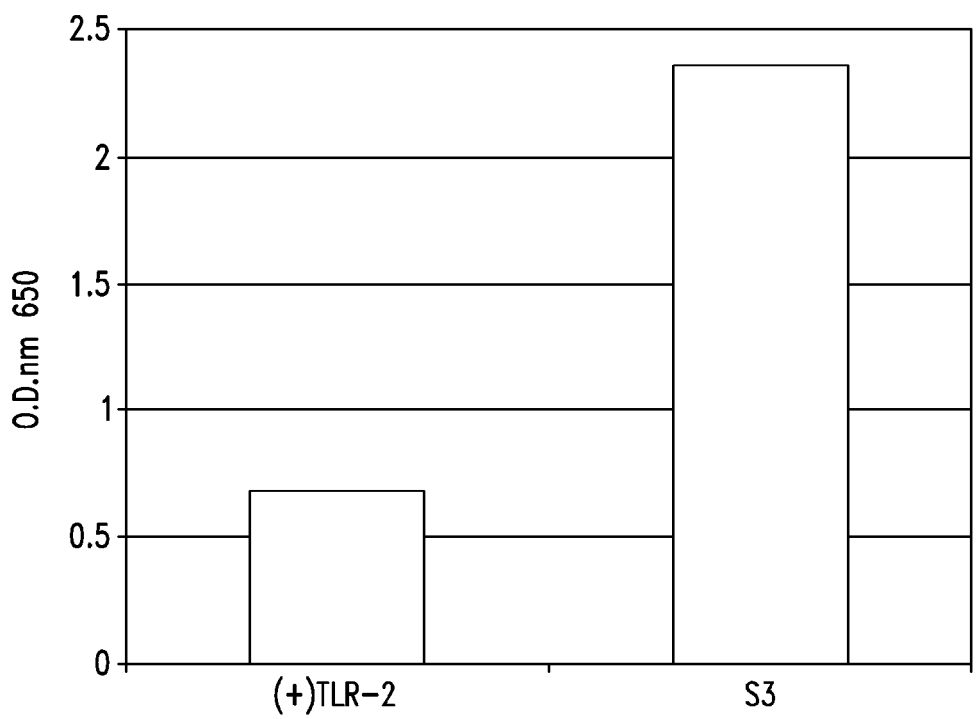
FIG. 9 shows that S3-mediated signaling through Toll-like receptor 2 (TLR2) was inhibited by pre-treatment with a monoclonal antibody that blocks binding to mTLR2.

In another experiment, the same cells were pre-treated with 5 ug/ml MAb mTLR2 (Invivogen #mab-mtlr2) (labeled (+) TLR-2) or untreated (S3) for 30 minutes, followed by overnight treatment with 250 nM S3. The following day, media was removed and assayed four hours for secreted alkaline phosphatase using QUANTI-Blue (Invivogen #rep-qb). As shown in FIG. 9, the activation of Toll-like receptor 2 was inhibited by pre-treatment with a monoclonal antibody that blocks binding to mTLR2.

What is claimed:

1. A pharmaceutical composition comprising an isolated seryl-tRNA synthetase (SerRS) polypeptide that is at least about 90% pure and consists essentially of three antiparallel β-sheets flanked at each end by an α-helix, wherein the polypeptide comprises a contiguous fragment of a human SerRS polypeptide as defined by SEQ ID NO:6, or a sequence having at least 90% sequence identity to said contiguous fragment and wherein the SeRS polypeptide is about 60 to 200 amino acid residues and exhibits a cell signaling activity.

2. The pharmaceutical composition of claim 1, wherein the polypeptide comprises at least two non-contiguous fragments of a human SerRS polypeptide, or sequences having at least 90% sequence identity to said non-contiguous fragments.

3. The pharmaceutical composition of claim 1, wherein the SerRS polypeptide consists essentially of residues 325-410 of SEQ ID NO: 6 or an active fragment or variant thereof having at least 95% sequence identity to residues 325-410 of SEQ ID NO: 6.

4. The pharmaceutical composition of claim 1, wherein the polypeptide has chemokine activity.

5. A method for modulating cell signaling comprising contacting a cell with an effective amount of a pharmaceutical composition of claim 1.

6. The method of claim 5, wherein the method is selected from a method of modulating chemokine activity, a method of modulating TNF-α secretion, a method of inducing TNF-α secretion, a method of modulating immune cell chemotaxis, and a method of inducing monocyte chemotaxis.

* * * * *